United States Patent [19]
Fujita et al.

[11] Patent Number: 5,977,374
[45] Date of Patent: Nov. 2, 1999

[54] 5-(4-HYDROXY-OR 4-ACETOXY-BENZYL)-3-TRIPHENYLMETHYLTHIAZOLIDINE-2,4-DIONE AND METHOD FOR PRODUCING SAME

[75] Inventors: Takashi Fujita; Takao Yoshioka; Horoyoshi Horikoshi; Shinji Yoshioka, all of Tokyo, Japan

[73] Assignee: Sankyo Company, Limited, Tokyo, Japan

[21] Appl. No.: 08/282,579

[22] Filed: Jul. 29, 1994

Related U.S. Application Data

[62] Division of application No. 08/178,465, Jan. 6, 1994, abandoned, which is a continuation of application No. 07/979,180, Nov. 20, 1992, abandoned.

[30] Foreign Application Priority Data

Nov. 20, 1991 [JP] Japan ................................ 3-304581

[51] Int. Cl.$^6$ ................................................ C07D 277/34
[52] U.S. Cl. ................................................ 548/183
[58] Field of Search ................................................ 548/183

[56] References Cited

U.S. PATENT DOCUMENTS

| 4,338,333 | 7/1982 | Ainsworth et al. . | |
| 5,002,953 | 3/1991 | Hindley | 514/275 |
| 5,037,842 | 8/1991 | Goldstein | 514/375 |
| 5,153,210 | 10/1992 | Ainsworth et al. . | |
| 5,194,443 | 3/1993 | Hindley et al. . | |
| 5,508,296 | 4/1996 | Nigata | 514/369 |

FOREIGN PATENT DOCUMENTS

| 0 006 735 | 1/1980 | European Pat. Off. . |
| 0 021 636 A1 | 1/1981 | European Pat. Off. . |
| 0 025 331 | 3/1981 | European Pat. Off. . |
| 0 021 636 B1 | 12/1982 | European Pat. Off. . |
| 0 099 707 | 2/1984 | European Pat. Off. . |
| 0 236 624 | 9/1987 | European Pat. Off. . |
| 0 262 785 | 4/1988 | European Pat. Off. . |
| 1 200 886 | 8/1970 | United Kingdom . |
| 1 551 260 | 8/1979 | United Kingdom . |
| WO 90/13535 | 11/1990 | WIPO . |

OTHER PUBLICATIONS

Greene, Protective Groups in Organic Synthesis pp. 407, 411–412, 449–450 (2nd Ed) 1991.

Greene, Protective Groups in Organic Synthesis pp. 366–367 & 2nd Ed. 1991.

McOmie, Protective Groups in Organic Chemistry p. 63 (1985).

Journal of Medicinal Chemistry, vol. 13, No. 4, 674–680 (1970), D.T. Collin et al, "Saligenin Analogs of Sympathomimetic Catecholamines".

*Primary Examiner*—Robert Gerstl
*Attorney, Agent, or Firm*—Frishauf, Holtz, Goodman, Langer & Chick, P.C.

[57] ABSTRACT

A compound of the formula

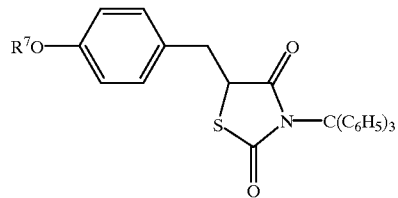

wherein $R^7$ is a hydrogen atom or an acetyl group, and process for preparing said compounds.

1 Claim, No Drawings

5-(4-HYDROXY-OR 4-ACETOXY-BENZYL)-3-TRIPHENYLMETHYLTHIAZOLIDINE-2,4-DIONE AND METHOD FOR PRODUCING SAME

This is a division of application Ser. No. 08/178,465 filed Jan. 6, 1994, now abandoned, which is a continuation of application Ser. No. 07/979,180 filed Nov. 20, 1992 (abandoned).

BACKGROUND TO THE INVENTION

The present invention relates to a series of compounds which are characterised by a 2-[2-(substituted phenyl-oxy, thio or methyl)-1-methylethyl]aminoethanol structure and which have valuable anti-diabetic and anti-obesity activities; in addition, they are capable of treating or preventing hyperlipemia and hyperglycemia and, by inhibiting the action of aldose reductase, they can also be effective in the treatment and prevention of complications of diabetes. They are also effective in the treatment and prophylaxis of obesity-related hypertension and osteoporosis. The invention also provides processes for preparing the compounds of the present invention, as well as methods and compositions using them.

A number of compounds of this general type is known, and some have been disclosed to have anti-diabetic and/or anti-obesity activity. The known compounds which are structurally related to the compounds of the present invention may be represented by the general formula (A):

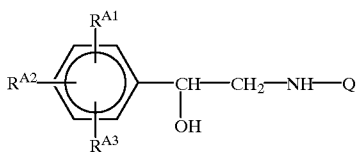

(A)

For example, D. T. Collin et al. [J. Med. Chem., 13, 674–680 (1970)] disclose compounds in which Q represents, inter alia, an isopropyl group, a t-butyl group or a 2-phenyl-1-methylethyl group, and at least one of $R^{A1}$, $R^{A2}$ and $R^{A3}$ represents a hydrogen atom, and the other two of $R^{A1}$, $R^{A2}$ and $R^{A3}$ represent, for example, hydroxy groups, alkoxy groups, carboxy groups (or esterified carboxy groups) or hydroxymethyl groups. These compounds are said to have an agonistic activity against the β-adrenergic receptors, and are not disclosed as having the same kinds of activities as do the compounds of the present invention.

UK Patent Specification No. 1 551 260 also discloses that compounds represented by the general formula (A), but in which Q represents a phenylaminoethyl group, have the same activity.

UK Patent Specification No. 1 200 886 also discloses compounds represented by the general formula (A), but in which Q represents a hydroxybenzyl, alkoxybenzyl or 2-phenoxy-1-methylethyl group, and these compounds are also alleged to have a p-adrenergic stimulant and blocking activity.

European Patent Publication No. 6735 also discloses a series of compounds of formula (A) in which Q represents a group of formula (B):

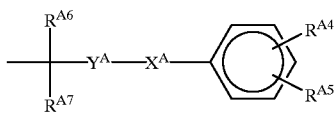

(B)

wherein $R^{A4}$ represents a carboxy group or a salt thereof, an alkoxycarbonyl group having from 2 to 5 carbon atoms or an alkylcarbamoyl group having from 2 to 5 carbon atoms; $R^{A5}$ represents a hydrogen, chlorine or fluorine atom, a methyl group, a methoxy group, a hydroxy group, a carboxy group or a salt thereof, an alkyloxycarbonyl group having from 2 to 5 carbon atoms or an alkylcarbamoyl group having from 2 to 5 carbon atoms; $R^{A6}$ represents a hydrogen atom, or a methyl,., ethyl or propyl group; $R^{A7}$ represents a hydrogen atom, or a methyl, ethyl or propyl group; $X^A$ represents an oxygen atom or a single bond; and $Y^A$ represents an alkylene group having from 1 to 6 carbon atoms or a single bond, and these are said to have anti-hyperglycemia and anti-obesity activities.

European Patent Publication No. 21 636, which is currently thought to represent the closest prior art to the present invention, discloses compounds having the general formula (A) in which Q represents a group of formula (B), and in which: $R^{A1}$ and $R^{A2}$ each represents a hydrogen atom, a halogen atom, a hydroxy group, a hydroxymethyl group or a trifluoromethyl group, and $R^{A1}$ and $R^{A2}$ may be the same or different; $R^{A3}$ represents a hydrogen atom; $R^{A4}$ represents a hydroxy group or a lower alkyl group substituted with a lower alkoxy or lower acyloxy group; $R^{A5}$ represents a hydrogen atom; $R^{A6}$ and $R^{A7}$ each represents a hydrogen atom or a methyl group, and $R^{A6}$ and $R^{A7}$ may be the same or different; $X^A$ represents an oxygen atom or a single bond; and $Y^A$ represents a methylene or ethylene group. These are also said to have anti-hyperglycemia and anti-obesity activity. Certain of the compounds of the present invention are a selection from those disclosed in this document and have the advantages that they have little effect on the receptors of the central nervous system, such as the muscarine, N-methyl-D-aspartate and serotonin (5-$HT_1$, 5-$HT_2$ and 5-$HT_3$) receptors. They also have no effect on the cardiovascular system because they have no inotropic activity (right atrium) or chronotropic activity (right atrium). As a result, the compounds of the present invention have far fewer side effects and can thus be expected to find a wider range of practical uses.

European Patent Publication No. 25 331 discloses compounds having the general formula (A), in which Q represents a group of formula (C):

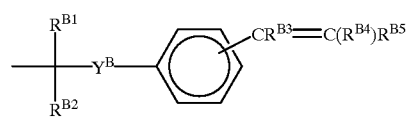

(C)

and $R^{A1}$, $R^{A2}$ and $R^{A3}$ are the same or different and each represents a hydrogen, fluorine, chlorine or bromine atom or a trifluoromethyl group; $R^{B1}$, $R^{B2}$, $R^{B3}$ and $R^{B4}$ each represents a hydrogen atom or a lower alkyl group, and $R^{B1}$, $R^{B2}$, $R^{B3}$ and $R^{B4}$ may be the same or different; $R^{B5}$ represents a carboxy group, a lower alkyl ester thereof or a group of formula —CONHR$^{B6}$ (in which $R^{B6}$ represents a hydrogen atom or a lower alkyl group); and $Y^B$ represents an alkylene group having 1 or 2 carbon atoms. These are said to have anti-hyperglycemia and anti-obesity activity.

U.S. Pat. No. 4,338,333 discloses that compounds having the general formula (A) in which Q represents a group of formula (B) and $R^{A1}$ represents a hydrogen or halogen atom, or a hydroxy, hydroxymethyl or trifluoromethyl group; $R^{A2}$ and $R^{A3}$ are the same or different and each represents a hydrogen or halogen atom or a hydroxy group; $R^{A6}$ and $R^{A7}$ are the same or different and each represents a hydrogen atom or a methyl group; $R^{A4}$ represents a hydrogen atom; $X^A$ represents an oxygen atom or a single bond; $Y^A$ represents a methylene or ethylene group; and $R^{A8}$ represents a group —O—$Z^A$—COOH, where $Z^A$ represents an alkylene group having less than 3 carbon atoms or an alkenylene group having less than 3 carbon atoms, and salts, esters and amides thereof have a preventative activity against hyperglycemia and obesity.

European Patent Publication No. 262 785, moreover, discloses that, of the compounds having this formula, 2-[2-(4-carboxymethoxyphenyl)-1(R)-1-methylethyl]amino-1(R)-(3-chlorophenyl)ethanol and its methyl ester and pharmaceutically acceptable salts thereof (referred to as the "RR-isomer"), which may optionally contain some proportion of 2-[2-(4-carboxymethoxyphenyl)-1(S)-1-methylethyl]amino-1(S)-(3-chlorophenyl)ethanol and its methyl ester and pharmaceutically acceptable salts thereof (the "SS-isomer"), provided that the content of the SS-isomer is not more than 50% by weight of the mixture of RR- and SS-isomers, is particularly effective as an anti-hyperglycemic or anti-obese medicine.

We have now discovered a limited series of novel 2-[2-(substituted phenyl-oxy, thio or methyl)-1-methylethyl] aminoethanol derivatives which have valuable anti-diabetic and anti-obesity activities, with a low toxicity, accompanied by much fewer side effects; the compounds of the present invention, moreover, have the ability to inhibit the action of aldose reductase, and so they can also be effective in the treatment and prevention of complications of diabetes. They are also effective in the treatment and prophylaxis of obesity-related hypertension and osteoporosis.

BRIEF SUMMARY OF INVENTION

It is, therefore, an object of the present invention to provide a series of compounds of this type.

It is a further, and more specific, object of the invention to provide such compounds having anti-diabetic and anti-obesity activities, and preferably having a low toxicity, accompanied by much fewer side effects.

It is a further object of the invention to provide methods and compositions using these compounds.

Other objects and advantages will become apparent as the description proceeds.

The compounds of the present invention are those compounds of formula (I):

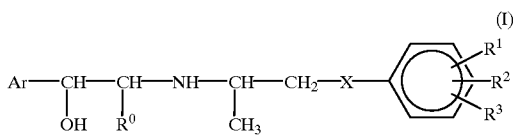

wherein:
$R^0$ represents a hydrogen atom, a methyl group or a hydroxymethyl group;

$R^1$ represents a substituted alkyl group having from 1 to 12 carbon atoms, which group is substituted by at least one substituent selected from the group consisting of substituents A, defined below;

$R^2$ and $R^3$ are independently selected from the group consisting of: hydrogen atoms; halogen atoms; hydroxy groups; alkoxy groups having from 1 to 5 carbon atoms; carboxy groups; alkoxycarbonyl groups having from 2 to 7 carbon atoms; alkyl groups having from 1 to 5 carbon atoms; nitro groups; haloalkyl groups having from 1 to 4 carbon atoms; and substituted alkyl groups which have from 1 to 12 carbon atoms and which are substituted by at least one substituent selected from the group consisting of substituents A, defined below;

X represents an oxygen or sulfur atom; and

Ar represents a group of formula (II) or (III):

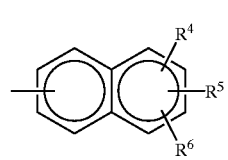

wherein:
$R^4$ represents a hydrogen atom, a halogen atom, a hydroxy group, a hydroxymethyl group, an alkoxy group having from 1 to 5 carbon atoms, an alkyl group having from 1 to S carbon atoms, an aliphatic carboxylic acyloxy group having from 1 to 6 carbon atoms, a nitro group, a cyano group, an aralkyloxy group, in which the aralkyl part is as defined below, an aryloxy group in which the aryl part is as defined below, an aryl group as defined below or a haloalkyl group having from 1 to 4 carbon atoms;

$R^5$ represents a hydrogen atom, a halogen atom, a hydroxy group, an alkoxy group having from 1 to 5 carbon atoms, an alkyl group having from 1 to 5 carbon atoms or a nitro group; and $R^6$ represents a hydrogen atom, a halogen atom, a hydroxy group, an alkoxy group having from 1 to 5 carbon atoms or an alkyl group having from 1 to 5 carbon atoms;

said aralkyl part is an alkyl group which has from 1 to 3 carbon atoms and which is substituted by 1 or 2 aryl groups as defined below;

said aryl groups are carbocyclic aryl groups which have from 6 to 10 ring carbon atoms and which are unsubstituted or are substituted by at least one substituent selected from the group consisting of substituents B, defined below;

said substituents A are selected from the group consisting of carboxy groups, alkoxycarbonyl groups having from 2 to 7 carbon atoms, aryloxycarbonyl groups in which the aryl part is as defined above, aralkyloxycarbonyl groups in which the aralkyl part is as defined above, alkylcarbamoyl groups in which the alkyl part has from 1 to 6 carbon atoms, dialkylcarbamoyl groups in which each alkyl part has from 1 to 4 carbon atoms, carbamoyl groups, hydroxycarbamoyl groups, hydroxy groups, carboxylic acyloxy groups having from 1 to 6 carbon atoms and 2,4-dioxothiazolidin-5-yl groups; and said substituents B are selected from the group consisting of halogen atoms, alkyl groups having from 1 to 4 carbon atoms, alkoxy groups having from 1 to 3 carbon atoms, nitro groups, haloalkyl groups having from 1 to 4 carbon atoms and hydroxy groups;

and pharmaceutically acceptable salts thereof.

The invention also provides a pharmaceutical composition for the treatment or prophylaxis of diabetes, obesity, hyperlipemia, hyperglycemia, complications of diabetes, obesity-related hypertension and osteoporosis, which composition comprises an effective amount of an active compound in admixture with a pharmaceutically acceptable carrier or diluent, wherein the active compound is selected from the group consisting of compounds of formula (I) and pharmaceutically acceptable salts thereof.

The invention also provides a method for the treatment or prophylaxis of diabetes, obesity, hyperlipemia, hyperglycemia, complications of diabetes, obesity-related hypertension and osteoporosis in a mammal, which may be human, which method comprises administering to said mammal an effective amount of an active compound, wherein the active compound is selected from the group consisting of compounds of formula (I) and pharmaceutically acceptable salts thereof.

The invention also provides processes for preparing the compounds of the present invention, which are described in more detail hereafter.

DETAILED DESCRIPTION OF INVENTION

In the compounds of the present invention, $R^1$ represents a substituted alkyl group having from 1 to 12 carbon atoms, which group is substituted by at least one substituent selected from the group consisting of substituents A, defined above and exemplified below. This may be a straight or branched chain alkyl group having from 1 to 12 carbon atoms, and examples include the methyl, ethyl, propyl, butyl, pentyl, hexyl, heptyl, octyl, nonyl, decyl, undecyl, dodecyl, isopropyl, isobutyl, sec-butyl, t-butyl, 1-methylbutyl, 2-methylbutyl, 3-methylbutyl, 1-ethylpropyl, 1,1-dimethylpropyl, 1,2-dimethylpropyl, 2,2-dimethylpropyl, 3-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-methylhexyl, 1-ethylpentyl and 1-propylbutyl groups. Of these, we prefer the straight or branched chain alkyl groups having from 1 to 6 carbon atoms, and most prefer the straight or branched chain alkyl groups having from 1 to 3 carbon atoms.

This alkyl group represented by $R^1$ is substituted by at least one of substituents A. There is no particular limitation on the number of such substituents, except such as may be imposed by the number of substitutable carbon atoms, or possibly by steric constraints. However, in general, we prefer that the number of substituents should be from 1 to n where n is the number of hydrogen atoms in the unsubstituted alkyl group or 8, whichever is the lesser. Thus, in the case of the methyl group, the number of substituents is from 1 to 3; in the case of the ethyl group, it is from 1 to 5; in the case of the propyl and isopropyl groups, it is from 1 to 7; and, in the case of the butyl and higher alkyl groups, it is from 1 to 8. In all cases, the maxima proposed may be affected by steric effects, as is well known in the art. Examples of such substituents A are as follows:

Substituent A may be a carboxy, carbamoyl, hydroxycarbamoyl, hydroxy or 2,4-dioxothiazolidin-5-yl group.

Alternatively, where substituent A is an alkoxycarbonyl group, this may be a straight or branched chain alkoxycarbonyl group having from 2 to 7 carbon atoms, examples of which include the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl and 2,2-dimethylpropoxycarbonyl groups, of which we prefer the straight or branched chain alkoxycarbonyl groups having from 2 to 5 carbon atoms and most prefer the straight chain alkoxycarbonyl groups having 2 or 3 carbon atoms.

Where substituent A is an optionally substituted aryloxycarbonyl group, the aryl part is as defined above and exemplified below. These groups have, in total, from 7 to 11 carbon atoms, and may be unsubstituted or may be substituted by at least one of substitutents B, defined above and exemplified below. There are no particular limitations on the number of substituents which may be used, except such as may be imposed by the number of substitutable positions and possibly by steric constraints; however, in general, from 1 to 5 substituents are preferred, from 1 to 3 substituents being more preferred. Examples of unsubstituted aryloxycarbonyl groups include the phenoxycarbonyl, 1-naphthyloxycarbonyl and 2-naphthyloxycarbonyl groups. Examples of substituted aryloxycarbonyl groups include any of the unsubstituted groups exemplified above but which is substituted by at least one of substituents B, and specific examples of such substituted groups include the o-, m- or p-fluorophenoxycarbonyl, o-, m- or p-chlorophenoxycarbonyl, o-, m- or p-methylphenoxycarbonyl, o-, m- or p-methoxyphenoxycarbonyl, o-, m- or p-nitrophenoxycarbonyl, o-, m- or p-trifluoromethylphenoxycarbonyl, and o-, m- or p-hydroxyphenoxycarbonyl groups. Of these, we prefer those aryloxycarbonyl groups which are unsubstituted or which have from 1 to 3 substituents selected from the group consisting of halogen atoms, alkyl groups having 1 or 2 carbon atoms, alkoxy groups having 1 or 2 carbon atoms and trifluoromethyl groups. Most preferred is the phenoxycarbonyl group which is unsubstituted or which has 1 or 2 substituents selected from the group consisting of fluorine atoms, chlorine atoms, methyl groups, methoxy groups and trifluoromethyl groups.

Where substituent A is an optionally substituted aralkyloxycarbonyl group, the aralkyl part is as defined above. The unsubstituted group has in total from 8 to 14 carbon atoms. Where the group is substituted, there is no particular limitation on the number of substituents, and this is normally only constrained by the number of substitutable positions and possibly by steric constraints. In general, from 1 to 5 substituents are preferred, from 1 to 3 being more preferred. Where the group is substituted, the substitutent is at least one of substituents B, defined above and exemplified below. The aralkyl part of the group has an alkyl part which is substituted by 1 or 2 aryl groups. Suitable alkyl groups having from 1 to 3 carbon atoms are the methyl, ethyl, propyl and isopropyl groups, and these may be substituted by 1 or 2 aryl groups, such as phenyl or naphthyl groups. Examples of unsubstituted aralkyloxycarbonyl groups include the benzyloxycarbonyl, phenethyloxycarbonyl, 1-phenylethyloxycarbonyl, 3-phenylpropyloxycarbonyl and naphthylmethoxycarbonyl groups. Examples of substituted aralkyloxycarbonyl groups include any of the unsubstituted groups exemplified above but which is substituted by at least one of substituents B, and specific examples of such substituted groups include the o-, m- or p-fluorobenzyloxycarbonyl, o-, m- or p-chlorobenzyloxycarbonyl, o-, m- or p-methylbenzyloxycarbonyl, o-, m- or p-methoxybenzyloxycarbonyl, o-, m- or p-nitrobenzyloxycarbonyl, o-, m- or p-trifluoromethylbenzyloxycarbonyl, o-, m- or p-hydroxybenzyloxycarbonyl, 3,5-di-t-butyl-4-hydroxybenzyloxycarbonyl and 3,4,5-trimethoxybenzyloxycarbonyl groups. Of these, we prefer those aralkyloxycarbonyl groups which are unsubstituted or which have from 1 to 3 substituents selected from the group consisting of halogen atoms, alkyl groups having 1 to 4 carbon atoms, alkoxy groups having 1 to 3 carbon atoms, trifluoromethyl groups or hydroxy groups. The most preferred group is the benzyloxycarbonyl group, which may be unsubstituted or may have 1 or 2 substituents selected from the group consisting of fluorine atoms, chlorine atoms, methyl groups or methoxy groups.

Where substituent A is a monoalkylcarbamoyl group, the alkyl part has from 1 to 6 carbon atoms, i.e. the group as a whole has from 2 to 7 carbon atoms. The alkyl part may be a straight or branched chain group and examples of such alkylcarbamoyl groups include the methylcarbamoyl, ethylcarbamoyl, propylcarbamoyl, isopropylcarbamoyl, butylcarbamoyl, isobutylcarbamoyl, sec-butylcarbamoyl, t-butylcarbamoyl, pentylcarbamoyl and 2,2-dimethylpropylcarbamoyl groups. Of these, we prefer those alkylcarbamoyl groups having from 2 to 5 carbon atoms.

Where substituent A is a dialkylcarbamoyl group, each alkyl part has from 1 to 4 carbon atoms, i.e. the group as a whole has from 3 to 9, preferably from 3 to 7, carbon atoms. The alkyl parts may each be a straight or branched chain group and the two alkyl groups may be the same or different. Examples of such dialkylcarbamoyl groups include the dimethylcarbamoyl, diethylcarbamoyl, N-methyl-N-ethylcarbamoyl, N-methyl-N-propylcarbamoyl, N-methyl-N-butylcarbamoyl, N-ethyl-N-propylcarbamoyl and N-ethyl-N-isopropylcarbamoyl groups. Of these, we prefer those alkylcarbamoyl groups having from 3 to 5 carbon atoms. The monoalkylcarbamoyl groups are preferred over the dialkylcarbamoyl groups.

Where substituent A is an acyloxy group, this is an aliphatic, carboxylic acyloxy group, which may be a straight or branched chain group having from 1 to 6 carbon atoms. Examples include the formyloxy, acetoxy, propionyloxy, butyryloxy, isobutyryloxy, valeryloxy, isovaleryloxy, pivaloyloxy and hexanoyloxy groups. Of these, we prefer those straight or branched chain acyloxy groups having 1 to 5 carbon atoms, and most prefer those acyloxy groups having from 1 to 3 carbon atoms.

Examples of the groups and atoms which may be included in substituents B are as follows:

halogen atoms, for example, the fluorine, chlorine, bromine and iodine atoms, preferably the fluorine, chlorine and bromine atoms;

alkyl groups having from 1 to 4 carbon atoms, which may be straight or branched chain groups, such as the methyl, ethyl, propyl, butyl, isopropyl and t-butyl groups;

alkoxy groups having from 1 to 3 carbon atoms, which may be straight or branched chain groups, such as the methoxy, ethoxy, propoxy and isopropoxy groups;

the nitro group;

haloalkyl groups having from 1 to 4 carbon atoms, and preferably having from 1 to 3 halogen atoms, which may be the same or different, such as the trifluoromethyl, trichloromethyl, difluoromethyl, dichloromethyl, dibromomethyl, 2,2,2-trichloroethyl, 2,2,2-trifluoroethyl, 2-fluoroethyl, 2,2-dibromoethyl, 3-chloropropyl, 3,3,3-trifluoropropyl and 4-fluorobutyl groups, of which we prefer alkyl groups having from 1 to 3 carbon atoms which are substituted by from 1 to 3 halogen atoms (and, where there are 2 or 3 halogen atoms, these are the same), more preferably the methyl or ethyl groups which are substituted by from 1 to 3 fluorine or chlorine atoms; the most preferred specific groups are the trifluoromethyl, trichloromethyl, difluoromethyl and 2-fluoroethyl groups, especially the trifluoromethyl group; and the hydroxy group.

$R^2$ and $R^3$ may be the same as each other or they may be different. Where $R^2$ or $R^3$ represents a halogen atom, this may be, for example, the fluorine, chlorine, bromine or iodine atom, preferably the fluorine, chlorine or bromine atom, more preferably the fluorine or chlorine atom.

Where $R^2$ or $R^3$ represents an alkoxy group, this may be a straight or branched chain alkoxy group having from 1 to 5, preferably from 1 to 3, carbon atoms, and examples include the methoxy, ethoxy, propoxy, isopropoxy, butoxy, isobutoxy and pentyloxy groups. Of these, we prefer those alkoxy groups having from 1 to 3 carbon atoms, more preferably the methoxy and ethoxy groups.

Where $R^2$ or $R^3$ represents an alkoxycarbonyl group having from 2 to 7 carbon atoms, this may be a straight or branched chain alkoxycarbonyl group and the alkoxy part contains from 1 to 6 carbon atoms. Examples of such groups include the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl 2,2-dimethylpropoxycarbonyl and hexyloxycarbonyl groups. Of these, we prefer those straight or branched chain alkoxycarbonyl groups having from 2 to 5 carbon atoms, and more prefer those alkoxycarbonyl groups having 2 or 3 carbon atoms, i.e. the methoxycarbonyl and ethoxycarbonyl groups.

Where $R^2$ or $R^3$ represents an alkyl group having from 1 to 5 carbon atoms, this may be a straight or branched chain, and examples include the methyl, ethyl, propyl, butyl, pentyl, isopropyl, isobutyl, sec-butyl, t-butyl, 2-pentyl, 3-pentyl, 2-methylbutyl, 3-methylbutyl, 1,1-dimethylpropyl, 1,2-dimethylpropyl and 2,2-dimethylpropyl groups. Of these, we prefer those straight or branched chain alkyl groups having from 1 to 4 carbon atoms, and more prefer those straight or branched chain alkyl groups having from 1 to 3 carbon atoms.

Where $R^2$ or $R^3$ represents a haloalkyl group having from 1 to 4 carbon atoms, this preferably has from 1 to 3 halogen atoms, which may be the same or different, and examples of such groups include the trifluoromethyl, trichloromethyl, difluoromethyl, dichloromethyl, dibromomethyl, 2,2,2-trichloroethyl, 2,2,2-trifluoroethyl, 2-fluoroethyl, 2,2-dibromoethyl, 3-chloropropyl, 3,3,3-trifluoropropyl and 4-fluorobutyl groups, of which we prefer alkyl groups having from 1 to 3 carbon atoms which are substituted by from 1 to 3 halogen atoms (and, where there are 2 or 3 halogen atoms, these are the same), more preferably the methyl or ethyl groups which are substituted by from 1 to 3 fluorine or chlorine atoms; the most preferred specific groups are the trifluoromethyl, trichloromethyl, difluoromethyl and 2-fluoroethyl groups, especially the trifluoromethyl group.

Where $R^2$ or $R^3$ represents a substituted alkyl group having from 1 to 12 carbon atoms, which group is substituted by at least one substituent selected from the group consisting of substituents A, defined and exemplified above, this may be any one of such groups exemplified above in relation to the similar groups which may be represented by $R^1$.

Where $R^4$ represents an alkoxy group having from 1 to 5 carbon atoms, this may be a straight or branched chain alkoxy group having from 1 to 5, preferably from 1 to 3, carbon atoms, and examples include the methoxy, ethoxy, propoxy, isopropoxy, butoxy, isobutoxy and pentyloxy groups. Of these, we prefer those alkoxy groups having from 1 to 3 carbon atoms, more preferably the methoxy and ethoxy groups.

Where $R^4$ represents an alkyl group having from 1 to 5 carbon atoms, this may be a straight or branched chain, and examples include the methyl, ethyl, propyl, butyl, pentyl, isopropyl, isobutyl, sec-butyl, t-butyl, 2-pentyl, 3-pentyl, 2-methylbutyl, 3-methylbutyl, 1,1-dimethylpropyl, 1,2-dimethylpropyl and 2,2-dimethylpropyl groups. Of these, we prefer those straight or branched chain alkyl groups having from 1 to 4 carbon atoms, and more prefer those straight or branched chain alkyl groups having from 1 to 3 carbon atoms.

Where $R^4$ represents an acyloxy group, this is an aliphatic, carboxylic acyloxy group, which may be a straight or branched chain group having from 1 to 6 carbon atoms. Examples include the formyloxy, acetoxy, propionyloxy, butyryloxy, isobutyryloxy, valeryloxy, isovaleryloxy, pivaloyloxy and hexanoyloxy groups. Of these, we prefer those acyloxy groups having 1 to 5 carbon atoms, and more prefer those acyloxy groups having from 1 to 3 carbon atoms. The most preferred acyloxy group is the acetoxy group.

Where $R^4$ represents an aralkyloxy group, the aralkyl part is as defined above, and the alkyl part may be as exemplified above in relation to the aralkyloxycarbonyl groups. Examples of unsubstituted aralkyloxy groups include the benzyloxy, phenethyloxy, 1-phenylethoxy, 3-phenylpropoxy and naphthylmethoxy groups. Examples of substituted aralkyloxy groups include any of the unsubstituted groups exemplified above but which is substituted by at least one of substituents B, and specific examples of such substituted groups include the o-, m- or p-fluorobenzyloxy, o-, m- or p-chlorobenzyloxy, o-, m- or p-methylbenzyloxy, o-, m- or p-methoxybenzyloxy, o-, m- or p-nitrobenzyloxy, o-, m- or p-trifluoromethylbenzyloxy, o-, m- or p-hydroxybenzyloxy, 3,5-di-t-butyl-4-hydroxybenzyloxy and 3,4,5-trimethoxybenzyloxy groups. Of these, we prefer those aralkyloxy groups which are unsubstituted or which have from 1 to 3 substituents selected from the group consisting of halogen atoms, alkyl groups having 1 to 4 carbon atoms, alkoxy groups having 1 to 3 carbon atoms, trifluoromethyl groups or hydroxy groups. The most preferred group is the benzyloxy group, which is preferably unsubstituted but which may have 1 or 2 substituents selected from the group consisting of fluorine atoms, chlorine atoms, methyl groups or methoxy groups.

Where $R^4$ represents an aryloxy group, the aryl part is as defined above. Examples of unsubstituted aryloxy groups include the phenyloxy and 1- and 2-naphthyloxy groups. Examples of substituted aryloxy groups include any of the unsubstituted groups exemplified above but which is substituted by at least one of substituents B, and specific examples of such substituted groups include the o-, m- or p-fluorophenyloxy, o-, m- or p-chlorophenyloxy, o-, m- or p-methylphenyloxy, o-, m- or p-methoxyphenyloxy, o-, m- or p-nitrophenyloxy, o-, m- or p-trifluoromethylphenyloxy, o-, m- or p-hydroxyphenyloxy, 3,5-di-t-butyl-4-hydroxyphenyloxy and 3,4,5-trimethoxyphenyloxy groups. Of these, we prefer those aryloxy groups which are unsubstituted or which have from 1 to 3 substituents selected from the group consisting of halogen atoms, alkyl groups having 1 to 4 carbon atoms, alkoxy groups having 1 to 3 carbon atoms, trifluoromethyl groups or hydroxy groups. The most preferred group is the phenyloxy group, which is preferably unsubstituted but which may have 1 or 2 substituents selected from the group consisting of fluorine atoms, chlorine atoms, methyl groups or methoxy groups.

Where $R^4$ represents an aryl group, the aryl part is as defined above. Examples of unsubstituted aryl groups include the phenyl and 1- and 2-naphthyl groups. Examples of substituted aryl groups include any of the unsubstituted groups exemplified above but which is substituted by at least one of substituents B, and specific examples of such substituted groups include the o-, m- or p-fluorophenyl, o-, m- or p-chlorophenyl, o-, m- or p-methylphenyl, o-, m- or p-methoxyphenyl, o-, m- or p-nitrophenyl, o-, m- or p-trifluoromethylphenyl, o-, m- or p-hydroxyphenyl, 3,5-di-t-butyl-4-hydroxyphenyl and 3,4,5-trimethoxyphenyl groups. Of these, we prefer those aryl groups which are unsubstituted or which have from 1 to 3 substituents selected from the group consisting of halogen atoms, alkyl groups having 1 to 4 carbon atoms, alkoxy groups having 1 to 3 carbon atoms, trifluoromethyl groups or hydroxy groups. The most preferred group is the phenyl group, which is preferably unsubstituted but which may have 1 or 2 substituents selected from the group consisting of fluorine atoms, chlorine atoms, methyl groups or methoxy groups.

Where $R^4$ represents a haloalkyl group having from 1 to 4 carbon atoms, this preferably has from 1 to 3 halogen atoms, which may be the same or different, and examples of such groups include the trifluoromethyl, trichloromethyl, difluoromethyl, dichloromethyl, dibromomethyl, 2,2,2-trichloroethyl, 2,2,2-trifluoroethyl, 2-fluoroethyl, 2,2-dibromoethyl, 3-chloropropyl, 3,3,3-trifluoropropyl and 4-fluorobutyl groups, of which we prefer alkyl groups having from 1 to 3 carbon atoms which are substituted by from 1 to 3 halogen atoms (and, where there are 2 or 3 halogen atoms, these are the same), more preferably the methyl or ethyl groups which are substituted by from 1 to 3 fluorine or chlorine atoms; the most preferred specific groups are the trifluoromethyl, trichloromethyl, difluoromethyl and 2-fluoroethyl groups, especially the trifluoromethyl group.

Where $R^4$ or $R^5$ represents a halogen atom, this may be, for example, the fluorine, chlorine, bromine or iodine atom, preferably the fluorine, chlorine or bromine atom, more preferably the fluorine or chlorine atom.

Where $R^5$ represents an alkoxy group, this may be a straight or branched chain alkoxy group having from 1 to 5, preferably from 1 to 3, carbon atoms, and examples include the methoxy, ethoxy, propoxy, isopropoxy, butoxy, isobutoxy and pentyloxy groups. Of these, we prefer those alkoxy groups having from 1 to 3 carbon atoms, more preferably the methoxy group.

Where $R^5$ represents an alkyl group having from 1 to 5 carbon atoms, this may be a straight or branched chain, and examples include the methyl, ethyl, propyl, butyl, pentyl, isopropyl, isobutyl, sec-butyl, t-butyl, 2-pentyl, 3-pentyl, 2-methylbutyl, 3-methylbutyl, 1,1-dimethylpropyl, 1,2-dimethylpropyl and 2,2-dimethylpropyl groups. Of these, we prefer those straight or branched chain alkyl groups having from 1 to 4 carbon atoms, and more prefer those straight or branched chain alkyl groups having from 1 to 3 carbon atoms.

Where $R^6$ represents a halogen atom, this may be, for example, the fluorine, chlorine, bromine or iodine atom, preferably the fluorine, chlorine or bromine atom, more preferably the fluorine or chlorine atom.

Where $R^6$ represents an alkoxy group, this may be a straight or branched chain alkoxy group having from 1 to 5, preferably from 1 to 3, carbon atoms, and examples include the methoxy, ethoxy, propoxy, isopropoxy, butoxy, isobutoxy and pentyloxy groups. Of these, we prefer those alkoxy groups having from 1 to 3 carbon atoms, more preferably the methoxy group.

Where R 6 represents an alkyl group having from 1 to 5 carbon atoms, this may be a straight or branched chain, and examples include the methyl, ethyl, propyl, butyl, pentyl, isopropyl, isobutyl, sec-butyl, t-butyl, 2-pentyl, 3-pentyl, 2-methylbutyl, 3-methylbutyl, 1,1-dimethylpropyl, 1,2-dimethylpropyl and 2,2-dimethylpropyl groups. Of these, we prefer those straight or branched chain alkyl groups having from 1 to 4 carbon atoms, and more prefer those straight or branched chain alkyl groups having from 1 to 3 carbon atoms. The most preferred alkyl group is the methyl group.

A preferred class of compounds of the present invention is those compounds of formula (I) and salts thereof in which:

$R^0$ represents a hydrogen atom, a methyl group or a hydroxymethyl group;

$R^1$ represents a substituted alkyl group having from 1 to 12 carbon atoms and substituted by at least 1 and no more than 8 substituents selected from the group consisting of substituents $A^1$, defined below;

$R^2$ and $R^3$ are the same or different and each represents a hydrogen atom, a fluorine atom, a chlorine atom, a bromine atom, a hydroxy group, a methoxy group, an ethoxy group, a carboxy group, an alkoxycarbonyl group having from 2 to 7 carbon atoms, an alkyl group having from 1 to 5 carbon atoms, a nitro group, a trifluoromethyl group or a substituted alkyl group having from 1 to 12 carbon atoms and substituted by at least 1 and no more than 8 substituents selected from the group consisting of substituents $A^1$, defined below;

X represents an oxygen or sulfur atom;

Ar represents a group of formula (II) or (III), defined above;

$R^4$ represents a hydrogen atom, a fluorine atom, a chlorine atom, a bromine atom, a hydroxy group, a hydroxymethyl group, a methoxy group, an ethoxy group, an alkyl group having from 1 to 5 carbon atoms, an acetoxy group, a nitro group, a cyano group, a benzyloxy group, a phenoxy group, a phenyl group or a trifluoromethyl group;

$R^5$ represents a hydrogen atom, a fluorine atom, a chlorine atom, a bromine atom, a hydroxy group, a methoxy group, an alkyl group having from 1 to 5 carbon atoms or a nitro group; and $R^6$ represents a hydrogen atom, a fluorine atom, a chlorine atom, a hydroxy group, a methoxy group or a methyl group; and said substituents $A^1$ are selected from the group consisting of carboxy groups, alkoxycarbonyl groups having from 2 to 7 carbon atoms, aryloxycarbonyl groups in which the aryl part is as defined above, aralkyloxycarbonyl groups in which the aralkyl part is as defined above, mono- and di-alkylcarbamoyl groups having from 2 to 7 carbon atoms, carbamoyl groups, hydroxycarbamoyl groups, hydroxy groups, aliphatic carboxylic acyloxy groups having from 1 to 6 carbon atoms and 2,4-dioxothiazolidin-5-yl groups.

More preferred compounds of the present invention are those compounds of formula (I) in which:

$R^0$ represents a hydrogen atom or a methyl group;

$R^1$ represents a substituted alkyl group which has from 1 to 12 carbon atoms and which is substituted by at least 1 and no more than 6 substituents selected from the group consisting of substituents $A^2$, defined below;

$R^2$ represents a hydrogen atom, a fluorine atom, a chlorine atom, a bromine atom, a hydroxy group, a methoxy group, an ethoxy group, an alkyl group having from 1 to 4 carbon atoms, a nitro group, or a substituted alkyl group which has from 1 to 4 carbon atoms and which has from 1 to 3 substituents selected from the group consisting of carboxy groups, alkoxycarbonyl groups having 2 or 3 carbon atoms, methylcarbamoyl groups, carbamoyl groups, hydroxy groups and aliphatic carboxylic acyloxy groups having from 2 to 5 carbon atoms;

$R^3$ represents a hydrogen atom, a fluorine atom, a chlorine atom, a hydroxy group, a methoxy group, a methyl group or a t-butyl group;

X represents an oxygen or sulfur atom; and

Ar represents a group of formula (II) or (III), defined above;

$R^4$ represents a hydrogen atom, a fluorine atom, a chlorine atom, a bromine atom, a hydroxy group, a hydroxymethyl group, a methoxy group, an ethoxy group, an alkyl group having from 1 to 4 carbon atoms, an acetoxy group, a nitro group, a benzyloxy group, a phenoxy group, a phenyl group or a trifluoromethyl group;

$R^5$ represents a hydrogen atom, a fluorine atom, a chlorine atom, a bromine atom, a hydroxy group, a methoxy group or an alkyl group having from 1 to 4 carbon atoms;

$R^6$ represents a hydrogen atom, a fluorine atom, a chlorine atom, a hydroxy group, a methoxy group or a methyl group; and said substituents A2 are selected from the group consisting of:
carboxy groups,
alkoxycarbonyl groups having from 2 to 5 carbon atoms,
phenoxycarbonyl groups, which are unsubstituted or which are substituted by from 1 to 3 substituents selected from the group consisting of halogen atoms, alkyl groups having from 1 to 4 carbon atoms, alkoxy groups having from 1 to 3 carbon atoms, nitro groups, trifluoromethyl groups and hydroxy groups,
benzyloxycarbonyl and phenethyloxycarbonyl groups, which are unsubstituted or which are substituted by from 1 to 3 substituents selected from the group consisting of halogen atoms, alkyl groups having from 1 to 4 carbon atoms, alkoxy groups having from 1 to 3 carbon atoms, nitro groups, trifluoromethyl groups and hydroxy groups,
monoalkylcarbamoyl groups having from 2 to 4 carbon atoms,
carbamoyl groups,
hydroxycarbamoyl groups,
hydroxy groups,
aliphatic carboxylic acyloxy groups having from 1 to 6 carbon atoms, and
2,4-dioxothiazolidin-5-yl groups.

A still more preferred class of compounds of the present invention are those compounds of formula (I) and salts thereof, in which:

$R^0$ represents a hydrogen atom or a methyl group;

$R^1$ represents a substituted alkyl group which has from 1 to 6 carbon atoms and which is substituted by at least 1 and no more than 6 substituents selected from the group consisting of substituents $A^3$, defined below;

$R^2$ represents a hydrogen atom, a fluorine atom, a chlorine atom, a bromine atom, a hydroxy group, a methoxy group, an ethoxy group, an alkyl group having from 1 to 4 carbon atoms, or a substituted alkyl group which has from 1 to 3 carbon atoms and which is substituted by from 1 to 3 substituents selected from the group consisting of carboxy groups, alkoxycarbonyl groups having 2 or 3 carbon atoms, methylcarbamoyl groups, carbamoyl groups, hydroxy groups and aliphatic carboxylic acyloxy groups having from 2 to 5 carbon atoms;

$R^3$ represents a hydrogen atom, a fluorine atom, a chlorine atom, a hydroxy group, a methoxy group, a methyl group or a t-butyl group;

X represents an oxygen or sulfur atom;

Ar represents a group of formula (II) or (III), defined above;

$R^4$ represents a hydrogen atom, a fluorine atom, a chlorine atom, a bromine atom, a hydroxy group, a hydroxymethyl group, a methoxy group, an ethoxy group, an alkyl group having from 1 to 4 carbon atoms, an acetoxy group, a nitro group, a benzyloxy group, a phenoxy group, a phenyl group or a trifluoromethyl group;

$R^5$ represents a hydrogen atom, a fluorine atom, a chlorine atom, a bromine atom, a hydroxy group, a methoxy group or an alkyl group having from 1 to 4 carbon atoms;

$R^6$ represents a hydrogen atom, a fluorine atom, a chlorine atom, a hydroxy group, a methoxy group or a methyl group; and said substituents $A^3$ are selected from the group consisting of:
carboxy groups,
alkoxycarbonyl groups having from 2 to 5 carbon atoms,
benzyloxycarbonyl and phenethyloxycarbonyl groups which are unsubstituted or which are substituted by from 1 to 3 substituents selected from the group consisting of halogen atoms, alkyl groups having from 1 to 3 carbon atoms, alkoxy groups having from 1 to 3 carbon atoms, nitro groups, trifluoromethyl groups and hydroxy groups,
monoalkylcarbamoyl groups having from 2 to 4 carbon atoms,
carbamoyl groups,
hydroxycarbamoyl groups,
hydroxy groups
aliphatic carboxylic acyloxy groups having from 1 to 6 carbon atoms, and
2,4-dioxothiazolidin-5-yl groups.

Still more preferred compounds of the present invention are those compounds of formula (I) in which:

$R^0$ represents a hydrogen atom or a methyl group;

$R^1$ represents a substituted alkyl group which has from 1 to 3 carbon atoms and which is substituted by at least 1 and no more than 4 substituents selected from the group consisting of substituents $A^4$, defined below;

$R^2$ represents a hydrogen atom, a fluorine atom, a chlorine atom, a hydroxy group, a methoxy group, an alkyl group having from 1 to 4 carbon atoms or a hydroxymethyl group;

$R^3$ represents a hydrogen atom, a chlorine atom, a hydroxy group, a methoxy group or a methyl group;

X represents an oxygen atom;

Ar represents a group of formula (II) or (III), defined above;

$R^4$ represents a hydrogen atom, a fluorine atom, a chlorine atom, a bromine atom, a hydroxy group, a hydroxymethyl group, a methoxy group, an ethoxy group, an alkyl group having from 1 to 4 carbon atoms, an acetoxy group, a nitro group, a benzyloxy group, a phenoxy group, a phenyl group or a trifluoromethyl group;

$R^5$ represents a hydrogen atom, a fluorine atom, a chlorine atom, a bromine atom, a hydroxy group, a methoxy group or an alkyl group having from 1 to 4 carbon atoms;

$R^6$ represents a hydrogen atom, a fluorine atom, a chlorine atom, a hydroxy group, a methoxy group or a methyl group; and said substituents $A^4$ are selected from the group consisting of:
carboxy groups,
alkoxycarbonyl group having from 2 to 5 carbon atoms, benzyloxycarbonyl groups which are unsubstituted or which are substituted by from 1 to 3 substituents selected from the group consisting of alkyl groups having from 1 to 4 carbon atoms and hydroxy groups, monoalkylcarbamoyl groups having from 2 to 4 carbon atoms,
carbamoyl groups,
hydroxycarbamoyl groups,
hydroxy groups,
aliphatic carboxylic acyloxy groups having from 1 to 6 carbon atoms, and
2,4-dioxothiazolidin-5-yl groups;

Still more preferred compounds of the present invention are those compounds of formula (I) in which:

$R^0$ represents a hydrogen atom or a methyl group;
$R^1$ represents a substituted alkyl group which has from 1 to 3 carbon atoms and which is substituted by at least 1 and no more than 4 substituents selected from the group consisting of substituents $A^5$, defined below;
$R^2$ represents a hydrogen atom, a chlorine atom, a hydroxy group, a methoxy group, a methyl group or a hydroxymethyl group;
$R^3$ represents a hydrogen atom or a methyl group;
X represents an oxygen atom;
Ar represents a group of formula (II) or (III), defined above;
$R^4$ represents a hydrogen atom, a fluorine atom, a chlorine atom, a bromine atom, a hydroxy group, a hydroxymethyl group, a methoxy group, an ethoxy group, an alkyl group having from 1 to 4 carbon atoms, an acetoxy group, a nitro group, a benzyloxy group, a phenoxy group, a phenyl group or a trifluoromethyl group;
$R^5$ represents a hydrogen atom, a fluorine atom, a chlorine atom, a bromine atom, a hydroxy group, a methoxy group or an alkyl group having from 1 to 4 carbon atoms;
$R^6$ represents a hydrogen atom, a hydroxy group, a methoxy group or a methyl group; and
said substituents $A^5$ are selected from the group consisting of:
carboxy groups,
alkoxycarbonyl group having from 2 to 4 carbon atoms, benzyloxycarbonyl groups which are unsubstituted or which are substituted by from 1 to 3 substituents selected from the group consisting of alkyl groups having from 1 to 4 carbon atoms and hydroxy groups, monoalkylcarbamoyl groups having 2 or 3 carbon atoms, carbamoyl groups,
hydroxycarbamoyl groups,
hydroxy groups,
aliphatic carboxylic acyloxy groups having from 2 to 5 carbon atoms, and
2,4-dioxothiazolidin-5-yl groups.

Still more preferred compounds of the present invention are those compounds of formula (I) in which:

$R^0$ represents a hydrogen atom;
$R^1$ represents a substituted alkyl group which has from 1 to 3 carbon atoms and which is substituted by at least 1 and no more than 4 substituents selected from the group consisting of substituents $A^6$, defined below;
$R^2$ represents a hydrogen atom, a chlorine atom, a hydroxy group, a methoxy group, a methyl group or a hydroxymethyl group;
$R^3$ represents a hydrogen atom;
X represents an oxygen atom;
Ar represents a group of formula (II) or (III), defined above;
$R^4$ represents a hydrogen atom, a fluorine atom, a chlorine atom, a bromine atom, a methoxy group, an alkyl group having from 1 to 4 carbon atoms, a phenoxy group or a trifluoromethyl group;
$R^5$ represents a hydrogen atom, a chlorine atom, a methoxy group or an alkyl group having from 1 to 4 carbon atoms;
$R^6$ represents a hydrogen atom, a hydroxy group or a methoxy group; and
said substituents $A^6$ are selected from the group consisting of:
carboxy groups,
alkoxycarbonyl groups having from 2 to 4 carbon atoms,
monoalkylcarbamoyl groups having 2 or 3 carbon atoms,
carbamoyl groups,
hydroxycarbamoyl groups,
hydroxy groups,
aliphatic carboxylic acyloxy groups having from 2 to 5 carbon atoms, and
2,4-dioxothiazolidin-5-yl groups;

Still more preferred compounds of the present invention are those compounds of formula (I) in which:

$R^0$ represents a hydrogen atom;
$R^1$ represents an alkyl group which has from 1 to 3 carbon atoms and which is substituted by 1 or 2 substituents selected from the group consisting of substituents $A^7$, defined below;
$R^2$ represents a hydrogen atom, a chlorine atom, a hydroxy group or a hydroxymethyl group;
$R^3$ represents a hydrogen atom;
X represents an oxygen atom;
Ar represents a phenyl, 2-chlorophenyl, 3-chlorophenyl, 4-chlorophenyl, 3-bromophenyl, 3-fluorophenyl, 3-phenoxyphenyl, 3-methylphenyl, 3-methoxyphenyl, 3,5-dichlorophenyl, 3,5-di-t-butyl-4-hydroxyphenyl, 3,4,5-trimethoxyphenyl, 3-trifluoromethylphenyl, 3-chloro-4-fluorophenyl, 1-naphthyl or 2-naphthyl group; and
said substituents $A^7$ are selected from the group consisting of alkoxycarbonyl group having from 2 to 4 carbon atoms, hydroxy groups, aliphatic carboxylic acyloxy groups having from 2 to 5 carbon atoms and 2,4-dioxothiazolidin-5-yl groups.

Still more preferred compounds of the present invention are those compounds of formula (I) in which:

$R^0$ represents a hydrogen atom;
$R^1$ represents a methoxycarbonylmethyl, ethoxycarbonylmethyl, 2-methoxycarbonylethyl, bis(methoxycarbonyl)methyl, hydroxymethyl, 2-hydroxyethyl, 1,2-dihydroxyethyl, 1,3-dihydroxy-2-propyl, 1-methoxycarbonyl-1-hydroxymethyl, 2-methoxycarbonyl-2-hydroxyethyl, 2-acetyloxyethyl or 2,4-dioxothiazolidin-5-ylmethyl group;

R² represents a hydrogen atom, a chlorine atom or a hydroxymethyl group;

R³ represents a hydrogen atom;

X represents an oxygen atom; and

Ar represents a phenyl, 2-chlorophenyl, 3-chlorophenyl, 4-chlorophenyl, 3-bromophenyl, 3-fluorophenyl, 3-methylphenyl, 3-methoxyphenyl, 3,5-di-t-butyl-4-hydroxyphenyl, 3-trifluoromethylphenyl, 3-chloro-4-fluorophenyl or 2-naphthyl group.

The most preferred compounds of the present invention are those compounds of formula (I) in which:

R⁰ represents a hydrogen atom;

R¹ represents a methoxycarbonylmethyl, ethoxycarbonylmethyl, 2-methoxycarbonylethyl, bis(methoxycarbonyl)methyl, hydroxymethyl, 2-hydroxyethyl, 2-methoxycarbonyl-2-hydroxyethyl or 2,4-dioxothiazolidin-5-ylmethyl group;

R² represents a hydrogen atom;

R³ represents a hydrogen atom;

X represents an oxygen atom; and

Ar represents a phenyl, 3-chlorophenyl, 3-bromophenyl, 3-trifluoromethylphenyl, 3-chloro-4-fluorophenyl or 2-naphthyl group.

The compounds of the present invention can exist in the form of various stereoisomers, as shown in formula (IV):

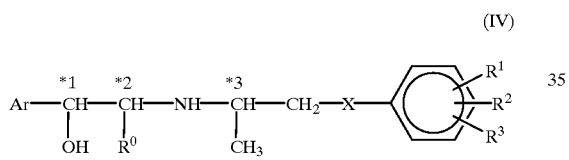

in which R⁰, R¹, R², R³, X and Ar are as defined above. Where R⁰ represents a hydrogen atom, there are at least two asymmetric carbon atoms (marked *1 and *3) and, where R⁰ represents a methyl or hydroxymethyl group, there are at least three asymmetric carbon atoms (marked *1, *2 and *3). Although these are all represented herein by a single molecular formula, the present invention includes both the individual, isolated isomers and mixtures (where the amounts of isomers may be equal or different), including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

Of the compounds of the invention, we prefer those isomers in which the asymmetric carbon atoms marked by *1 and *3 are in the R-configuration.

Examples of specific compounds of the invention are those compounds of formula (I-1), in which the various substituent groups are as defined in Table 1, and formula (I-2), in which the various substituent groups are as defined in Tables 2 to 8.

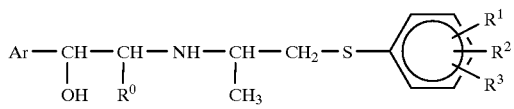

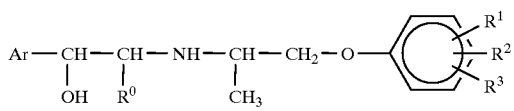

In the Tables, the following abbreviations are used:

| | |
|---|---|
| Ac | acetyl |
| Boc | butoxycarbonyl |
| iBoc | isobutoxycarbonyl |
| sBoc | sec-butoxycarbonyl |
| tBoc | t-butoxycarbonyl |
| Bu | butyl |
| tBu | t-butyl |
| Byr | butyryl |
| iByr | isobutyryl |
| Bzc | benzyloxycarbonyl |
| Et | ethyl |
| Etc | ethoxycarbonyl |
| Me | methyl |
| Mec | methoxycarbonyl |
| Np | naphthyl |
| Ph | phenyl |
| Piv | pivaloyl |
| Pr | propyl |
| iPr | isopropyl |
| iPrc | isopropoxycarbonyl |
| Prn | propionyl |
| Tfm | trifluoromethyl |
| Thiz | thiazolidin-5-yl |
| Val | valeryl |
| iVal | isovaleryl |

TABLE 1

| Cpd. No. | Ar | R⁰ | R¹ | R² | R³ |
|---|---|---|---|---|---|
| 1-1 | Ph | —CH₂OH | 4-HOOCCH₂— | H | H |
| 1-2 | 3-ClPh | Me | 4-MecCH₂— | H | H |
| 1-3 | 3-ClPh | H | 4-MecCH₂— | H | H |
| 1-4 | 3-ClPh | H | 4-EtcCH₂— | H | H |
| 1-5 | 3-ClPh | H | 4-Mec₂CH— | H | H |
| 1-6 | 3-ClPh | H | 4-BzcCH₂— | H | H |
| 1-7 | 3-ClPh | H | 4-(2,2-diEtcEt)— | H | H |
| 1-8 | 3-ClPh | H | 4-HOCH₂— | H | H |
| 1-9 | 3-ClPh | H | 4-HOCH₂— | 3-HOCH₂— | H |
| 1-10 | 3-ClPh | H | 4-(2-HOEt)— | H | H |
| 1-11 | 3-ClPh | H | 4-(3-HOPr)— | H | H |
| 1-12 | 3-ClPh | H | 4-(2-AcOEt)— | H | H |
| 1-13 | 3-ClPh | H | 4-(HOCH₂)₂CH— | H | H |
| 1-14 | 3-FPh | H | 4-MecCH₂— | H | H |
| 1-15 | 3-TfmPh | H | 4-MecCH₂— | H | H |
| 1-16 | 3-BrPh | H | 4-MecCH₂— | H | H |
| 1-17 | 3,5-ditBu-4-HOPh | H | 4-MecCH₂— | H | H |
| 1-18 | 3-Cl-4-FPh | H | 4-(Mec)(HO)CH— | H | H |
| 1-19 | 3,5-diClPh | H | 4-(Mec-HOCH)CH₂— | H | H |
| 1-20 | 2-Np | H | 4-MecCH₂— | H | H |
| 1-21 | 3-ClPh | H | 4-(2-PivOEt)— | H | H |

TABLE 2

| Cpd. No. | Ar | R⁰ | R¹ | R² | R³ |
|---|---|---|---|---|---|
| 2-1 | 3-ClPh | H | 4-HOOCCH₂— | H | H |
| 2-2 | 3-Cl-4-FPh | H | 4-HOOCCH₂— | H | H |
| 2-3 | 3-ClPh | H | 4-(2-HOOCEt)— | H | H |
| 2-4 | 3-FPh | H | 4-HOOCCH₂— | H | H |
| 2-5 | 3-BrPh | H | 4-(HOOC)—(HO)CH— | H | H |
| 2-6 | 3-TfmPh | H | 4-HOOCCH₂— | H | H |
| 2-7 | 3-MePh | H | 4-HOOCCH₂— | H | H |
| 2-8 | 4-ClPh | H | 4-HOOCCH₂— | H | H |
| 2-9 | 2-ClPh | H | 4-HOOCCH₂— | H | H |
| 2-10 | 2-Np | H | 4-HOOCCH₂— | H | H |
| 2-11 | 3-ClPh | H | 4-(HOOC)—(HO)CH— | H | H |
| 2-12 | 3-ClPh | H | 4-HOOCCH₂— | 2-Cl | H |

TABLE 3

| Cpd. No. | Ar | R⁰ | R¹ | R² | R³ |
|---|---|---|---|---|---|
| 3-1 | 3-ClPh | H | 4-MecCH₂— | H | H |
| 3-2 | 3-ClPh | H | 3-MecCH₂— | H | H |
| 3-3 | 3-ClPh | H | 2-MecCH₂— | H | H |
| 3-4 | 3-ClPh | H | 4-(2-MecEt)— | H | H |
| 3-5 | Ph | H | 4-(2-MecEt)— | H | H |
| 3-6 | Ph | —CH₂OH | 4-MecCH₂— | H | H |
| 3-7 | 2-Np | H | 4-MecCH₂— | H | H |
| 3-8 | 1-Np | H | 4-MecCH₂— | H | H |
| 3-9 | Ph | Me | 4-MecCH₂— | H | H |
| 3-10 | 3-ClPh | H | 3-MecCH₂— | 4-MecCH₂— | H |
| 3-11 | 2-ClPh | H | 4-MecCH₂— | H | H |
| 3-12 | 4-ClPh | H | 4-MecCH₂— | H | H |
| 3-13 | 3-FPh | H | 4-MecCH₂— | H | H |
| 3-14 | 3-BrPh | H | 4-MecCH₂— | H | H |
| 3-15 | 3,5-diClPh | H | 4-MecCH₂— | H | H |
| 3-16 | 3,4,5-triMeOPh | H | 4-MecCH₂— | H | H |
| 3-17 | 3,4,5-triMeOPh | H | 4-(2,2-diEtcEt)— | H | H |
| 3-18 | 3-ClPh | H | 4-Mec₂CH— | H | H |
| 3-19 | 3-ClPh | H | 4-EtcCH₂— | H | H |
| 3-20 | 3-ClPh | H | 4-iPrcCH₂— | H | H |
| 3-21 | 3-ClPh | H | 4-BocCH₂ | H | H |
| 3-22 | 3-ClPh | H | 4-[1,1,2,2-(Etc)₄Et]— | H | H |
| 3-23 | 3-ClPh | H | 4-MecCH₂— | 2-HO | H |
| 3-24 | 3-ClPh | H | 4-MecCH₂— | 2-HO | 2-HO |
| 3-25 | 3-ClPh | H | 3-MecCH₂— | 4-HO | H |
| 3-26 | 3-PhOPh | H | 4-MecCH₂— | H | H |
| 3-27 | 3,5-ditBu-4-HOPh | H | 4-MecCH₂— | H | H |
| 3-28 | 3-ClPh | H | 4-MecCH₂— | 2-Cl | H |
| 3-29 | Ph | H | 4-MecCH₂— | H | H |
| 3-30 | 3,5-ditBu-4-HOPh | H | 5-EtcCH₂— | 2-HO | H |
| 3-31 | 3-ClPh | H | 2-MecCH₂— | 5-MecCH₂— | 4-HO |
| 3-32 | 2,5-diClPh | H | 4-MecCH₂— | 2-HO | H |
| 3-33 | 3,5-ditBu-4-HOPh | H | 4-MecCH₂— | 2-F | H |
| 3-34 | 3-ClPh | H | 4-MecCH₂— | 2-MeO | H |
| 3-35 | 3,5-ditBu-4-HOPh | H | 5-MecCH₂— | 2-MeO | H |
| 3-36 | 3,5-diMe-4-HOPh | H | 5-BocCH₂— | 2-EtO | H |
| 3-37 | 3-ClPh | H | 4-MecCH₂— | 2-MeO | 6-MeO |
| 3-38 | 3-ClPh | H | 4-iPrcCH₂— | 2-EtO | H |
| 3-39 | 3-ClPh | H | 4-EtcCH₂— | 2-Me | H |
| 3-40 | 2-F-4-BrPh | H | 4-Mec₂CH— | H | H |
| 3-41 | 3-Cl-4-FPh | H | 4-MecCH₂— | H | H |
| 3-42 | 3-TfmPh | H | 4-Bzc₂CH— | H | H |
| 3-43 | 3,4-diClPh | H | 4-[3,5-ditBu-4-HOBzc)CH₂— | H | H |
| 3-44 | 3-TfmPh | H | 4-EtcCH₂— | 3-Etc-CH₂— | H |

TABLE 3-continued

| Cpd. No. | Ar | R⁰ | R¹ | R² | R³ |
|---|---|---|---|---|---|
| 3-45 | 3-ClPh | H | 4-iBocCH₂— | H | H |
| 3-46 | 3-ClPh | H | 4-sBocCH₂— | H | H |
| 3-47 | 3-ClPh | H | 4-tBocCH₂— | H | H |
| 3-48 | 3-ClPh | H | 4-iPrc₂CH— | H | H |
| 3-49 | 3-ClPh | H | 4-(2,2-diMecEt)— | H | H |
| 3-50 | 3-ClPh | H | 4-(Mec)(Me)CH— | H | H |
| 3-51 | 3-BrPh | H | 4-[1,1,2,2-(Etc)₄Et]— | H | H |
| 3-52 | 3-ClPh | H | 4-PhOCOCH₂— | H | H |
| 3-53 | Ph | Me | 4-(3-F-PhOCO)CH₂— | H | H |
| 3-54 | 3-ClPh | H | 4-(PhOCO)₂CH— | H | H |
| 3-55 | 3-ClPh | H | 4-(4-MeOBzc)₂CH— | H | H |
| 3-56 | 2-Np | H | 4-[(2-PhEtc)CH₂]— | H | H |
| 3-57 | 3-Cl-Ph | H | 4-(3,5-ditBu-4-HOBzc)CH₂— | H | H |
| 3-58 | 3-ClPh | H | 4-Bzc₂CH— | H | H |
| 3-59 | 3-FPh | H | 4-(2,2-diBzcEt)— | H | H |
| 3-60 | Ph | H | 3-MecCH₂— | 4-HO | H |
| 3-61 | 3-MePh | H | 4-MecCH₂— | H | H |
| 3-62 | 3-MeOPh | H | 4-MecCH₂— | H | H |
| 3-63 | 3,5-diClPh | H | 4-MecCH₂— | H | H |
| 3-64 | 2-Np | H | 4-Mec₂CH— | H | H |
| 3-65 | 3-TfmPh | H | 3-MecCH₂— | 4-HO | H |
| 3-66 | 3-TfmPh | H | 3-MecCH₂— | H | H |

TABLE 4

| Cpd. No. | Ar | R⁰ | R¹ | R² | R³ |
|---|---|---|---|---|---|
| 4-1 | 3-ClPh | H | 4-HOHNCOCH₂— | H | H |
| 4-2 | 3-ClPh | H | 4-H₂NCOCH₂— | H | H |
| 4-3 | 3-ClPh | H | 4-MeHNCOCH₂— | H | H |
| 4-4 | 3-ClPh | H | 4-BuHNCOCH₂— | H | H |
| 4-5 | 3-ClPh | H | 4-Et₂NCOCH₂— | H | H |
| 4-6 | 3-ClPh | H | 4-H₂NCOCH₂— | 2-Cl | H |
| 4-7 | 3-ClPh | H | 4-(2-H₂NCOEt)— | H | H |
| 4-8 | 3-ClPh | H | 4-EtHNCOCH₂— | H | H |
| 4-9 | 2-Np | H | 4-PrHNCOCH₂— | H | H |
| 4-10 | 3-BrPh | H | 4-iPrHNCOCH₂— | H | H |
| 4-11 | 3-ClPh | H | 4-(H₂NCO)₂CH— | H | H |
| 4-12 | 3-ClPh | H | 4-[2,2-di(H₂NCO)Et]— | H | H |
| 4-13 | 2-Np | H | 4-(H₂NCO)₂CH— | H | H |
| 4-14 | 3,5-ditBu-4-HOPh | H | 4-(H₂NCO)₂CH— | H | H |
| 4-15 | 3-ClPh | H | 4-HOHNCOCH₂— | 2-Cl | H |
| 4-16 | 3-FPh | H | 4-iPrHNCOCH₂— | H | H |
| 4-17 | 3-TfmPh | H | 4-H₂NCOCH₂— | H | H |
| 4-18 | 3-MeOPh | H | 4-H₂NCOCH₂— | H | H |

TABLE 5

| Cpd. No. | Ar | R⁰ | R¹ | R² | R³ |
|---|---|---|---|---|---|
| 5-1 | 3-ClPh | H | 4-(2,4-dioxoThiz)CH₂— | H | H |
| 5-2 | 2-Np | H | 4-(2,4-dioxoThiz)CH₂— | H | H |
| 5-3 | 3-TfmPh | H | 4-(2,4-dioxoThiz)CH₂— | H | H |
| 5-4 | 3-Cl-4-FPh | H | 4-(2,4-dioxoThiz)CH₂— | H | H |
| 5-5 | 3,5-ditBu-4-HOPh | H | 4-(2,4-dioxoThiz)CH₂— | H | H |
| 5-6 | 3-MeOPh | H | 4-(2,4-dioxoThiz)CH₂— | H | H |
| 5-7 | Ph | Me | 4-(2,4-dioxoThiz)CH₂— | H | H |
| 5-8 | Ph | —CH₂OH | 4-(2,4-dioxoThiz)CH₂— | H | H |

TABLE 6

| Cpd. No. | Ar | R⁰ | R¹ | R² | R³ |
|---|---|---|---|---|---|
| 6-1 | 3-ClPh | H | 4-(Mec)(HO)CH— | H | H |
| 6-2 | 3-ClPh | H | 4-(2-Mec-2-HOEt)— | H | H |
| 6-3 | 3,5-diMeOPh | H | 4-(H₂NCO)(HO)CH— | H | H |
| 6-4 | 3-F-4-MeOPh | H | 4-(3-F-PhOCO)(HO)CH— | H | H |
| 6-5 | 3,5-diMe-4-HOPh | H | 4-(Mec)(HO)CH— | H | H |
| 6-6 | 1-HO-4-Br-2-Np— | H | 4-(2-Etc-1-HOEt)— | H | H |
| 6-7 | 3-ClPh | H | 4-(2-Etc-1-HOEt)— | H | H |
| 6-7 | 3-ClPh | H | 4-(HOOC)(HO)CH— | H | H |
| 6-8 | 3-ClPh | H | 4-(3-HOOC-2-HOPr)— | H | H |
| 6-9 | 3-ClPh | H | 4-(H₂NCO)(HO)CH— | H | H |
| 6-10 | 2-NP | H | 4-(iPrc)(HO)CH— | H | H |
| 6-11 | 3-ClPh | H | 4-(Etc)(HO)CH— | H | H |
| 6-12 | 3-ClPh | H | 4-(2-Etc-1-HOEt)— | H | H |
| 6-13 | 3-ClPh | H | 4-(4-TfmPhOCO)(HO)CH— | H | H |
| 6-14 | 3-FPh | H | 4-(PhOCO)(HO)CH— | H | H |
| 6-15 | 3-ClPh | H | 4-(PhOCO)(HO)CHCH₂— | H | H |
| 6-16 | 3-ClPh | H | 4-(2-PhOCO-2-AcOEt)— | H | H |
| 6-17 | 3-ClPh | H | 4-(2-H₂NCO-2-HOEt)— | H | H |
| 6-18 | 3,4,5-triMeO-Ph | H | 4-(2-MeHNCO-2-HOEt)— | H | H |
| 6-19 | 3-ClPh | H | 4-(2-H₂NCO-2-AcOEt)— | H | H |
| 6-20 | 3-TfmPh | H | 4-(Mec)(HO)CH— | H | H |

TABLE 7

| Cpd. No. | Ar | R⁰ | R¹ | R² | R³ |
|---|---|---|---|---|---|
| 7-1 | Ph | H | 4-(2-HOEt)— | H | H |
| 7-2 | 3-ClPh | H | 4-HOCH₂— | H | H |
| 7-3 | 3-ClPh | H | 4-(2-HOEt)— | H | H |
| 7-4 | 3-ClPh | H | 4-(3-HOPr)— | H | H |
| 7-5 | 3-ClPh | H | 4-(1,2-diHOEt)— | H | H |
| 7-6 | 3-ClPh | H | 4-(2,3-diHOPr)— | H | H |
| 7-7 | 3-ClPh | H | 4-HOCH₂— | 3-HOCH₂— | H |
| 7-8 | 3-ClPh | H | 4-HOCH₂— | 2-HOCH₂— | H |
| 7-9 | 3-ClPh | H | 4-[1,1,2,2-tetra-(HOCH₂)Et]— | H | H |
| 7-10 | 3-ClPh | H | 4-(HOCH₂)₂CH— | H | H |
| 7-11 | 3-ClPh | H | 4-[2,2-di-(HOCH₂)Et]— | H | H |
| 7-12 | 3-ClPh | H | 4-(1-HOEt)— | H | H |
| 7-13 | 3-ClPh | H | 4-(2-HOEt)— | 3-(2-HOEt)— | H |
| 7-14 | 3-ClPh | H | 4-HOCH₂— | 3-Tfm | H |
| 7-15 | 3-FPh | H | 4-(HOCH₂)₂CH— | H | H |
| 7-16 | 4-MePh | H | 4-(1,2-diHOEt)— | H | H |
| 7-17 | 2-Np | H | 4-(2-HOPr)— | H | H |
| 7-18 | 2-Np | H | 4-(1-HOEt)— | H | H |
| 7-19 | 4-MeONp | H | 4-(2,3-diHOPr)— | H | H |
| 7-20 | 3,5-ditBu-4-HOPh | H | 4-(2-HOEt)— | H | H |
| 7-21 | 3-ClPh | H | 4-(2-HOEt)— | 2-Cl | H |
| 7-22 | 3-ClPh | H | 4-(2-HOEt)— | 2-HO | H |
| 7-23 | 3-TfmPh | H | 4-(2-HOEt)— | H | H |
| 7-24 | 3-FPh | H | 4-(2-HOEt)— | H | H |
| 7-25 | 3-MePh | H | 4-(2-HOEt)— | H | H |
| 7-26 | 3-MeOPh | H | 4-(2-HOEt)— | H | H |
| 7-27 | 2-Np | H | 4-(2-HOEt)— | H | H |
| 7-28 | 3-Cl-4-FPh | H | 4-(2-HOEt)— | H | H |
| 7-29 | 3-BrPh | H | 4-(2-HOEt)— | H | H |
| 7-30 | 2-Np | H | 4-(HOCH₂)₂CH— | H | H |
| 7-31 | 1-Np | H | 4-(2-HOEt)— | H | H |
| 7-32 | 3,4,5-triMeO—Ph | H | 4-(2-HOEt)— | H | H |
| 7-33 | 3-ClPh | H | 4-HO | 3-(2-HOEt)— | H |
| 7-34 | 3-ClPh | H | 4-HOCH₂— | 2-Me | 6-Me |
| 7-35 | 3-ClPh | H | 4-(2-HOPr)— | H | H |
| 7-36 | 2-Np | H | 4-(1,2-diHOEt)— | H | H |
| 7-37 | 3-TfmPh | H | 4-(1,2-diHOEt)— | H | H |
| 7-38 | 3,5-ditBu-4-HOPh | H | 4-(1,2-diHOEt)— | H | H |
| 7-39 | 3,5-diClPh | H | 4-(1,2-diHOEt)— | H | H |
| 7-40 | 2-Np | H | 4-(2,3-diHOPr)— | H | H |
| 7-41 | 3,4-diClPh | H | 4-(2,3-diHOPr)— | H | H |
| 7-42 | 3-TfmPh | H | 4-(HOCH₂)₂CH— | H | H |
| 7-43 | Ph | Me | 4-(HOCH₂)₂CH— | H | H |
| 7-44 | 3,5-diClPh | H | 4-(HOCH₂)₂CH— | H | H |
| 7-45 | 3,4-diClPh | H | 4-(HOCH₂)₂CH— | H | H |
| 7-46 | 3,5-diMe-4-HOPh | H | 4-(HOCH₂)₂CH— | H | H |
| 7-47 | 3,4,5-triMeO—Ph | H | 4-(HOCH₂)₂CH— | H | H |
| 7-48 | 3-Cl-4-FPh | H | 4-(HOCH₂)₂CH— | H | H |
| 7-49 | 2-F-4-BrPh | H | 4-(HOCH₂)₂CH— | H | H |
| 7-50 | Ph | H | 4-(HOCH₂)₂CH— | H | H |
| 7-51 | 3-PhOPh | H | 4-(HOCH₂)₂CH— | H | H |
| 7-52 | 3,5-ditBu-4-HOPh | H | 4-(HOCH₂)₂CH— | H | H |
| 7-53 | 2-Np | H | 4-[2,2-di-(HOCH₂)Et]— | H | H |
| 7-54 | 3,4-diClPh | H | 4-[2,2-di-(HOCH₂)Et]— | H | H |
| 7-55 | 3,5-diClPh | H | 4-[2,2-di-(HOCH₂)Et]— | H | H |

TABLE 8

| Cpd. No. | Ar | R⁰ | R¹ | R² | R³ |
|---|---|---|---|---|---|
| 8-1 | 3-ClPh | H | 4-(2-AcOEt)— | H | H |
| 8-2 | 3-ClPh | H | 4-(2-PivOEt)— | H | H |
| 8-3 | 3-MeOPh | H | 4-(AcOCH₂)CH— | H | H |
| 8-4 | 3-ClPh | H | 4-AcOCH₂— | H | H |
| 8-5 | 3-FPh | H | 4-PrnOCH₂— | 2-Me | 6-Me |
| 8-6 | 3,4,5-triMeO—Ph | H | 4-ByrOCH₂— | H | H |
| 8-7 | 3-ClPh | H | 4-iByrOCH₂— | H | H |
| 8-8 | 3-ClPh | H | 4-(2-PrnOEt)— | H | H |
| 8-9 | 3-ClPh | H | 4-(2-ByrOEt)— | H | H |
| 8-10 | 3-ClPh | H | 4-(2-iByrOEt)— | H | H |
| 8-11 | 3,4-diClPh | H | 4-(2-ValOEt)— | H | H |
| 8-12 | 3,5-diClPh | H | 4-(2-iValOEt)— | H | H |
| 8-13 | 2-Np | H | 4-(2-PivOEt)— | H | H |
| 8-14 | 3-Tfmph | H | 4-(1-AcOEt)— | H | H |
| 8-15 | Ph | Me | 4-(2-AcOEt)— | H | H |
| 8-16 | 3-ClPh | H | 4-(1,2-diAcOEt)— | H | H |
| 8-17 | 2-Np | H | 4-(1,2-diAcOEt)— | H | H |
| 8-18 | 3-ClPh | H | 4-(2-AcO-1-HOEt)— | H | H |
| 8-19 | 3-Cl-4-FPh | H | 4-(2,3-diAcOPr)— | H | H |
| 8-20 | 3-ClPh | H | 4-(AcOCH₂)₂CH— | H | H |
| 8-21 | 2-Np | H | 4-(PivOCH₂)₂CH— | H | H |
| 8-22 | 3-ClPh | H | 4-[2,2-di(AcOCH₂)Et]— | H | H |
| 8-23 | 3-Cl-4-FPh | H | 4-(2-AcO-1-HOEt)— | H | H |

Of the compounds listed above, preferred compounds are Compounds No.:

3-1. 2-[2-(4-Methoxycarbonylmethylphenoxy)-1-methylethyl]amino-1-(3-chlorophenyl)ethanol;

3-5. 2-{2-[4-(2-Methoxycarbonylethyl)phenoxy]-1-methylethyl}amino-1-phenylethanol;

3-14. 2-[2-(4-Methoxycarbonylmethylphenoxy)-1-methylethyl]amino-1-(3-bromophenyl)ethanol;

3-15. 2-[2-(4-Methoxycarbonylmethylphenoxy)-1-methylethyl]amino-1-(3,5-dichlorophenyl)ethanol;

3-29. 2-[2-(4-Methoxycarbonylmethylphenoxy)-1-methylethyl]amino-1-phenylethanol;

3-41. 2-[2-(4-Methoxycarbonylmethylphenoxy)-1-methylethyl]amino-1-(3-chloro-4-fluorophenyl)ethanol;

3-62. 2-[2-(4-Methoxycarbonylmethylphenoxy)-1-methylethyl]amino-1-(3-methoxyphenyl)ethanol;

3-66. 2-[2-(4-Methoxycarbonylmethylphenoxy)-1-methylethyl]amino-1-(3-trifluoromethylphenyl)ethanol;

5-1. 5-[4-{2-[2-(3-Chlorophenyl)-2-hydroxyethylamino]propoxy}benzyl]thiazolidine-2,4-dione;

5-3. 5-[4-{2-[2-(3-Trifluoromethylphenyl)-2-hydroxyethylamino]propoxy}benzyl]thiazolidine-2,4-dione;

6-1. 2-[2-{4-(α-Methoxycarbonyl-α-hydroxymethyl)phenoxy]-1-methylethyl}amino-1-(3-chlorophenyl)ethanol;

6-2. 2-{2-[4-(2-Methoxycarbonyl-2-hydroxyethyl)phenoxy]-1-methylethyl}amino-1-(3-chlorophenyl)ethanol;

7-2. 2-[2-(4-Hydroxymethylphenoxy)-1-methylethyl]amino-1-(3-chlorophenyl)ethanol;

7-3. 2-{2-[4-(2-Hydroxyethyl)phenoxy]-1-methylethyl}amino-1-(3-chlorophenyl)ethanol;

7-4. 2-{2-[4-(3-Hydroxypropyl)phenoxy]-1-methylethyl}amino-1-(3-chlorophenyl)ethanol;
and salts thereof.

The most preferred compounds are Compounds No.: 3-1, 3-14, 3-29, 3-41, 3-66, 5-1, 5-3, 6-2 and 7-3 and salts thereof.

The compounds of the present invention can be prepared by a variety of well known processes which are known per se. For example, in general terms, they may be prepared by reacting a compound of formula (V):

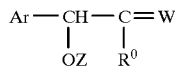

(in which Ar and $R^0$ are as defined above; Z represents a hydrogen atom or a hydroxy-protecting group; and W represents an oxygen atom, or it represents a hydrogen atom on one bond of the associated carbon atom and an amino group or a halogen atom on the other bond of the associated carbon atom) or an epoxide corresponding to said compound of formula (V) where W represents a hydrogen atom and a halogen atom with a compound of formula (VI):

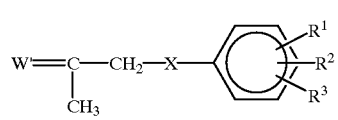

(in which X, $R^1$, $R^2$ and $R^3$ are as defined above; and, where W represents said hydrogen atom and said halogen atom or W represents said oxygen atom, W' represents a hydrogen atom on one bond of the associated carbon atom and an amino group on the other bond of the associated carbon atom, or, where W represents said hydrogen atom and said amino group, W' represents an oxygen atom);
and, if necessary, reducing the resulting compound;
and, if necessary, removing any protecting group;
and optionally salifying any resulting compound.

As explained in more detail below, in Method 1, where W represents a hydrogen atom and an amino group, and W' represents an oxygen atom, the product of the reaction of the compounds of formula (V) and (VI) contains a double bond and is reduced to give the compound of formula (I). The epoxide corresponding to the compound of formula (V) where W represents a hydrogen atom and a halogen atom can be treated in essentially the same way as that compound where W represents a hydrogen atom and a halogen atom, also as explained in greater detail hereafter, in Method 3.

Specific examples of processes which can be used to prepare the compounds of the present invention are shown in the following Methods 1 to 6.

Method 1

In this Method, an amino-alcohol of formula (VII):

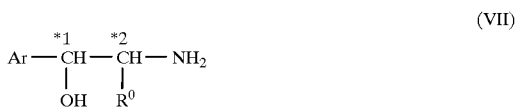

(in which $R^0$ and Ar are as defined above) [vide, for example, D. T. Collins, J. Med. Chem., 13, 674–680 (1970)] is reacted with a keto compound of formula (VIII):

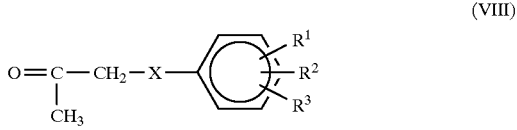

(in which $R^1$, $R^2$, $R^3$ and X are as defined above), to give a compound of formula (IX):

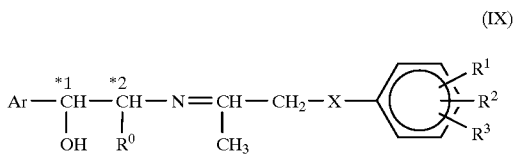

(in which $R^0$, $R^1$, $R^2$, $R^3$, X and Ar are as defined above) [Step A] and then the resulting compound is reduced [Step B].

The compound of formula (VIII) can be prepared by conventional means, for example by reacting a haloacetone with a phenol or thiophenol compound, using methods well known in the art.

In Step A of this reaction, a compound of formula (IX) is prepared by reacting an amino-alcohol of formula (VII) with a keto compound of formula (VIII). The reaction may be carried out in the presence or absence of a dehydrating agent, such as anhydrous sodium carbonate, anhydrous potassium carbonate, anhydrous sodium sulfate, anhydrous calcium chloride, anhydrous magnesium sulfate or a dehydrating molecular sieve.

In general, the reaction is preferably carried out in the presence of a solvent, the nature of which is not critical, provided that it has no adverse effect upon the reaction and that it can dissolve the reagents, at least to some extent. Examples of suitable solvents include: hydrocarbons, which may be aliphatic or aromatic, such as benzene, toluene, xylene, hexane and heptane; halogenated hydrocarbons, especially halogenated aliphatic hydrocarbons, such as chloroform, methylene chloride and carbon tetrachloride; ethers, such as diethyl ether, tetrahydrofuran and dioxane; amides, such as dimethylformamide, dimethylacetamide, hexamethylphosphoric triamide; alcohols, such as methanol and ethanol; sulfoxides, such as dimethyl sulfoxide; sulfolane; and mixtures of any two or more of the solvents described above.

The reaction will take place over a wide range of temperatures, and the precise reaction temperature chosen is not critical to the invention. In general, we find it convenient to carry out the reaction at a temperature in the range of from ice-cooling to the boiling point of the solvent used. The time required for the reaction may likewise vary widely, depending on many factors, notably the reaction temperature and the nature of the reagents. However, in most cases where the reaction is carried out under the preferred conditions outlined above, a period of from 0.5 to 10 hours will suffice.

The reaction is preferably carried out in the presence of a solvent, such as a hydrocarbon or an alcohol, for a period of from 1 to 5 hours at a temperature from ice-cooling to the reflux temperature. More preferably the reaction is carried out in benzene by heating under reflux for a period of from 1 to 3 hours and removing the resulting water.

In Step B, a compound of formula (I) is prepared by reducing the compound of formula (IX), which may have been prepared as described in Step A. The reaction is normally carried out by using a reducing agent or by hydrogenation in the presence of a catalyst. Where reduction is carried out using a reducing agent, the nature of the reducing agent used is not critical to the present invention, and any reducing agent commonly used in reactions of this type may equally be used here. Examples of suitable reducing agents include: metal hydrides, such as lithium borohydride, sodium borohydride, sodium cyanoborohydride, lithium aluminum hydride or diisobutylaluminum hydride. In general, the reaction is preferably carried out in the presence of a solvent, the nature of which is not critical, provided that it has no adverse effect upon the reaction and that it can dissolve the reagents, at least to some extent. Examples of suitable solvents include: hydrocarbons, which may be aliphatic or aromatic, such as benzene, toluene, xylene, hexane or heptane; ethers, such as diethyl ether, tetrahydrofuran or dioxane; amides, such as dimethylformamide, dimethylacetamide or hexamethylphosphoric triamide; alcohols, such as methanol, ethanol or isopropanol; and mixtures of any two or more of the solvents described above.

The reaction will take place over a wide range of temperatures, and the precise reaction temperature chosen is not critical to the invention. In general, we find it convenient to carry out the reaction at any temperature from ice-cooling to heating, for example to 50° C. or more. The time required for the reaction may likewise vary widely, depending on many factors, notably the reaction temperature and the nature of the reagents. However, in most cases, a period of from 0.5 hour to several days will normally suffice.

The reaction is preferably carried out using sodium borohydride or sodium cyanoborohydride in the presence of an alcoholic solvent, and at a temperature of from ice-cooling to 50° C. for a period of from 1 to 24 hours.

Where reduction is carried out by hydrogenation in the presence of catalyst, the catalyst used may be any catalyst commonly used for catalytic reduction, and the nature of the catalyst is not critical to the present invention. Examples of preferred catalysts include palladium-on-charcoal or platinum oxide. In general, the reaction is preferably carried out in the presence of a solvent, the nature of which is not critical, provided that it has no adverse effect upon the reaction and that it can dissolve the reagents, at least to some extent. Examples of suitable solvents include: ethers, such as diethyl ether, tetrahydrofuran or dioxane; amides, such as dimethylformamide or dimethylacetamide; alcohols, such as methanol, ethanol or isopropanol; esters, such as methyl acetate or ethyl acetate; and mixtures of any two or more of the solvents described above. Where a palladium catalyst is used, the catalytic hydrogenation is preferably carried out under from medium to high pressure, preferably at from 1 to 5 kg/cm$^2$. Where a platinum catalyst is used, the hydrogenation is preferably carried out at atmospheric pressure. The reaction will take place over a wide range of temperatures, and the precise reaction temperature chosen is not critical to the invention. In general, we find it convenient to carry out the reaction at a temperature in the range of from room temperature to 50° C. It is also preferably carried out in the presence of an alcoholic solvent, particularly methanol or ethanol.

Where the compound of formula (VII) is an optically active compound owing to the presence of asymmetric carbon atoms at the positions marked by *1 and/or *2, the stereochemical integrity can be retained in the compound of formula (IX) and thus the compound of formula (I), so produced. Moreover, in Step B, where a conventional asymmetric hydrogenation reaction can be carried out, compounds of formula (I) can be prepared as a stereoisomer having an asymmetric carbon atom at the position marked by *3.

Method 2

In this Method, a compound of formula (I) is prepared by reacting a halohydrin of general formula (X):

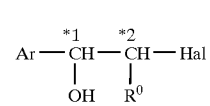

(X)

(in which R$^0$ and Ar are as defined above and Hal represents a halogen atom, such as a chlorine or bromine atom) with an amine of formula (XI):

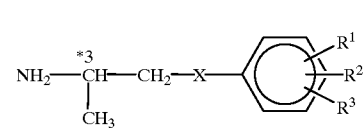

(XI)

(in which R$^1$, R$^2$, R$^3$ and X are as defined above).

The reaction may be carried out in the presence or absence of a deacidifying agent, which may be a base, such as sodium carbonate, sodium hydrogencarbonate, potassium carbonate or triethylamine. Also, it is preferably carried out in the presence of a solvent, the nature of which is not critical, provided that it has no adverse effect upon the reaction and that it can dissolve the reagents, at least to some extent. Examples of suitable solvents include: hydrocarbons, which may be aliphatic or aromatic, such as benzene, toluene, xylene, hexane or heptane; halogenated hydrocarbons, especially halogenated aliphatic hydrocarbons, such as chloroform, methylene chloride or carbon tetrachloride; ethers, such as diethyl ether, tetrahydrofuran or dioxane; amides, such as dimethylformamide, dimethylacetamide or hexamethylphosphoric triamide; alcohols, such as methanol, ethanol or isopropanol; sulfoxides, such as dimethyl sulfoxide; and mixtures of the solvents described above.

The reaction will take place over a wide range of temperatures, and the precise reaction temperature chosen is not critical to the invention. In general, we find it convenient to carry out the reaction at any temperature from room temperature to the reflux temperature of the reaction medium. The time required for the reaction may likewise vary widely, depending on many factors, notably the reaction temperature and the nature of the reagents. However, in most cases, a period of from 1 hour to several days will normally suffice. The reaction is preferably carried out in the presence of a solvent, such as an alcohol, an amide or a sulfoxide, at a temperature from room temperature to 60° C., and for a period of from 3 hours to 3 days.

Compounds of formula (XI) can be prepared by the procedure summarized in the following reaction scheme A:

reaction may be carried out by conventional procedures, for example using the Mitsunobu reaction [O. Mitsunobu, Synthesis, 1 (1981)]. In general, the reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as benzene, toluene, xylene, hexane or heptane; halogenated hydrocarbons, especially halogenated aliphatic hydrocarbons, such as chloroform, methylene chloride or carbon tetrachloride; ethers, such as diethyl ether, tetrahydrofuran or dioxane; amides, such as dimethylformamide, dimethylacetamide or hexamethylphosphoric triamide; and mixtures of any two or more of the solvents described above. The reaction can take place over a wide range of temperatures, and the precise reaction temperature is not critical to the invention. In general, we find it convenient to carry out the reaction at a temperature of from that of an ice-water bath to some heating, more preferably from ice-cooling to 60° C. The time required for the reaction may also vary widely, depending on many factors, notably the reaction temperature and the nature of the reagents and solvent employed. However, provided that the reaction is effected under the preferred conditions out-

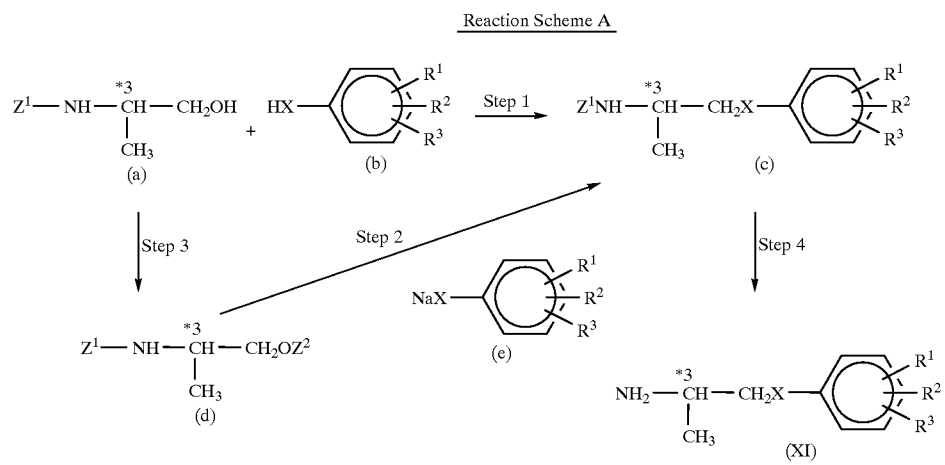

Reaction Scheme A

In the above formulae, $R^1$, $R^2$, $R^3$ and X are as defined above; $Z^1$ represents an amino-protecting group, for example an alkoxycarbonyl group or an aryloxycarbonyl group, which may be as defined and exemplified in relation to the similar groups which may be included in substituents A above, such as a t-butoxycarbonyl group or a benzyloxycarbonyl group; and $Z^2$ represents a sulfonyl group, such as an alkanesulfonyl group in which the alkyl moiety preferably has from 1 to 4 carbon atoms, or an arylsulfonyl group in which the aryl part may be as previously defined and exemplified, for example a mesyl (methanesulfonyl) group or a tosyl (toluenesulfonyl, preferably p-toluenesulfonyl) group.

In step 1 of this reaction scheme, a compound of formula (c) is prepared by reacting an N-protected amino-alcohol of formula (a) with a phenyl compound of formula (b). This lined above, a period of from several hours to several days, more preferably from 5 hours to 3 days, will usually suffice.

A compound of formula (c) can also be prepared, as shown by step 2, by reacting a compound of formula (d) with a compound of formula (e). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as benzene, toluene, xylene, hexane or heptane; ethers, such as diethyl ether, tetrahydrofuran or dioxane; amides, such as dimethylformamide, dimethylacetamide or hexamethylphosphoric triamide; and mixtures of any two or more of the solvents described above. The reaction can take place over a wide range of temperatures, and the precise reaction temperature is not critical to the invention. In general, we find it convenient to carry out the reaction at a temperature of from that of an ice-water bath to some heating, more preferably from ice-cooling to 60° C. The time required for the reaction may also vary widely, depending on many factors, notably the reaction temperature and the nature of the reagents and solvent employed. However, provided that the reaction is effected under the preferred conditions outlined above, a period of from 1 hour to several days, more preferably from 1 to 24 hours, will usually suffice. The reaction is preferably carried out in the presence of a solvent at a temperature of from ice-cooling to 60° C. for a period of from 1 to 24 hours.

A compound of formula (d) can be prepared, as shown in step 3, by protecting the amino group, for example by mesylation or tosylation, of a compound of formula (a). The reaction may be carried out in the presence or absence of a deacidifying agent, such as sodium carbonate, sodium hydrogencarbonate, potassium carbonate, triethylamine or pyridine, and preferably in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as benzene, toluene, xylene, hexane or heptane; halogenated hydrocarbons, especially halogenated aliphatic hydrocarbons, such as chloroform, methylene chloride or carbon tetrachloride; ethers, such as diethyl ether, tetrahydrofuran or dioxane; amides, such as dimethylformamide, dimethylacetamide or hexamethylphosphoric triamide; sulfoxides, such as dimethyl sulfoxide; and mixtures of any two or more of the solvents described above. The reaction can take place over a wide range of temperatures, and the precise reaction temperature is not critical to the invention. In general, we find it convenient to carry out the reaction at a temperature of from that of an ice-water bath to some heating, more preferably from ice-cooling to 60° C. The time required for the reaction may also vary widely, depending on many factors, notably the reaction temperature and the nature of the reagents and solvent employed. However, provided that the reaction is effected under the preferred conditions outlined above, a period of from 1 hour to several days, more preferably from 1 to 24 hours, will usually suffice. The reaction is preferably carried out in the presence of triethylamine at a temperature of from ice-cooling to 60° C. for a period of from 1 to 24 hours.

A compound of formula (XI) can then be prepared, as shown in step 4, by removing the amino-protecting groups, such as the t-butoxycarbonyl or benzyloxycarbonyl groups, from the compound of formula (c) by conventional means (for example, as described in T. W. Green, "Protective Groups in Organic Synthesis", John Wiley & Sons; and J. F. W. McOmie, "Protective Groups in Organic Chemistry", Plenum Press).

Optically active compounds of formula (XI) can be prepared by using an optically active compound of formula (a) as the starting material.

Where the compounds of formulae (X) and (XI) are optically active, reacting them together will give the respective stereoisomers owing to the asymmetric carbon atoms at the positions marked by *1, *2 and *3 as shown in formulae (IV), (X) and (XI).

Method 3

A compound of formula (I) can be prepared by reacting an epoxidized compound of formula (XII):

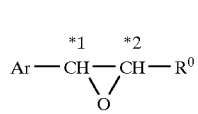
(XII)

(in which $R^0$ and Ar are as defined above) with an amino compound of formula (XI):

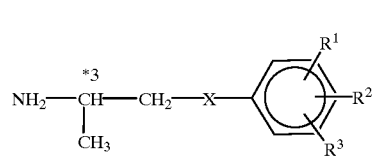
(XI)

(in which $R^1$, $R^2$ and X are as defined above).

The reaction may be carried out in the presence or absence of an acid catalyst, such as hydrogen chloride, sulfuric acid, boron trifluoride or aluminum chloride, or of basic alumina and preferably in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as benzene, toluene, xylene, hexane or heptane; halogenated hydrocarbons, especially halogenated aliphatic hydrocarbons, such as chloroform, methylene chloride or carbon tetrachloride; ethers, such as diethyl ether, tetrahydrofuran or dioxane; amides, such as dimethylformamide, dimethylacetamide or hexamethylphosphoric triamide; alcohols, such as methanol, ethanol or isopropanol; sulfoxides, such as dimethyl sulfoxide; nitriles, such as acetonitrile; water; and mixtures of any two or more of the solvents described above. The reaction can take place over a wide range of temperatures, and the precise reaction temperature is not critical to the invention. In general, we find it convenient to carry out the reaction at a temperature of from that of an ice-water bath to some heating, more preferably from ice-cooling to 120° C. The time required for the reaction may also vary widely, depending on many factors, notably the reaction temperature and the nature of the reagents and solvent employed. However, provided that the reaction is effected under the preferred conditions outlined above, a period of from 1 hour to several days, more preferably from 1 to 24 hours, will usually suffice. The reaction is preferably carried out in the presence of a solvent at a temperature of from 30° C. to 120° C. for a period of from 1 to 24 hours.

Where the compounds of formulae (XI) and (XII) are optically active, reaction of these two compounds may yield the respective stereoisomers of the compound of formula (I) owing to the asymmetric carbon atoms at the positions marked by *1, *2 and *3 as shown in formulae (IV), (XI) and (XII).

Method 4

A compound of formula (I) can be prepared by [Step A1] reacting a carbonyl compound of formula (XIII):

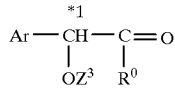

(XIII)

(in which $R^0$ and Ar are as defined above and $Z^3$ represents a hydrogen atom or a hydroxy-protecting group) with an amino compound of formula (XI), as shown above, to produce a compound of formula (XIV):

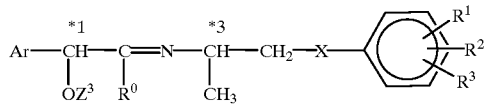

(XIV)

(in which, $R^0$, $R^1$, $R^2$, $R^3$, X, Ar and $Z^3$ are as defined above) and then [Step B1] reducing the resulting compound of formula (XIV) to produce a compound of formula (XV):

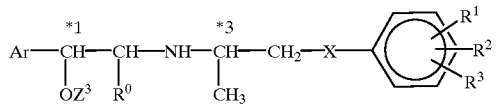

(XV)

(in which, $R^0$, $R^1$, $R^2$, $R^3$, X, Ar and $Z^3$ are as defined above) and then, if necessary, deprotecting the compound where $Z^3$ represents a hydroxy-protecting group, to give a compound of formula (I).

Step A1 and B1 are essentially the same as, and may be carried out under similar conditions to, those described in Steps A and B of Method 1.

The nature of the hydroxy-protecting group represented by $Z^3$ is not critical to the present invention, and any such group which may conventionally be used as a hydroxy-protecting group, may equally be used in the present reaction. Examples of such groups include the tetrahydropyranyl, methoxymethyl, diphenylmethyl, trityl, trimethylsilyl, t-butyldimethylsilyl and t-butyldiphenylsilyl groups. Following Steps A1 and B1, if the protecting group needs to be removed, the nature of the removal reaction will depend on the nature of the protecting group, as is well known in the art, and the reactions employed are also well known. Examples of such removal reactions are given in T. W. Green, "Protective Groups in Organic Synthesis", John Wiley & Sons; and J. F. W. McOmie, "Protective Groups in Organic Chemistry", Plenum Press, the disclosures of which are incorporated herein by reference.

Those compounds of formula (XIII) in which $R^0$ represents a hydrogen atom, that is compounds of formula (XVI):

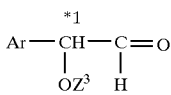

(XVI)

can be prepared by the procedure summarized in the following reaction scheme B:

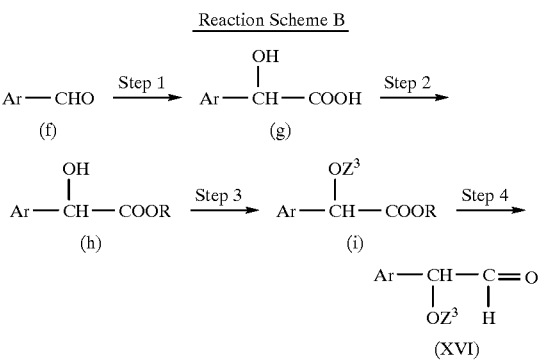

(XVI)

In the above formulae, Ar and $Z^3$ are as defined above and R represents a lower alkyl group, preferably having from 1 to 4 carbon atoms, for example as exemplified in relation to substituents B, above.

In step 1 of this reaction scheme, a compound of formula (f) is treated by conventional means, for example, as described in Organic Syntheses I, pp. 336, the disclosure of which is incorporated herein by reference, to give a compound of formula (g).

The reaction is normally carried out by reacting the compound of formula (f) with hydrogen cyanide or with trimethylsilyl cyanide in the presence of zinc iodide, and in the presence or absence of a solvent, to prepare a cyanohydrin derivative, and then subjecting the resulting cyanohydrin compound to hydrolysis catalyzed by an acid. The reaction for forming the cyanohydrin compound is normally carried out over a wide range of temperatures, for example from ice-cooling to heating, preferably at a temperature of from room temperature to 100° C. Hydrolysis catalyzed by an acid is normally carried out using a conventional acid, for example, an inorganic acid, such as hydrochloric acid or sulfuric acid, or an organic acid, such as p-toluenesulfonic acid or acetic acid, in the presence of an excess of water at a temperature of from room temperature to the reflux temperature of the reaction mixture for a period of from several tens of minutes to several tens of hours. The reaction is preferably carried out by heating under reflux in the presence of hydrochloric acid or sulfuric acid for a period of from 30 minutes to 10 hours.

Subsequently, esterification of the compound of formula (g) thus obtained can be effected by acid-catalyzed esterification or by treatment with an esterifying agent, such as a diazoalkane or an alkyl halide plus alkali, to produce a compound of formula (h).

Acid-catalyzed esterification may be effected by reacting the compound of formula (g) with, for example, an excess of an alcohol, in the presence or absence of a solvent, and preferably in the presence of an inorganic acid, such as hydrogen chloride or sulfuric acid, or an organic acid, such as p-toluenesulfonic acid, at a suitable temperature, for example from room temperature to heating, for a suitable period, for example from several hours to several days.

Esterification using a diazoalkane is preferably effected in the presence of a solvent, for example: an alcohol, such as methanol or ethanol; a hydrocarbon, which may be aliphatic or aromatic, such as benzene, toluene, xylene, hexane or heptane; an ether, such as diethyl ether, tetrahydrofuran or dioxane; or a mixture of any two or more of the solvents described above. The reaction can take place over a wide range of temperatures, and the precise reaction temperature is not critical to the invention. In general, we find it convenient to carry out the reaction at a temperature of from ice-cooling to heating, more preferably at a temperature of from ice-cooling to 60° C. The time required for the reaction may also vary widely, depending on many factors, notably the reaction temperature and the nature of the reagents and solvent employed.

In an esterification reaction using an alkali and an alkyl halide, examples of the alkali which may be used include alkali metal carbonates, such as potassium carbonate or sodium carbonate. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as diethyl ether, tetrahydrofuran or dioxane; hydrocarbons, such as benzene, toluene, xylene, hexane or heptane; amides, such as dimethylformamide, dimethylacetamide or hexamethylphosphoric triamide; and mixtures of any two or more of the solvents described above. The reaction can take place over a wide range of temperatures, and the precise reaction temperature is not critical to the invention. In general, we find it convenient to carry out the reaction at a temperature of from about room temperature to heating. The time required for the reaction may also vary widely, depending on many factors, notably the reaction temperature and the nature of the reagents and solvent employed. However, provided that the reaction is effected under the preferred conditions outlined above, a period of from several hours to several days will usually suffice.

In step 3, the compound of formula (h) thus obtained is protected using a conventional hydroxy-protecting group to produce a compound of formula (i). Examples of the hydroxy-protecting groups which may be used include: tetrahydropyranyl, methoxymethyl, diphenylmethyl, trityl, trimethylsilyl, t-butyldimethylsilyl and t-butyldiphenylsilyl groups, for example, as described in T. W. Green, "Protective Groups in Organic Syntheses", John Wiley & Sons; and J. F. W. McOmie, "Protective Groups in Organic Chemistry", Plenum Press.

In step 4, the compound of formula (XVI) can then be prepared by conventional means from the compound (i), for example, by reacting the compound of formula (i) with diisobutylaluminum hydride in a hydrocarbon solvent such as hexane, heptane, benzene toluene or xylene, which has been precooled in an acetone-dry ice-bath.

The compound of formula (XVI) can also be prepared by the procedure summarized in the following reaction scheme C:

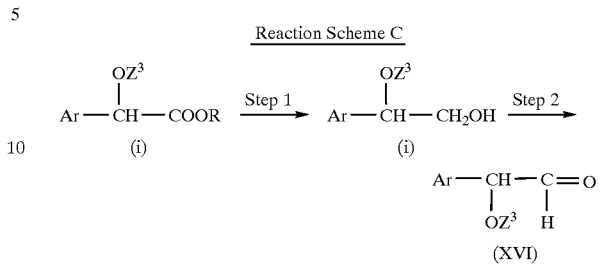

(in which Ar, $Z^3$ and R are as defined above).

In step 1 of this reaction scheme, a compound of formula (i) is reacted by conventional means with, for example, a metal hydride, such as lithium aluminum hydride or diisobutylaluminum hydride, to produce a compound of formula (j).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as diethyl ether, tetrahydrofuran and dioxane.

The compound of formula (j) thus obtained is then oxidized in step 2 by conventional means, for example, using a sulfur trioxide/pyridine complex or a chromium oxidizing agent or by subjecting it to a Swern oxidation reaction to produce the compound of formula (XVI).

Where the compound of formula (XVI) is optically active, it is possible to obtain stereoisomers of the compound formula (IV) having an asymmetric carbon atom at the position marked by *1. That is, where the amino compound of formula (XIV) is optically active and $R^0$ represents a hydrogen atom, there can be separately prepared compounds of formula (IV) having stereochemistry made up of any desired combination of (*1R, *3R), (*1R, *3S), (*1S, *3R) or (*1S, *3S).

Moreover, a compound of formula (g) can be resolved into (R) and (S) compounds using any optically active amine which can be used for conventional optical resolution, for example, (+)- or (−)-ephedrine or (d)- or (l)-1-phenylethylamine.

Method 5

A compound wherein $R^1$, $R^2$ or $R^3$ represents a hydroxyalkyl group can be prepared by reducing a corresponding compound wherein $R^1$, $R^2$ or $R^3$ represents an alkoxycarbonyl group. The reaction is normally carried out using a reducing agent. Examples of the reducing agents which may be used include: metal hydrides, such as lithium borohydride, sodium borohydride, sodium cyanoborohydride, lithium aluminum hydride or diisobutylaluminum hydride. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as benzene, toluene, xylene, hexane or heptane; ethers, such as diethyl ether, tetrahydrofuran or dioxane; amides, such as dimethylformamide, dimethylacetamide or hexamethylphosphoric triamide; alcohols such as methanol, ethanol or isopropanol; and mixtures of any two or more of the solvents described above. The reaction can take place over a wide range of temperatures, and the precise reaction temperature is not critical to the invention. In general, we find it convenient to carry out the reaction at a temperature of from ice-cooling to heating, for example at or up to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from 0.5 hour to several days will usually suffice. The reaction is preferably carried out using sodium borohydride or lithium borohydride in the presence of an alcoholic solvent at a temperature of from ice-cooling to the reflux temperature of the reaction mixture for a period of from 1 to 24 hours. Alternatively, the reaction is also preferably carried out using lithium aluminum hydride in the presence of an ether solvent at a temperature of from ice-cooling to the reflux temperature of the reaction mixture for a period of from 1 to 24 hours.

Method 6

A compound corresponding to a compound of formula (I) but in which the substituted alkyl group represented by $R^1$, and optionally by $R^2$ and/or $R^3$, is replaced by a substituted alkenyl group can be converted to the corresponding compound of formula (I) by catalytic hydrogenation.

The catalyst used may be any catalyst commonly used for catalytic reduction, and the nature of the catalyst is not critical to the present invention. Examples of preferred catalysts include palladium-on-charcoal or platinum oxide. In general, the reaction is preferably carried out in the presence of a solvent, the nature of which is not critical, provided that it has no adverse effect upon the reaction and that it can dissolve the compound to be reduced, at least to some extent. Examples of suitable solvents include: ethers, such as diethyl ether, tetrahydrofuran or dioxane; amides, such as dimethylformamide or dimethylacetamide; alcohols, such as methanol, ethanol or isopropanol;.esters, such as methyl acetate or ethyl acetate; and mixtures of any two or more of the solvents described above. Where a palladium catalyst is used, the catalytic hydrogenation is preferably carried out under from medium to high pressure, preferably at from 1 to 5 kg/cm$^2$. Where a platinum catalyst is used, the hydrogenation is preferably carried out at atmospheric pressure. The reaction will take place over a wide range of temperatures, and the precise reaction temperature chosen is not critical to the invention. In general, we find it convenient to carry out the reaction at a temperature in the range of from room temperature to 50° C. It is also preferably carried out in the presence of an alcoholic solvent, particularly methanol or ethanol.

The desired compounds obtained by any of Methods 1 through 6 can be recovered from the reaction mixture by conventional means after completion of the reaction. The compounds thus obtained can, if desired, be further purified by standard techniques, for example, by the various chromatography techniques, notably column chromatography, and/or by recrystallization, reprecipitation or the like. One suitable recovery and purification technique comprises: adding a suitable solvent to the reaction mixture; extracting the product into the solvent; removing the solvent by distillation from the extract; and purifying the residue by column chromatography through silica gel or the like to afford the desired compound in a pure state.

BIOLOGICAL ACTIVITY

The compounds of formula (I) and their pharmaceutically acceptable salts have a variety of valuable physiological activities, which render them of great potential for the treatment or prophylaxis of a variety of physiological disorders. For example, they improve hyperglycemia, increase glucose tolerance which may have been impaired in obesity, they inhibit the activity of aldose reductase, and improve hepatic gluconeogenesis and hyperlipemia; they are useful as preventive and/or therapeutic agents for hyperglycemia, obesity, hyperlipemia and such diabetic complications as retinopathy, nephropathy, neuropathy, cataracts, coronary heart diseases and arteriosclerosis; they are also useful for the treatment and prevention of obesity-related hypertension and osteoporosis. In addition, since the compounds of the present invention have a very low toxicity, they are useful as a preventive and/or therapeutic agents for the diseases and disorders mentioned above.

The biological activities of the compounds of the present invention are illustrated in the following Experiments, in which the compounds of the invention are identified by the number of the one of the following Examples in which its preparation is described.

Experiment 1

Hypoglycemic Effect During Glucose Load

The hypoglycemic effect of the compounds of the present invention during glucose load in mice was measured as follows.

Three month old KK male mice, each weighing 28 to 30 g, were fasted overnight, and then 1 mg/kg of the compound to be tested or carboxymethylcellulose (CMC) as a control was administered orally. After 60 minutes, 1.2 g/kg of D-glucose was administered subcutaneously. Then, at 60 and 120 minutes after the subcutaneous glucose injection, blood samples were taken, and the glucose levels were determined by means of a glucose analyzer (GL-101, a product of Mitsubishi Kasei, Co.). The hypoglycemic rates (R) of the test compound during the glucose load were calculated according to the following equation:

$$R = [1-(B/A)] \times 100$$

where

A: Blood glucose level in the group administered CMC

B: Blood glucose level in the group administered a test sample.

The results are shown in Table 9.

TABLE 9

| Cpd. of Example No. | Dose (mg/kg) | Number of mice | Hypoglycemic rate during glucose load (%) | |
|---|---|---|---|---|
| | | | 60 min. | 120 min. |
| 3 | 1 | 4 | 67.3 | 56.5 |
| 6 | 1 | 4 | 43.4 | 40.5 |
| 8 | 1 | 4 | 56.8 | 45.1 |
| 24 | 1 | 4 | 61.4 | 56.9 |
| 27 | 1 | 4 | 68.4 | 52.1 |
| 40 | 1 | 4 | 37.9 | 24.5 |
| 41 | 1 | 4 | 50.1 | 43.0 |
| 42 | 1 | 4 | 60.9 | 57.6 |
| 43 | 1 | 4 | 66.5 | 58.6 |
| 44 | 1 | 4 | 38.1 | 24.8 |
| 47 | 1 | 4 | 60.9 | 51.5 |

As clearly shown in Table 9, all of the tested compounds showed an excellent hypoglycemic effect.

Experiment 2
Inhibition of Aldose Reductase

Bovine lens aldose reductase was separated and partially purified by the method of S. Hyman and J. H. Kinoshita [J. Biol. Chem., 240, 877 (1965)] and K. Inagaki, I. Miwa and J. Okuda [Arch. Biochem. Biophys., 316, 337 (1982)], and its activity was determined photometrically by the method of Varma et al. [Biochem. Pharmac., 25, 2505 (1976)]. Inhibition of enzyme activity was measured for the compounds of the present invention at a concentration of 5 μg/ml, and the results are shown in the following Table 10.

TABLE 10

| | Inhibition of Aldose reductase | |
|---|---|---|
| Cpd. of Example No. | Inhibition (%) at 5 μg/ml | $IC_{50}$ (μg/ml) |
| 34 | 63.3 | 2.5 |
| 36 | 60.4 | 2.9 |
| 48 | 47.5 | — |

Experiment 3
Toxicity

The test animals employed were male mice of the ddY strain. The animals were employed in groups of 3. The test compound was administered orally to each animal group at a dose of 300 mg/kg body weight. The compounds employed were those prepared as described in Examples 1, 3, 8, 24, 47 and 48. The animals were then observed for a period of one week following this administration, and, during the period of observation, they showed no abnormalities which could be attributed to the test compounds. All animals were alive at the end of the period of observation.

In view of the substantial dose administered to each animal, the zero mortality indicates that the compounds of the present invention have a very low toxicity.

The compounds of the present invention can be administered in various forms, depending upon the patient and the desired route of administration. Suitable formulations for oral administration include tablets, capsules, granules, powders or syrups; and suitable formulations for parentheral administration include injections (which may be intravenous, intramuscular or subcutaneous), drops or suppositories. These various preparations can be prepared by conventional means in which the active compound is mixed with any known additives commonly employed in the field of pharmaceutical preparations, such as vehicles, binders, disintegrators, lubricants, corrigents, solubilizers, suspending agents and coating agents. The dosage may be varied depending on the symptoms, age and body weight of the patient, the route of administration and the form of the preparation. However, a daily dose of from 0.01 mg to 2,000 mg, which may be administered in a single dose or in divided doses, is usually appropriate for an adult human patient.

The preparation of the compounds of the present invention is further illustrated by the following non-limiting Examples, and the preparation of certain of the starting materials is shown in the subsequent Preparations.

EXAMPLE 1

2-[2-(4-Hydroxymethylphenoxy)-1-methylethyl]-amino-1-(3-chlorophenyl)ethanol 1/6 ethyl acetate (Compound No. 7-2)

0.83 mg of lithium aluminum hydride was slowly added, with stirring, to a solution of 1.95 g of 2-[2-(4-methoxycarbonylphenoxy)-1-methylethyl]amino-1-(3-chlorophenyl)ethanol (prepared as described in Preparation 1) dissolved in 70 ml of tetrahydrofuran, and the resulting mixture was allowed to react at room temperature for 2 hours. At the end of this time, 0.9 ml of water, 0.9 ml of a 15% w/v aqueous solution of sodium hydroxide and 3 ml of water were added, in that order, to the reaction mixture, and the resulting mixture was stirred at room temperature. The reaction mixture was then filtered using a Celite (trade mark) filter aid, and the filtrate was freed from the solvent by distillation under reduced pressure. The resulting residue was purified by column chromatography through silica gel, using a 10:1 by volume mixture of ethyl acetate and ethanol as the eluent, to give 1.5 g of the title compound as a glass-like material, having an Rf=0.55 (thin layer chromatography over silica gel, using a 4:1 by volume mixture of ethyl acetate and ethanol as the developing solvent).

The product contains some proportion of ethyl acetate but is not thought to be a complex.

EXAMPLE 2

5-[4-{2-[2-(3-Chlorophenyl)-2-hydroxyethylamino]-propoxy}benzyl]thiazolidine-2,4-dione 1/2 ethyl acetate (Compound No. 5-1)

A solution of 2.5 g of 2-amino-1-(3-chlorophenyl)ethanol (prepared as described in Preparation 8) and 3.58 g of 5-[4-(2-oxopropoxy)benzyl]thiazolidine-2,4-dione in 50 ml of benzene was heated under reflux for 1.5 hours, whilst the water being formed during the reaction was continuously removed. At the end of this time, the benzene used was removed by distillation under reduced pressure. The resulting residue was dissolved in 100 ml of absolute methanol, and then 3 g of sodium borohydride were added to the resulting solution. The reaction mixture was allowed to stand overnight at room temperature, after which it was concentrated by evaporation under reduced pressure, and the concentrate was mixed with water. The resulting aqueous mixture was extracted with ethyl acetate and the extract was dried over anhydrous sodium sulfate. The solvent was removed by distillation under reduced pressure, and the resulting residue was purified by column chromatography through silica gel, using ethyl acetate, followed by a 10:1 by volume mixture of ethyl acetate and ethanol, as the eluent. The product was recrystallized from ethyl acetate, to give 0.74 g of the title compound as crystals, melting at 100–125° C.

EXAMPLE 3

2-[2-(4-Methoxycarbonylmethylphenoxy)-1-methylethyl]-amino-1-(3-chlorophenyl)ethanol (Compound No. 3-1)

A solution of 2.2 g of 2-amino-1-(3-chlorophenyl)ethanol (prepared as described in Preparation 8) and 2.6 g of methyl 4-(2-oxopropoxy)phenylacetate (prepared as described in Preparation 3) in 200 ml of benzene was heated under reflux for about 2 hours, whilst the water being formed during the reaction was continuously removed. At the end of this time, the reaction mixture was freed from the benzene used as solvent by distillation under reduced pressure, and the resulting residue was dissolved in 150 ml of absolute methanol. 1 g of sodium borohydride was added to this solution, whilst ice-cooling, and the resulting mixture was stirred at room temperature for 5 hours. The reaction mixture was then mixed with ethyl acetate and with a saturated aqueous solution of sodium chloride. The organic layer was separated and was dried over anhydrous magnesium sulfate, and the solvent was removed by distillation under reduced pressure. The resulting residue was purified by column chromatography through silica gel, using a 40:1:1 by volume mixture of ethyl acetate, ethanol and triethylamine as the eluent, to give 2.3 g of the title compound having an Rf=0.44 (thin layer chromatography over silica gel, using a 40:1:1 by volume mixture of ethyl acetate, ethanol and triethylamine as the developing solvent).

EXAMPLE 4

2-{2-[4-(3-Hydroxypropyl)phenoxy]-1-methylethyl}-amino-1-(3-chlorophenyl)ethanol (Compound No. 7-4)

A procedure similar to that described in Example 2 was repeated, except that 4.3 g of 2-amino-1-(3-chlorophenyl) ethanol (prepared as described in Preparation 8), 3.5 g of methyl 3-[4-(2-oxopropoxy)phenyl]propionate (prepared as described in Preparation 5), 150 ml of benzene, 150 ml of absolute methanol and 6.12 g of sodium borohydride were used. A crude product was obtained, and this was purified by column chromatography through silica gel, using a 10:1 by volume mixture of ethyl acetate and ethanol as the eluent, to give 2.9 g of the title compound having an Rf=0.40 (thin layer chromatography over silica gel, using a 10:1 by volume mixture of ethyl acetate and ethanol as the developing solvent).

EXAMPLE 5

2-{2-[4-(2-Methoxycarbonylethyl)phenoxy]-1-methylethyl}amino-1-phenylethanol (Compound No. 3-5)

2.2 g of 2-{2-[4-(2-methoxycarbonylethenyl)phenoxy]-1-methylethyl}amino-1-(3-chlorophenyl)ethanol (prepared as described in Preparation 53) were dissolved in 200 ml of methanol and hydrogenated by bubbling hydrogen through the solution at atmospheric pressure and at room temperature in the presence of 0.5 g of 10% w/w palladium-on-charcoal for 3 hours. The catalyst was removed by filtration, and the filtrate was concentrated by evaporation under reduced pressure. The concentrate was dissolved in ethyl acetate, and the resulting solution was washed with an aqueous solution of potassium carbonate and with water, in that order, after which it was dried over anhydrous sodium sulfate. The solvent was then removed by distillation under reduced pressure, and the residue was purified by column chromatography through silica gel, using ethyl acetate as the eluent. The product thus obtained was recrystallized from a mixture of ethyl acetate and hexane, to give 1.2 g of the title compound as crystals, melting at 103–104° C.

EXAMPLE 6

2-{2-[4-(2-Methoxycarbonyl-2-hydroxyethyl) phenoxy]-1-methylethyl}amino-1-(3-chlorophenyl) ethanol (Compound No. 6-2)

A mixture of 1.16 g of 2-amino-1-(3-chlorophenyl) ethanol (prepared as described in Preparation 8), 1.71 g of methyl 3-[4-(2-oxopropoxy)phenyl]acetate (prepared as described in Preparation 6) and 40 ml of benzene was heated under reflux for 3.5 hours, whilst the water being formed during the reaction was continuously removed. After completion of the reaction, the benzene used in the reaction was removed by distillation under reduced pressure, and the residue was dissolved in 50 ml of absolute methanol. 2.04 g of sodium cyanoborohydride were added, whilst ice-cooling, to the solution, and the resulting mixture was allowed to react overnight at room temperature. At the end of this time, methanol was removed by distillation under reduced pressure, and the resulting residue was mixed with ethyl acetate and with an aqueous solution of sodium chloride. The ethyl acetate layer was separated, washed with an aqueous solution of sodium chloride and then dried over anhydrous sodium sulfate. The solvent was then removed by distillation under reduced pressure, and the residue was purified by column chromatography through silica gel, using ethyl acetate as the eluent, to give 1.9 g of the title compound having an Rf=0.30 (thin layer chromatography over silica gel, using ethyl acetate as the developing solvent).

EXAMPLE 7

2-{2-[4-(2-Methoxycarbonylethyl)phenoxy]-1-methylethyl}amino-1-(3-chlorophenyl)ethanol (Compound No. 3-4)

Following a procedure similar to that described in Example 6, but using 4.5 g of 2-amino-1-(3-chlorophenyl)

ethanol (prepared as described in Preparation 8), 3.5 g of methyl 3-[4-(2-oxopropoxy)phenyl]propionate (prepared as described in Preparation 5), 100 ml of benzene, 100 ml of absolute methanol and 2.6 g of sodium cyanoborohydride, 2.8 g of the title compound were obtained as crystals, melting at 65–73° C.

EXAMPLE 8

2-{2-[4-(2-Hydroxyethyl)phenoxy]-1-methylethyl}-amino-1-(3-chlorophenyl)ethanol (Compound No. 7-3)

Following a procedure similar to that described in Example 2, but using 2.0 g of 2-amino-1-(3-chlorophenyl) ethanol (prepared as described in Preparation 8), 2.13 g of 2-[4-(2-oxopropoxy)phenyl]ethanol (prepared as described in Preparation 7), 100 ml of benzene, 100 ml of absolute methanol and 0.95 g of sodium borohydride, a crude product was obtained. This product was purified first by column chromatography through silica gel, using a 20:1 by volume mixture of ethyl acetate and ethanol as the eluent, and then by recrystallization from ethyl acetate, to give 1.18 g and 1.02 g of two separate kinds of crystals, which are diastereomers of the title compound, melting at 108–111° C. and at 78–80° C., respectively.

EXAMPLE 9

2-[2-(4-Methoxycarbonylmethylphenoxy)-1-methylethyl]-amino-2(S)-hydroxymethyl-1(S)-phenylethanol (Compound No. 3-6)

Following a procedure similar to that described in Example 6, but using 5.7 g of (1S,2S)-(+)-2-amino-1-phenyl-1,3-propanediol, 5 g of methyl 4-(2-oxopropoxy) phenylacetate (prepared as described in Preparation 3), 250 ml of benzene, 250 ml of absolute methanol and 4.34 g of sodium cyanoborohydride, 1.54 g of the title compound were obtained having an Rf=0.27 (thin layer chromatography over silica gel, using a 2:1 by volume mixture of ethyl acetate and hexane as the developing solvent).

EXAMPLE 10

2-[2-(4-Methoxycarbonylmethylphenoxy)-1-methylethyl]-amino-1-(2-naphthyl)ethanol (Compound No. 3-7)

Following a procedure similar to that described in Example 6, but using 3 g of 2-amino-1-(2-naphthyl)ethanol (prepared as described in Preparation 9), 3.87 g of methyl 4-(2-oxopropoxy)phenylacetate (prepared as described in Preparation 3), 60 ml of benzene, 50 ml of absolute methanol and 2.49 g of sodium cyanoborohydride, 3.23 g of the title compound were obtained having an Rf=0.15 (thin layer chromatography over silica gel, using ethyl acetate as the developing solvent).

EXAMPLE 11

2-[2-(4-Methoxycarbonylmethylphenoxy)-1-methylethyl]-amino-1-(1-naphthyl)ethanol (Compound No. 3-8)

Following a procedure similar to that described in Example 6, but using 3 g of 2-amino-1-(1-naphthyl)ethanol (prepared as described in Preparation 10), 3.87 g of methyl 4-(2-oxopropoxy)phenylacetate (prepared as described in Preparation 3), 60 ml of benzene, 50 ml of absolute methanol and 3 g of sodium cyanoborohydride, 1.9 g of the title compound were obtained having an Rf=0.35 (thin layer chromatography over silica gel, using ethyl acetate as the developing solvent).

EXAMPLE 12

2-[2-(4-Methoxycarbonylmethylphenoxy)-1-methylethyl]amino-2(S)-methyl-1(R)-phenylethanol (Compound No. 3-9)

Following a procedure similar to that described in Example 6. but using 3 g of (1R,2S)-(−)-norephedrine, 4.36 g of methyl 4-(2-oxopropoxy)phenylacetate (prepared as described in Preparation 3), 60 ml of benzene, 50 ml of absolute methanol and 3.41 g of sodium cyanoborohydride, 2.65 g of the title compound were obtained as crystals, melting at 124° C. (after recrystallization from a mixture of ethyl acetate and hexane).

EXAMPLE 13

2-[2-(4-Methoxycarbonylmethylphenoxy)-1-methylethyl]amino-2(R)-methyl-1(S)-phenylethanol (Compound No. 3-9)

Following a procedure similar to that described in Example 12, but using 3 g of (1S,2R)-(+)-1-norephedrine, 4.36 g of methyl 4-(2-oxopropoxy)phenylacetate (prepared as described in Preparation 3). 60 ml of benzene, 50 ml of absolute methanol and 3.57 g of sodium cyanoborohydride, 2.41 g of the title compound were obtained as crystals, melting at 122° C.

EXAMPLE 14

2-[2-(4-Methoxycarbonylmethylphenoxy)-1-methylethyl]-amino-1-(2-chlorophenyl)ethanol (Compound No. 3-11)

Following a procedure similar to that described in Example 6. but using 2 g of 2-amino-1-(2-chlorophenyl) ethanol (prepared as described in Preparation 11). 3.11 g of methyl 4-(2-oxopropoxy)phenylacetate (prepared as described in Preparation 3), 60 ml of benzene, 50 ml of absolute methanol and 2.3 g of sodium cyanoborohydride, 3.25 g of the title compound were obtained having an Rf=0.39 (thin layer chromatography over silica gel, using ethyl acetate as the developing solvent).

EXAMPLE 15

2-[2-(4-Methoxycarbonylmethylphenoxy)-1-methylethyl]-amino-1-(4-chlorophenyl)ethanol (Compound No. 3-12)

Following a procedure similar to that described in Example 12, but using 2 g of 2-amino-1-(4-chlorophenyl) ethanol (prepared as described in Preparation 12), 3.11 g of methyl 4-(2-oxopropoxy)phenylacetate (prepared as described in Preparation 3), 60 ml of benzene, 50 ml of absolute methanol and 2.7 g of sodium cyanoborohydride, 1.54 g of the title compound were obtained as crystals, melting at 78–79° C.

EXAMPLE 16

2-[2-(4-Methoxycarbonylmethylphenoxy)-1-methylethyl]-amino-1-(3-fluorophenyl)ethanol (Compound No. 3-13)

Following a procedure similar to that described in Example 6, but using 2 g of 2-amino-1-(3-fluorophenyl)ethanol (prepared as described in Preparation 13), 3.44 g of methyl 4-(2-oxopropoxy)phenylacetate (prepared as described in Preparation 3), 60 ml of benzene, 60 ml of absolute methanol and 3.6 g of sodium cyanoborohydride, 1.18 g of the title compound were obtained as crystals, melting at 52° C.

EXAMPLE 17

2-[2-(4-Methoxycarbonylmethylphenoxy)-1-methylethyl]-amino-1-(3,4,5-trimethoxyphenyl)ethanol (Compound No. 3-16)

Following a procedure similar to that described in Example 6, but using 2 g of 2-amino-1-(3,4,5-trimethoxyphenyl)ethanol (prepared as described in Preparation 14), 2.35 g of methyl 4-(2-oxopropoxy)phenylacetate (prepared as described in Preparation 3), 70 ml of benzene, 60 ml of absolute methanol and 4.8 g of sodium cyanoborohydride, 3.14 g of the title compound were obtained having an Rf=0.21 (thin layer chromatography over silica gel, using ethyl acetate as the developing solvent).

EXAMPLE 18

2-[2-(4-Methoxycarbonylmethylphenoxy)-1-methylethyl]-amino-1-(3-phenoxyphenyl)ethanol (Compound No. 3-26)

Following a procedure similar to that described in Example 6, but using 2 g of 2-amino-1-(3-phenoxyphenyl)ethanol (prepared as described in Preparation 15), 3.4 g of methyl 4-(2-oxopropoxy)phenylacetate (prepared as described in Preparation 3), 70 ml of benzene, 60 ml of absolute methanol and 3.7 g of sodium cyanoborohydride, 1.27 g of the title compound were obtained having an Rf=0.26 (thin layer chromatography over silica gel, using ethyl acetate as the developing solvent).

EXAMPLE 19

2-{2-[4-(2-Hydroxyethyl)phenoxy]-1-methylethyl}-amino-1(S)-phenylethanol (Compound No. 7-1)

A procedure similar to that described in Example 3 was repeated, except that 1.4 g of 2-amino-1(S)-phenylethanol (prepared as described in Preparation 16), 2.4 g of 2-[4-(2-oxopropoxy)phenyl]ethanol (prepared as described in Preparation 7), 100 ml of benzene, 100 ml of absolute methanol and 0.95 g of sodium cyanoborohydride were used and that, after the reaction, the reaction mixture was diluted with water and extracted with ethyl acetate. The extract was then concentrated by evaporation under reduced pressure, and the concentrate was purified by column chromatography through silica gel, using a 30:1 by volume mixture of ethyl acetate and ethanol as the eluent. 0.53 g of the title compound was obtained as crystals, melting at 93–96° C. (after recrystallization from ethyl acetate).

EXAMPLE 20

2-[2-(3-Methoxycarbonylmethylphenoxy)-1-methylethyl]-amino-1-(3-chlorophenyl)ethanol 1/4 hydrate (Compound No. 3-2)

Following a procedure similar to that described in Example 6, but using 2 g of 2-amino-1-(3-chlorophenyl)ethanol (prepared as described in Preparation 8), 3.11 g of methyl 3-(2-oxopropoxy)phenylacetate (prepared as described in Preparation 17), 70 ml of benzene, 60 ml of absolute methanol and 2.45 g of sodium cyanoborohydride, 2.57 g of the title compound were obtained having an Rf=0.38 (thin layer chromatography over silica gel, using ethyl acetate as the developing solvent).

EXAMPLE 21

2-[2-(2-Methoxycarbonylmethylphenoxy)-1-methylethyl]-amino-1-(3-chlorophenyl)ethanol (Compound No. 3-3)

Following a procedure similar to that described in Example 6, but using 2 g of 2-amino-1-(3-chlorophenyl)ethanol (prepared as described in Preparation 8), 3.11 g of methyl 2-(2-oxopropoxy)phenylacetate (prepared as described in Preparation 18), 70 ml of benzene, 60 ml of absolute methanol and 2.5 g of sodium cyanoborohydride, 3.1 g of the title compound were obtained having an Rf=0.30 (thin layer chromatography over silica gel, using ethyl acetate as the developing solvent).

EXAMPLE 22

2-[2-(4-Methoxycarbonylmethyl-2-chlorophenoxy)-1-methylethyl]amino-1-(3-chlorophenyl)ethanol (Compound No. 3-28)

Following a procedure similar to that described in Example 6, but using 5.15 g of 2-amino-1-(3-chlorophenyl)ethanol (prepared as described in Preparation 8), 10.3 g of methyl 3-chloro-4-(2-oxopropoxy)phenylacetate (prepared as described in Preparation 19), 200 ml of benzene, 100 ml of absolute methanol and 6 g of sodium cyanoborohydride, 1.2 g of the title compound were obtained as crystals, melting at 83–103° C. (after recrystallization from a mixture of ethyl acetate and hexane).

EXAMPLE 23

2-[2-(4-Carbamoylmethyl-2-chlorophenoxy)-1-methylethyl]amino-1-(3-chlorophenyl)ethanol 1/8 hydrate (Compound No. 4-6)

A solution of 2 g of 2-[2-(4-methoxycarbonylmethyl-2-chlorophenoxy)-1-methylethyl]amino-1-(3-chlorophenyl)

ethanol (prepared as described in Example 22) dissolved in 50 ml of methanol was saturated with gaseous ammonia in a reaction vessel, whilst ice-cooling, after which the reaction vessel was tightly stoppered and allowed to stand at room temperature for one week. At the end of this time, the solvent (methanol) was removed by distillation under reduced pressure, and the residue was recrystallized from ethyl acetate, to give 0.55 g of the title compound as crystals, melting at 99–101° C.

EXAMPLE 24

2-[2-(4-Methoxycarbonylmethylphenoxy)-1-methylethyl]-amino-1-(3-chlorophenyl)ethanol fumarate (fumarate of Compound No. 3-1)

A mixture of 10.0 g of 2-[2-(4-methoxycarbonylmethylphenoxy)-1-methylethyl]amino-1-(3-chlorophenyl)ethanol (prepared as described in Example 3) and 2.8 g of fumaric acid was dissolved in methanol and then the methanol was removed by distillation under reduced pressure. The residue was recrystallized from ethyl acetate, to give 11.5 g of the title compound as crystals, melting at 130–146° C.

EXAMPLE 25

2-{2-[3,4-Bis(hydroxymethyl)phenoxy]-1-methylethyl}-amino-1-(3-chlorophenyl)ethanol (Compound No. 7-7)

Following a procedure similar to that described in Example 1, but using 2.53 g of 2-{2-[3,4-bis(methoxycarbonyl)phenoxy]-1-methylethyl}amino-1-(3-chlorophenyl)ethanol (prepared as described in Preparation 20), 0.91 g of lithium aluminum hydride and 100 ml of dry tetrahydrofuran, and then purifying the reaction product by column chromatography through silica gel, using a 5:1 by volume mixture of ethyl acetate and ethanol as the eluent, 1.04 g of the title compound were obtained having an Rf=0.37 (thin layer chromatography over silica gel, using a 5:1 by volume mixture of ethyl acetate and ethanol as the developing solvent).

EXAMPLE 26

2-{2-[4-(1,1,2,2-Tetrakis(ethoxycarbonyl)ethyl]-phenoxy]-1-methylethyl}amino-1-(3-chlorophenyl)ethanol (Compound No. 3-22)

Following a procedure similar to that described in Example 6, but using 1 g of 2-amino-1-(3-chlorophenyl)ethanol (prepared as described in Preparation 8), 3 g of 4-[1,1,2,2-tetrakis(ethoxycarbonyl)ethyl]phenoxyacetone (prepared as described in Preparation 22), 100 ml of dry benzene, 50 ml of absolute methanol and 920 mg of sodium cyanoborohydride, and then purifying the reaction product by column chromatography through silica gel, using a 10:1 by volume mixture of ethyl acetate and hexane as the eluent, 0.4 g of the title compound was obtained having an Rf=0.35 (thin layer chromatography over silica gel, using ethyl acetate as the developing solvent).

EXAMPLE 27

2-[2-(4-Methoxycarbonylmethylphenoxy)-1(R)-methylethyl]amino-1(R)-phenylethanol (Compound No. 3-29)

870 mg of tetrabutylammonium fluoride were added to a solution of 510 mg of N-[2-(4-methoxycarbonylmethylphenoxy)-1(R)-methylethyl]-2(R)-t-butyldimethylsilyloxy-2-phenylethanamine (prepared as described in Preparation 29) in 15 ml of tetrahydrofuran, and the resulting mixture was stirred at room temperature for 2 hours. At the end of this time, the reaction mixture was diluted with water, and the aqueous mixture was extracted with ethyl acetate. The extract was dried over anhydrous sodium sulfate, and then the solvent was removed by distillation under reduced pressure. The resulting residue was purified by column chromatography through silica gel, using ethyl acetate as the eluent, to give 0.23 g of the title compound as crystals, melting at 69–70° C.

$[\alpha]^{23}_D$ –20.0° (c=1.000, chloroform).

EXAMPLE 28

2-[2-(4-Methoxycarbonylmethylphenoxy)-1(S)-methylethyl]-amino-1(S)-phenylethanol (Compound No. 3-29)

Following a procedure similar to that described in Example 27, but using 970 mg of N-[2-(4-methoxycarbonylmethylphenoxy)-1(S)-methylethyl]-2(S)-t-butyldimethylsilyloxy-2-phenylethanamine (prepared as described in Preparation 30), 20 ml of tetrahydrofuran and 1.7 g of tetrabutylammonium fluoride, 0.58 g of the title compound was obtained as crystals, melting at 70–71° C.

$[\alpha]^{23}_D$ +21.2° (c=1.02, chloroform).

EXAMPLE 29

2-[2-(4-Methoxycarbonylmethylphenoxy)-1(S)-methylethyl]-amino-1(R)-phenylethanol (Compound No. 3-29)

Following a procedure similar to that described in Example 27, but using 460 mg of N-[2-(4-methoxycarbonylmethylphenoxy)-1(S)-methylethyl]-2(R)-t-butyldimethylsilyloxy-2-phenylethanamine (prepared as described in Preparation 31), 15 ml of tetrahydrofuran and 780 mg of tetrabutylammonium fluoride, 0.23 g of the title compound was obtained as crystals, melting at 89–90° C.

$[\alpha]^{23}_D$ –44.9° (c=1.002, chloroform).

EXAMPLE 30

2-[2-(4-Methoxycarbonylmethylphenoxy)-1(R)-methylethyl]-amino-1(S)-phenylethanol (Compound No. 3-29)

Following a procedure similar to that described in Example 27, but using 880 mg of N-[2-(4-methoxycarbonylmethylphenoxy)-1(R)-methylethyl]-2(S)-t-butyldimethylsilyloxy-2-phenylethanamine (prepared as described in Preparation 32), 20 ml of tetrahydrofuran and 1.5 g of tetrabutylammonium fluoride, 0.5 g of the title compound was obtained as crystals, melting at 90–91° C. $[\alpha]_D^{23}$+45.2° (c=1.000, chloroform).

EXAMPLE 31

2-[2-(3-Methoxycarbonylmethyl-4-hydroxyphenoxy)-1-methylethyl]amino-1-phenylethanol 1/4 hydrate (Compound No. 3-60)

Following a procedure similar to that described in Example 6, but using 0.72 g of 2-amino-1-phenylethanol, 1.5 g of methyl 2-hydroxy-5-(2-oxopropoxy)phenylacetate (prepared as described in Preparation 21), 60 ml of benzene, 50 ml of absolute methanol and 1.9 g of sodium cyanoborohydride, and then purifying the reaction product by column chromatography through silica gel, using a 10:1 by volume mixture of ethyl acetate and ethanol as the eluent, 0.07 g of the title compound was obtained having an Rf=0.40 (thin layer chromatography over silica gel, using a 10:1 by volume mixture of ethyl acetate and ethanol as the developing solvent).

EXAMPLE 32

2-{2-[2,4-Bis(hydroxymethyl)phenoxy]-1-methylethyl}-amino-1-(3-chlorophenyl)ethanol 1/4 hydrate (Compound No. 7-8)

Following a procedure similar to that described in Example 1, but using 1.28 g of 2-{2-[2,4-bis(methoxycarbonyl)phenoxy]-1-methylethyl}amino-1-(3-chlorophenyl)ethanol (prepared as described in Preparation 33), 0.463 g of lithium aluminum hydride and 70 ml of dry tetrahydrofuran, and then purifying the reaction product by column chromatography through silica gel, using a 4:1 by volume mixture of ethyl acetate and ethanol as the eluent, 0.78 g of the title compound was obtained having an Rf=0.34 (thin layer chromatography over silica gel, using a 4:1 by volume mixture of ethyl acetate and ethanol as the developing solvent).

EXAMPLE 33

2-[2-(4-Methoxycarbonylmethyl-2-hydroxyphenoxy)-1-methylethyl]amino-1-(3-chlorophenyl)ethanol (Compound No. 3-23)

Following a procedure similar to that described in Example 6, but using 2 g of 2-amino-1-(3-chlorophenyl) ethanol (prepared as described in Preparation 8), 3.07 g of methyl 3-hydroxy-4-(2-oxopropoxy)phenylacetate (prepared as described in Preparation 34), 70 ml of dry benzene, 60 ml of absolute methanol and 1.7 g of sodium cyanoborohydride, and then purifying the reaction product by column chromatography through silica gel, using ethyl acetate as the eluent, 2.62 g of the title compound were obtained as crystals, melting at 68° C.

EXAMPLE 34

2-{2-[2-Chloro-4-(N-hydroxycarbamoylmethyl) phenoxy]-1-methylethyl}amino-1-(3-chlorophenyl) ethanol (Compound No. 4-15)

A mixture comprising 2.0 g of 2-[2-(4-methoxycarbonylmethyl-2-chlorophenoxy)-1-methylethyl] amino-1-(3-chlorophenyl)ethanol (prepared as described in Example 22), 6.25 g of hydroxylamine hydrochloride, 50 ml of methanol and 11 g of triethylamine was allowed to stand at room temperature for 8 days and then the solvent (methanol) was removed by distillation under reduced pressure. The resulting residue was mixed with ethyl acetate and with an aqueous solution of sodium chloride. The ethyl acetate layer was then separated and washed with an aqueous solution of sodium chloride; it was then dried over anhydrous sodium sulfate. The solvent was removed by distillation under reduced pressure, and the resulting residue was purified by column chromatography through silica gel, using a 5:2 by volume mixture of ethyl acetate and ethanol as the eluent, to give 1.1 g of the title compound as a glassy solid, melting at 65–75° C.

EXAMPLE 35

2-[2-(4-Methoxycarbonylmethylphenoxy)-1-methylethyl]-amino-1-(3.5-di-t-butyl-4-hydroxyphenyl)ethanol 1/2 fumarate (1/2 fumarate of Compound No. 3-27)

A procedure similar to that described in Example 6 was repeated, except that 3 g of 2-amino-1-(3,5-di-t-butyl-4-hydroxyphenyl)ethanol (prepared as described in Preparation 35), 2.2 g of methyl 4-(2-oxopropoxy)phenylacetate (prepared as described in Preparation 3), 100 ml of benzene, 60 ml of absolute methanol and 4 g of sodium cyanoborohydride were used, and that the product was purified by repeated column chromatography through silica gel, using as the eluent first ethyl acetate and then a 1:1 by volume mixture of benzene and ethyl acetate. 2.1 g of 2-[2-(4-methoxycarbonylmethylphenoxy)-1-methylethyl]amino-1-(3,5-di-t-butyl-4-hydroxyphenyl)ethanol were obtained. This product was then mixed with 246 mg of fumaric acid, and the mixture was recrystallized from ethyl acetate, to give 1.5 g of the title compound as crystals, melting at 171–174° C.

EXAMPLE 36

2-[2-(4-Carboxymethyl-2-chlorophenoxy)-1-methylethyl]-amino-1-(3-chlorophenyl)ethanol 1/4 hydrate (Compound No. 2-12)

A solution of 6.0 g of potassium hydroxide in 10 ml of water was added to a solution of 2.3 g of 2-[2-(4-methoxycarbonylmethyl-2-chlorophenoxy)-1-methylethyl] amino-1-(3-chlorophenyl)ethanol (prepared as described in Example 22) in 90 ml of methanol, and the resulting mixture was allowed to stand overnight. At the end of this time, the reaction mixture was poured into ice-water and the pH of the mixture was adjusted to a value of 7 by the addition of 1 N aqueous hydrochloric acid, after which it was irradiated with ultrasonic waves. The crystals which precipitated were collected by filtration and recrystallized from methanol, to give 0.97 g of the title compound as crystals, melting at 188–192° C.

EXAMPLE 37

2-{2-[4-(α-Methoxycarbonyl-α-hydroxymethyl) phenoxy]-1-methylethyl}amino-1-(3-chlorophenyl) ethanol (Compound No. 6-1)

Following a procedure similar to that described in Example 6, but using 5.2 g of methyl 4-(2-oxopropoxy)

mandelate (prepared as described in Preparation 36), 3.12 g of 2-amino-1-(3-chlorophenyl)ethanol (prepared as described in Preparation 8), 80 ml of dry benzene, 80 ml of absolute methanol and 4.2 g of sodium cyanoborohydride, and then purifying the reaction product by column chromatography through silica gel, using ethyl acetate as the eluent, 3.87 g of the title compound were obtained having an Rf=0.27 (thin layer chromatography over silica gel, using ethyl acetate as the developing solvent).

EXAMPLE 38

2-{2-[4-(2-Acetoxyethyl)phenoxy]-1-methylethyl}-amino-1-(3-chlorophenyl)ethanol (Compound No. 8-1)

Following a procedure similar to that described in Example 6, but using 2 g of 2-[4-(2-oxopropoxy)phenyl]-ethyl acetate (prepared as described in Preparation 37), 1.45 g of 2-amino-1-(3-chlorophenyl)ethanol (prepared as described in Preparation 8), 60 ml of dry benzene, 50 ml of absolute isopropanol and 2.06 g of sodium cyanoborohydride, and then purifying the reaction product by column chromatography through silica gel, using a 1:1 by volume mixture of ethyl acetate and hexane as the eluent, 0.49 g of the title compound was obtained, having an Rf=0.34 (thin layer chromatography over silica gel, using a 1:1 by volume mixture of ethyl acetate and hexane as the developing solvent).

EXAMPLE 39

2-{2-[4-Bis(methoxycarbonyl)methylphenoxy]-1-methylethyl}amino-1-(3-chlorophenyl)ethanol (Compound No. 3-18)

Following a procedure similar to that described in Example 6, but using 0.42 g of dimethyl 4-(2-oxopropoxy) phenylmalonate (prepared as described in Preparation 38), 0.26 g of 2-amino-1-(3-chlorophenyl)ethanol (prepared as described in Preparation 8), 50 ml of dry benzene, 50 ml of absolute methanol and 0.9 g of sodium cyanoborohydride, and then purifying the reaction product by column chromatography through silica gel, using ethyl acetate as the eluent, 0.4 g of the title compound was obtained, having an Rf=0.28 (thin layer chromatography over silica gel, using ethyl acetate as the developing solvent).

EXAMPLE 40

2-[2-(4-Methoxycarbonylmethylphenoxy)-1-methylethyl]-amino-1-(3,5-dichlorophenyl)ethanol (Compound No. 3-15)

Following a procedure similar to that described in Example 3, but using 3.0 g of 2-amino-1-(3,5-dichlorophenyl)ethanol (prepared as described in Preparation 39), 3.87 g of methyl 4-(2-oxopropoxy)phenylacetate (prepared as described in Preparation 3), 80 ml of benzene, 60 ml of absolute methanol and 2.9 g of sodium cyanoborohydride, and then purifying the reaction product by column chromatography through silica gel, using ethyl acetate as the eluent, 3.6 g of the title compound were obtained, having an Rf=0.51 (thin layer chromatography over silica gel, using ethyl acetate as the developing solvent).

EXAMPLE 41

2-[2-(4-Methoxycarbonylmethylphenoxy)-1-methylethyl]-amino-1-(3-chloro-4-fluorophenyl)ethanol (Compound No. 3-41)

Following a procedure similar to that described in Example 3, but using 3.0 g of 2-amino-1-(3-chloro-4-fluorophenyl)ethanol (prepared as described in Preparation 40), 4.22 g of methyl 4-(2-oxopropoxy)phenylacetate (prepared as described in Preparation 3), 80 ml of benzene, 60 ml of absolute methanol and 3.5 g of sodium cyanoborohydride, and then purifying the reaction product by column chromatography through silica gel, using ethyl acetate as the eluent, 3.31 g of the title compound were obtained having an Rf=0.22 (thin layer chromatography over silica gel, using ethyl acetate as the developing solvent).

EXAMPLE 42

2-[2-(4-Methoxycarbonylmethylphenoxy)-1-methylethyl]-amino-1-(3-bromophenyl)ethanol (Compound No. 3-14)

Following a procedure similar to that described in Example 3, but using 3.0 g of 2-amino-1-(3-bromophenyl) ethanol (prepared as described in Preparation 41), 3.67 g of methyl 4-(2-oxopropoxy)phenylacetate (prepared as described in Preparation 3), 80 ml of benzene, 60 ml of absolute methanol and 3.1 g of sodium cyanoborohydride, and then purifying the reaction product by column chromatography through silica gel, using ethyl acetate as the eluent, 3.33 g of the title compound were obtained having an Rf=0.25 (thin layer chromatography over silica gel, using ethyl acetate as the developing solvent).

EXAMPLE 43

2-[2-(4-Methoxycarbonylmethylphenoxy)-1-methylethyl]-amino-1-(3-trifluoromethylphenyl)ethanol (Compound No. 3-66)

Following a procedure similar to that described in Example 3, but using 3.0 g of 2-amino-1-(3-trifluoromethylphenyl)ethanol (prepared as described in Preparation 42), 3.89 g of methyl 4-(2-oxopropoxy) phenylacetate (prepared as described in Preparation 3), 80 ml of benzene, 60 ml of absolute methanol and 4.0 g of sodium cyanoborohydride, and then purifying the reaction product by column chromatography through silica gel, using ethyl acetate as the eluent, 2.2 g of the title compound were obtained having an Rf=0.32 (thin layer chromatography over silica gel, using ethyl acetate as the developing solvent).

EXAMPLE 44

2-[2-(4-Methoxycarbonylmethylphenoxy)-1-methylethyl]-amino-1-(3-methoxyphenyl)ethanol (Compound No. 3-62)

Following a procedure similar to that described in Example 3, but using 2.5 g of 2-amino-1-(3-methoxyphenyl)

ethanol (prepared as described in Preparation 43), 4.0 g of methyl 4-(2-oxopropoxy)phenylacetate (prepared as described in Preparation 3), 80 ml of benzene, 60 ml of absolute methanol and 2.75 g of sodium cyanoborohydride, and then purifying the reaction product by column chromatography through silica gel, using ethyl acetate as the eluent, 3.11 g of the title compound were obtained having an Rf=0.21 (thin layer chromatography over silica gel, using ethyl acetate as the developing solvent).

EXAMPLE 45

2-[2-(4-Methoxycarbonylmethylphenoxy)-1-methylethyl]-amino-1-(3-methylphenyl)ethanol (Compound No. 3-61)

Following a procedure similar to that described in Example 3, but using 2.5 g of 2-amino-1-(3-methylphenyl) ethanol (prepared as described in Preparation 44), 4.4 g of methyl 4-(2-oxopropoxy)phenylacetate (prepared as described in Preparation 3), 80 ml of benzene, 60 ml of absolute methanol and 4.5 g of sodium cyanoborohydride, and then purifying the reaction product by column chromatography through silica gel, using ethyl acetate as the eluent, 3.2 g of the title compound were obtained having an Rf=0.24 (thin layer chromatography over silica gel, using ethyl acetate as the developing solvent).

EXAMPLE 46

2-[2-(4-Methoxycarbonylmethylphenoxy)-1(R)-methylethyl]amino-1(R)-(3-chlorophenyl)ethanol (Compound No. 3-1)

Following a procedure similar to that described in Example 27, but using 3.02 g of N-[2-(4-methoxycarbonylmethylphenoxy)-1(R)-methylethyl]-2(R)-t-butyldimethylsilyloxy-2-(3-chlorophenyl)ethanamine (prepared as described in Preparation 50), 4.81 g of tetrabutylammonium fluoride and 100 ml of tetrahydrofuran, 1.7 g of the title compound were obtained having an Rf=0.39 (thin layer chromatography over silica gel, using ethyl acetate as the developing solvent).

$[\alpha]^{23}_D$-13.2° (c=0.99, methanol).

EXAMPLE 47

2-[2-(4-Methoxycarbonylmethylphenoxy)-1(R)-methylethyl]amino-1(R)-(3-chlorophenyl)ethanol fumarate (fumarate of Compound No. 3-1)

30 ml of hexane were slowly added to a solution of 1.6 g of 2-[2-(4-methoxycarbonylmethylphenoxy)-1(R)-methylethyl]amino-1(R)-(3-chlorophenyl)ethanol (prepared as described in Example 46) and 491 mg of fumaric acid in 5 ml of ethyl acetate, whilst irradiating the reaction mixture with ultrasonic waves. The crystals which precipitated were collected by filtration and dried, to give 1.95 g of the title compound as crystals, melting at 73–78° C.

$[\alpha]^{23}_D$-19.4° (c=1.01, methanol).

EXAMPLE 48

5-[4-{2(R)-[2(R)-(3-Chlorophenyl)-2-hydroxyethylamino]propoxy}benzyl]thiazolidine-2,4-dione (Compound No. 5-1)

88 g of tetrabutylammonium fluoride were added, whilst ice-cooling, to a solution of 46.2 g of 5-[4-{2(R)-[2(R)-(3-chlorophenyl)-2-t-butyldimethylsilyloxyethylamino]propoxy}benzyl]thiazolidine-2,4-dione (prepared as described in Preparation 52) in 500 ml of tetrahydrofuran, and the resulting mixture was stirred at room temperature for 15 hours. At the end of this time, the tetrahydrofuran solvent was removed by distillation under reduced pressure, and the residue was mixed with water and then extracted with ethyl acetate. The extract was washed with an aqueous solution of sodium chloride and then dried over anhydrous sodium sulfate. The ethyl acetate solvent was removed by distillation under reduced pressure, and the residue was purified by column chromatography through silica gel, using a 5:1 by volume mixture of ethyl acetate and ethanol as the eluent. The crude crystals thus obtained were recrystallized from a mixture of ethyl acetate and ethanol, to give 27.1 g of the title compound as crystals, melting at 100–112° C.

$[\alpha]^{23}_D$-4.4° (c=1.005, methanol).

EXAMPLE 49

5-[4-{2-[2-(2-Naphthyl)-2-hydroxyethylamino]-propoxy}benzyl]thiazolidine-2,4-dione (Compound No. 5-2)

Following a procedure similar to that described in Example 2, but using 520 mg of 2-amino-1-(2-naphthyl) ethanol (prepared as described in Preparation 9), 650 mg of 5-[4-(2-oxopropoxy)benzyl]thiazolidine-2,4-dione (prepared as described in Preparation 2), 150 ml of benzene, 100 ml of absolute methanol and 1.25 g of sodium borohydride, and then purifying the reaction product by column chromatography through silica gel, using a 5:1 by volume mixture of ethyl acetate and ethanol as the eluent, 0.49 g of the title compound was obtained as crystals, melting at 115–145° C.

EXAMPLE 50

5-[4-{2-[2-(3-Trifluoromethylphenyl)-2-hydroxyethylamino]propoxy}benzyl]thiazolidine-2,4-dione (Compound No. 5-3)

Following a procedure similar to that described in Example 2, but using 5.88 g of 2-amino-1-(3-trifluoromethylphenyl)ethanol (prepared as described in Preparation 42), 8 g of S-[4-(2-oxopropoxy)benzyl]-thiazolidine-2,4-dione (prepared as described in Preparation 2), 200 ml of benzene, 150 ml of absolute methanol and 5.4 g of sodium cyanoborohydride, and then purifying the reaction product by column chromatography through silica gel, using ethyl acetate as the eluent, 4.8 g of the title compound were obtained as crystals, melting at 100–105° C.

PREPARATION 1

2-[2-(4-Methoxycarbonylphenoxy)-1-methylethyl] amino-1-(3-chlorophenyl)ethanol

A procedure similar to that described in Example 12 was repeated, except that 3.43 g of 2-amino-1-(3-chlorophenyl) ethanol (prepared as described in Preparation 8), 4.5 g of methyl 4-(2-oxopropoxy)benzoate (prepared as described in European Patent Publication No. 6735), 100 ml of benzene, 100 ml of absolute methanol and 2.7 g of sodium borohydride were used, to give the title compound as crystals, melting at 99–101° C.

PREPARATION 2

5-[4-(2-Oxopropoxy)benzyl]thiazolidine-2,4-dione

2(a) 1-(4-Aminophenoxy)propan-2-one hydrochloride

A stream of hydrogen was passed through a mixture comprising 19.6 g of 1-(4-nitrophenoxy)propan-2-one, 300 ml of methanol, 30 ml of concentrated aqueous hydrochloric acid and 4 g of 10% w/v palladium-on-charcoal at room temperature for 5 hours. At the end of this time, the catalyst was filtered off, and the filtrate was concentrated by evaporation under reduced pressure, to give 20 g of the title compound.

2(b) Ethyl 2-chloro-3-[4-(2-oxopropoxy)phenyl] propionate 50 ml of 35% w/v aqueous hydrochloric acid were added to a mixture of 20 g of the 1-(4-aminophenoxy)propan-2-one hydrochloride [prepared as described in step (a) above] and 400 ml of acetone, and then a solution of 12 g of sodium nitrite in 20 ml of water was added dropwise to the resulting mixture, whilst ice-cooling; the mixture was then stirred at the same temperature for 20 minutes. At the end of this time, 130 g of ethyl acrylate and then 3.2 g of cuprous oxide were added in portions to the mixture, and the resulting mixture was stirred at room temperature for 1 hour. The reaction mixture was then concentrated by evaporation under reduced pressure, and the concentrate was mixed with water and ethyl acetate. The ethyl acetate layer was separated, washed with water and dried over anhydrous sodium sulfate; the solvent was then removed by distillation under reduced pressure. The resulting residue was purified by column chromatography through silica gel, using a 5:1 by volume mixture of hexane and ethyl acetate as the eluent, to give 11.3 g of the title compound having an Rf=0.31 (thin layer chromatography over silica gel, using a 5:1 by volume mixture of hexane and ethyl acetate as the developing solvent).

2(c) 5-[4-(2-Oxopropoxy)benzyl]thiazolidine-2,4-dione

A mixture comprising 12 g of ethyl 2-chloro-3-[4-(2-oxopropoxy)phenyl]propionate [prepared as described in step (b) above], 5 g of thiourea and 30 ml of sulfolane was heated at 90° C. for 3 hours, and then 100 ml of methoxyethanol were added to the mixture, which was then heated for a further 4 hours. At the end of this time, 40 ml of water and 20 ml of concentrated aqueous hydrochloric acid were added to the reaction mixture, and the resulting mixture was heated for 4.5 hours in an oil bath kept at 100° C. After this, the reaction mixture was mixed with water and ethyl acetate, and then the ethyl acetate layer was separated, washed with water and dried over anhydrous sodium sulfate; the solvent was then removed by distillation under reduced pressure. The resulting residue was purified by column chromatography through silica gel, using a gradient elution method, with mixtures of hexane and ethyl acetate ranging from 3:2 to 2:3 by volume as the eluent, followed by crystallization from a mixture of ethyl acetate and hexane, to give the title compound as crystals, melting at 158–159° C.

PREPARATION 3

Methyl 4-(2-oxopropoxy)phenylacetate

A mixture comprising 74.6 g of methyl 4-hydroxyphenylacetate, 92.2 g of bromoacetone, 125 g of potassium carbonate and 750 ml of dimethylformamide was stirred at room temperature for 1 day. At the end of this time, the reaction mixture was concentrated by evaporation under reduced pressure. The resulting concentrate was mixed with water and then extracted with ethyl acetate. The extract was washed with an aqueous solution of sodium chloride and dried over anhydrous sodium sulfate; the solvent was then removed by distillation under reduced pressure. The residue was purified by column chromatography through silica gel, using a 1:8 by volume mixture of ethyl acetate and benzene as the eluent, to give the title compound having an Rf=0.43 (thin layer chromatography over silica gel, using a 1:7 by volume mixture of ethyl acetate and benzene as the developing solvent).

PREPARATION 4

Methyl 4-(2-oxopropoxy)cinnamate

Following a procedure similar to that described in Preparation 3, but using 16 g of methyl 4-hydroxycinnamate, 14.9 g of bromoacetone, 20 g of potassium carbonate and 150 ml of dimethylformamide, the title compound was obtained as crystals, melting at 117–118° C. (after recrystallization from ethyl acetate)

PREPARATION 5

Methyl 3-[4-(2-oxopropoxy)phenyl]propionate

A stream of hydrogen was passed through a solution of 4 g of methyl 4-(2-oxopropoxy)cinnamate (prepared as described in Preparation 4) in a mixture of 200 ml of methanol and 100 ml of tetrahydrofuran and in the presence of 2 g of 10% w/w palladium-on-charcoal at room temperature for 2 hours. At the end of this time, the catalyst was filtered off, and the filtrate was concentrated by evaporation under reduced pressure. The resulting concentrate was purified by column chromatography through silica gel, using ethyl acetate as the eluent, to give the title compound having an Rf=0.54 (thin layer chromatography over silica gel, using a 2:1 by volume mixture of hexane and ethyl acetate as the developing solvent).

PREPARATION 6

Methyl 3-[4-(2-oxopropoxy)phenyl]lactate

Following a procedure similar to that described in Preparation 3, but using 1.8 g of methyl 4-hydroxyphenyllactate, 1.63 g of bromoacetone, 1.65 g of potassium carbonate and 150 ml of dimethylformamide, the title compound was obtained having an Rf=0.32 (thin layer chromatography over silica gel, using a 1:1 by volume mixture of hexane and ethyl acetate as the developing solvent).

PREPARATION 7

2-[4-(2-Oxopropoxy)phenyl]ethanol

Following a procedure similar to that described in Preparation 3, but using 10 g of 2-(4-hydroxyphenyl)ethanol, 21.6 g of bromoacetone, 30 g of potassium carbonate and 100 ml of dimethylformamide, the title compound was obtained having an Rf=0. 31 (thin layer chromatography over silica gel, using a 1:1 by volume mixture of hexane and ethyl acetate as the developing solvent).

PREPARATION 8

2-Amino-1-(3-chlorophenyl)ethanol 140 g of 3-chlorobenzaldehyde were added dropwise to a mixture of 112 g of trimethylsilylnitrile and 0.1 g of zinc iodide, and the resulting mixture was heated in an oil bath kept at 90° C. for 2.5 hours. At the end of this time, the reaction mixture was added dropwise to a mixture of 50 g of lithium aluminum hydride and 1200 ml of tetrahydrofuran, and the mixture was then heated under reflux for 40 minutes. It was then cooled with ice, after which 50 ml of water, 50 ml of a 15% w/v aqueous solution of sodium hydroxide and 50 ml of water were added, in that order. Insoluble materials were filtered off, and the filtrate was concentrated by evaporation under reduced pressure. The concentrate was purified by column chromatography through silica gel, using a 10:4:1 by volume mixture of ethyl acetate, ethanol and triethylamine as the eluent, followed by distillation in vacuo, to give the title compound as a liquid boiling at 140–141° C./2.5 mmHg (333 Pa).

PREPARATION 9

2-Amino-1-(2-naphthyl)ethanol

A mixture of 7.4 g of 2-naphthaldehyde, 9.93 g of trimethylsilylnitrile and a catalytic amount of zinc iodide was heated in an oil bath kept at 90° C. for 2 hours. At the end of this time, the reaction mixture was added dropwise to a mixture of 5.7 g of lithium aluminum hydride and 500 ml of tetrahydrofuran, whilst ice-cooling, and the resulting mixture was then heated under reflux for 3 hours, after which 5.7 ml of water, 5.7 ml of a 15% w/v aqueous solution of sodium hydroxide and 17.1 ml of water were added dropwise, in that order. Insoluble materials were filtered off and the filtrate was concentrated by evaporation under reduced pressure. The crystals obtained from the concentrate were recrystallized from a mixture of ethyl acetate and hexane, to give the title compound as crystals, melting at 113–116° C.

PREPARATION 10

2-Amino-1-(1-naphthyl)ethanol

Following a procedure similar to that described in Preparation 9, but using 7.4 g of 1-naphthaldehyde, 9.93 g of trimethylsilylnitrile, a catalytic amount of zinc iodide and 500 ml of tetrahydrofuran, the title compound was obtained as crystals, melting at 124–126.5° C.

PREPARATION 11

2-Amino-1-(2-chlorophenyl)ethanol

Following a procedure similar to that described in Preparation 8, but using 6.75 g of 2-chlorobenzaldehyde, 9.93 g of trimethylsilylnitrile, a catalytic amount of zinc iodide, 5.7 g of lithium aluminum hydride and 500 ml of tetrahydrofuran, the title compound was obtained as a liquid, boiling at 132° C./2 mmHg (266 Pa).

PREPARATION 12

2-Amino-1-(4-chlorophenyl)ethanol

Following a procedure similar to that described in Preparation 8, but using 6.75 g of 4-chlorobenzaldehyde, 9.93 g of trimethylsilylnitrile, a catalytic amount of zinc iodide, 5.7 g of lithium aluminum hydride and 500 ml of tetrahydrofuran, the title compound was obtained as a liquid, boiling at 141° C./2 mmHg (266 Pa).

PREPARATION 13

2-Amino-1-(3-fluorophenyl)ethanol

Following a procedure similar to that described in Preparation 8, but using 6 g of 3-fluorobenzaldehyde, 12.5 ml of trimethylsilylnitrile, a catalytic amount of zinc iodide, 5.7 g of lithium aluminum hydride and 500 ml of tetrahydrofuran, the title compound was obtained as a liquid, boiling at 117° C./1.5 mmHg (200 Pa).

PREPARATION 14

2-Amino-1-(3,4,5-trimethoxyphenyl)ethanol

Following a procedure similar to that described in Preparation 9, but using 9.42 g of 3,4,5-trimethoxybenzaldehyde, 12.5 ml of trimethylsilylnitrile, a catalytic amount of zinc iodide, 5.7 g of lithium aluminum hydride and 500 ml of tetrahydrofuran, the title compound was obtained as crystals, melting at 141° C. (after recrystallization from ethyl acetate).

PREPARATION 15

2-Amino-1-(3-phenoxyphenyl)ethanol 10 g of 3-phenoxybenzaldehyde cyanohydrin were added dropwise to a mixture of 5.1 g of lithium aluminum hydride and 500 ml of tetrahydrofuran, whilst ice-cooling, and the resulting mixture was heated under reflux for 4 hours. At the end of this time, 5 ml of water, 6 ml of a 15% w/v aqueous solution of sodium hydroxide and 18 ml of water were added in that order to the reaction mixture, whilst ice-cooling. Insoluble materials were filtered off, and the filtrate was concentrated by evaporation under reduced pressure. The concentrate was purified by column chromatography through silica gel, using a 3:1 by volume mixture of ethyl acetate and ethanol as the eluent, to give the title compound having an Rf=0.32 (thin layer chromatography over silica gel, using a 5:5:1 by volume mixture of ethyl acetate, ethanol and triethylamine as the developing solvent).

PREPARATION 16

2-Amino-1(S)-phenylethanol

16(a) Ethyl (S)-α-t-butyldimethylsilyloxy-α-phenylacetate

A solution of 31.4 g of t-butyldimethylsilyl chloride in 200 ml of dimethylformamide was added dropwise to a solution of 25 g of ethyl (S)-(+)-mandelate and 28.4 g of imidazole in 800 ml of dimethylformamide, and the resulting mixture was stirred overnight at 40° C. At the end of this time, the dimethylformamide solvent was removed by distillation under reduced pressure, and the resulting residue was purified by column chromatography through silica gel, using a 10:1 by volume mixture of hexane and ethyl acetate as the eluent, to give the title compound having an Rf=0.84 (thin layer chromatography over silica gel, using a 10:1 by volume mixture of hexane and ethyl acetate as the developing solvent).

16(b) 2(S)-t-Butyldimethylsilyloxy-2-phenylethanol 15.5 g of sodium borohydride were added in portions, whilst ice-cooling, to a solution of 20 g of ethyl (S)-α-t-butyldimethylsilyloxy-α-phenylacetate [prepared as described in step (a) above] in 500 ml of absolute methanol, and the resulting mixture was stirred overnight at room temperature. At the end of this time, 10 g of sodium borohydride were added in portions, whilst ice-cooling. The reaction mixture was then stirred at room temperature for 5 hours, after which it was concentrated by evaporation under reduced pressure, and the concentrate was mixed with water and ethyl acetate. The ethyl acetate layer was separated, washed with water and dried over anhydrous sodium sulfate, and then the solvent was removed by distillation under reduced pressure, to give the title compound as a crude product.

16(c) 2(S)-t-Butyldimethylsilyloxy-2-phenylethylazide

A solution of 13.36 g of crude 2(S)-t-butyldimethylsilyloxy-2-phenylethanol [prepared as described in step (b) above] and 5.36 g of triethylamine in 450 ml of tetrahydrofuran was cooled in an ice-acetone bath. A solution of 6.68 g of methanesulfonyl chloride in 50 ml of tetrahydrofuran was added dropwise to the solution, and the resulting mixture was stirred for 1 hour, whilst ice-cooling. The tetrahydrofuran solvent was then removed by distillation under reduced pressure, and the residue was mixed with water, with ethyl acetate and with an aqueous solution of sodium chloride. The ethyl acetate layer was separated, washed with an aqueous solution of sodium chloride and dried over anhydrous sodium sulfate; the solvent was then removed by distillation under reduced pressure. The resulting residue was dissolved in 300 ml of dimethylformamide, and 10.48 g of sodium azide were added to the solution thus obtained, which was then stirred overnight at 80° C. At the end of this time, the reaction mixture was freed from the dimethylformamide solvent by distillation under reduced pressure. The resulting residue was mixed with ethyl acetate and with an aqueous solution of sodium chloride. The ethyl acetate layer was separated, washed with an aqueous solution of sodium chloride and dried over anhydrous sodium sulfate. The ethyl acetate solvent was then removed by distillation under reduced pressure, and the resulting residue was purified by column chromatography through silica gel, using a 1:50 by volume mixture of ethyl acetate and hexane as the eluent, to give the title compound.

16(d) 2-Amino-1(S)-phenylethanol

A mixture of 2.6 g of lithium aluminum hydride in 400 ml of tetrahydrofuran was cooled in an ice-acetone bath, and a solution of 9.4 g of 2(S)-t-butyldimethylsilyloxy-2-phenylethylazide [prepared as described in step (c) above] in 100 ml of tetrahydrofuran was added dropwise to the cooled mixture. The mixture was stirred for 1 hour, whilst ice-cooling, after which 2.6 ml of water, 2.6 ml of a 15% w/v aqueous solution of sodium hydroxide and 7.8 ml of water were added dropwise to the reaction mixture, in that order. Insoluble materials were filtered off, and the filtrate was concentrated by evaporation under reduced pressure. The resulting residue was purified by column chromatography through silica gel, using a 1:2 by volume mixture of ethyl acetate and ethanol as the eluent, to give the title compound as crystals, melting at 69–70° C.

PREPARATION 17

Methyl 3-(2-oxopropoxy)phenylacetate

Following a procedure similar to that described in Preparation 3, but using 2.8 g of methyl 3-hydroxyphenylacetate, 3.5 g of bromoacetone, 4 g of potassium carbonate and 30 ml of dimethylformamide, the title compound was obtained having an Rf=0.41 (thin layer chromatography over silica gel, using a 2:5 by volume mixture of ethyl acetate and hexane as the developing solvent).

PREPARATION 18

Methyl 2-(2-oxopropoxy)phenylacetate

Following a procedure similar to that described in Preparation 3, but using 15.6 g of methyl 2-hydroxyphenylacetate, 34 g of bromoacetone, 25 g of potassium carbonate and 170 ml of dimethylformamide, the title compound was obtained having an Rf=0.39 (thin layer chromatography over silica gel, using a 3:1 by volume mixture of hexane and ethyl acetate as the developing solvent).

PREPARATION 19

Methyl 3-chloro-4-(2-oxopropoxy)phenylacetate

Following a procedure similar to that described in Preparation 3, but using 20 g of methyl 3-chloro-4-hydroxyphenylacetate, 27 g of bromoacetone, 28 g of potassium carbonate and 300 ml of dimethylformamide, the title compound was obtained having an Rf=0.33 (thin layer chromatography over silica gel, using a 3:1 by volume mixture of hexane and ethyl acetate as the developing solvent).

PREPARATION 20

2-{2-[3,4-Bis(methoxycarbonyl)phenoxy]-1-methylethyl}amino-1-(3-chlorophenyl)ethanol Following a procedure similar to that described in Example 6, but using 2 g of 2-amino-1-(3-chlorophenyl)ethanol (prepared as described in Preparation 8), 3.73 g of dimethyl 4-(2-oxopropoxy)phthalate (prepared as described in Preparation 54), 70 ml of benzene, 60 ml of absolute methanol and 1.32 g of sodium borohydride, the title compound was obtained having an Rf=0.29 (thin layer chromatography over silica gel, using ethyl acetate as the developing solvent).

PREPARATION 21

Methyl 2-hydroxy-5-(2-oxopropoxy)phenylacetate

A mixture of 5 g of 2,5-dihydroxyphenylacetic acid, 15 ml of absolute methanol and 15 ml of a 4 N solution of hydrogen chloride in dioxane was allowed to stand overnight, after which the solvent was removed by distillation under reduced pressure. The residue was dissolved in ethyl acetate, and the resulting solution was washed twice with water and then dried over anhydrous sodium sulfate. The ethyl acetate solvent was removed by distillation under reduced pressure, after which 4 g of the residue were mixed with 70 ml of anhydrous dimethylformamide, 3.32 g of bromoacetone and 3.04 g of potassium carbonate, and the resulting mixture was stirred overnight at room temperature. At the end of this time, the reaction mixture was poured into water, neutralized with aqueous hydrochloric acid and extracted with ethyl acetate. The extract was washed with water and dried over anhydrous sodium sulfate. The solvent was then removed by distillation under reduced pressure. The resulting residue was purified by column chromatography through silica gel, using first a 1:2 and subsequently a 3:4 by volume mixture of ethyl acetate and hexane as the eluent, to give the title compound having an Rf=0.43 (thin layer chromatography over silica gel, using a 1:2 by volume mixture of ethyl acetate and hexane as the developing solvent).

PREPARATION 22 p-[1,1,2,2-Tetrakis(ethoxycarbonyl)ethyl] phenoxyacetone

Following a procedure similar to that described in Preparation 3, but using 11.7 g of p-[1,1,2,2-tetrakis (ethoxycarbonyl)ethyl]phenol, 7.9 g of bromoacetone, 7.9 g of potassium carbonate and 100 ml of dimethylformamide, and then purifying the reaction product by column chromatography through silica gel, using a 1:2 by volume mixture of ethyl acetate and hexane as the eluent, the title compound was obtained having an Rf=0.21 (thin layer chromatography over silica gel, using a 1:2 by volume mixture of ethyl acetate and hexane as the developing solvent).

PREPARATION 23

Ethyl (R)-α-(t-butyldimethylsilyloxy)-α-phenylacetate

A solution of 31.4 g of t-butyldimethylsilyl chloride in 200 ml of dimethylformamide was added dropwise to a solution of 25 g of ethyl (R)-(–)-mandelate and 28.4 g of imidazole in 600 ml of anhydrous dimethylformamide, and the resulting mixture was stirred overnight at 40° C. The dimethylformamide solvent was then removed by distillation under reduced pressure, and the residue was mixed with water and then extracted with ethyl acetate. The extract was dried over anhydrous sodium sulfate, and the solvent was then removed by distillation under reduced pressure. The resulting residue was purified by column chromatography through silica gel, using a 1:10 by volume mixture of ethyl acetate and hexane as the eluent,. The title compound was obtained as a liquid, boiling at 129° C./3.5 mmHg (466 Pa) by distillation in vacuo.

$[\alpha]^{23}_D$ –40.8° (c=1.07, chloroform).

PREPARATION 24

Ethyl (S)-α-(t-butyldimethylsilyloxy)-α-phenylacetate

Following a procedure similar to that described in Preparation 23, but using 23.8 g of ethyl (S)-(+)-mandelate, 26.6 g of imidazole, 400 ml of dimethylformamide, 30.1 g of t-butyldimethylsilyl chloride and 100 ml of dimethylformamide, the title compound was obtained as a liquid, boiling at 125.5°/3.0 mmHg (400 Pa).

$[\alpha]^{23}_D$ +40.9° (c=1.02, chloroform).

PREPARATION 25

(R)-α-(t-Butyldimethylsilyloxy)-α-phenylacetaldehyde 20 ml of a 1 M hexane solution of diisobutylaluminum hydride were added dropwise at –65° C. and in an atmosphere of nitrogen to a solution of 5.9 g of ethyl (R)-α-(t-butyldimethylsilyloxy)-α-phenylacetate (prepared as described in Preparation 23) in 300 ml of dry hexane, and the resulting mixture was stirred at –40° C. for 4 hours. At the end of this time, 10 ml of a tetrahydrofuran solution containing 1 ml of water was added dropwise to the reaction mixture at –40° C., and then the mixture was stirred at room temperature for 1.5 hours. The reaction mixture was then filtered using a Celite (trade mark) filter aid, and the filtrate was concentrated by evaporation under reduced pressure. The resulting residue was purified by column chromatography through silica gel, using a 1:60 by volume mixture of ethyl acetate and hexane as the eluent, to give the title compound having an Rf=0.64 (thin layer chromatography over silica gel, using a 1:50 by volume mixture of ethyl acetate and hexane).

PREPARATION 26

(S)-α-(t-Butyldimethylsilyloxy)-α-phenylacetaldehyde

Following a procedure similar to that described in Preparation 25, but using 8.8 g of ethyl (S)-α-(t-butyldimethylsilyloxy)-α-phenylacetate (prepared as described in Preparation 24), 300 ml of dry hexane and 30 ml of a 1 M solution of diisobutylaluminum hydride in hexane, and then purifying the reaction product by column chromatography through silica gel, using a 1:60 by volume mixture of ethyl acetate and hexane as the eluent, the title compound was obtained having an Rf=0.29 (thin layer chromatography over silica gel, using a 1:80 by volume mixture of ethyl acetate and hexane as the developing solvent).

PREPARATION 27

Methyl 4-[2(R)-amino-1-propoxy]phenylacetate 16.6 g of diethyl azodicarboxylate were added, whilst ice-cooling, to a solution of 16.8 g of (R)-2-t-butoxycarbonylamino-1-propanol, 10.0 g of methyl 4-hydroxyphenylacetate and 24.0 g of triphenylphosphine in 50 ml of dry benzene, and the resulting mixture was stirred at room temperature for 2 days. At the end of this time, the benzene solvent was removed by distillation under reduced pressure. The resulting residue was dissolved in 100 ml of methanol, and 200 ml of a 4 N solution of hydrogen chloride in dioxane were added to the solution thus obtained, whilst ice-cooling, after which the mixture was allowed to stand at room temperature for 3 hours. The reaction mixture was then poured into water, and the pH of the aqueous mixture was adjusted to a value of 8 to 9 by the addition of an aqueous solution of potassium carbonate, and then the mixture was extracted with ethyl acetate. The extract was dried over anhydrous sodium sulfate, and the ethyl acetate solvent was removed by distillation under reduced pressure. The resulting residue was purified by column chromatography through silica gel, using a 3:1 by volume mixture of ethyl acetate and ethanol as the eluent, to give the title compound.

$[\alpha]^{23}_D$ –13.2° (c=1.048, chloroform).

PREPARATION 28

Methyl 4-[2(S)-amino-1-propoxy]phenylacetate

Following a procedure similar to that described in Preparation 27, but using 15.8 g of (S)-2-t-butoxycarbonylamino-1-propanol, 10.0 g of methyl 4-hydroxyphenylacetate, 24 g of triphenylphosphine, 70 ml of dry benzene, 15.7 g of diethyl azodicarboxylate, 50 ml of methanol and 70 ml of a 4 N solution of hydrogen chloride in dioxane, the title compound was obtained.

$[\alpha]^{23}_D$ +12.1° (c=1.054, chloroform).

PREPARATION 29

N-[2-(4-Methoxycarbonylmethylphenoxy)-1(R)-methylethyl]-2(R)-t-butyldimethylsilyloxy-2-phenylethanamine 630 mg of sodium cyanoborohydride were added, whilst ice-cooling, to a solution of 1.01 g of (R)-α-(t-butyldimethylsilyloxy)-α-phenylacetaldehyde (prepared as described in Preparation 25) and 750 mg of methyl 4-(2(R)-amino-1-propoxy)phenylacetate (prepared as described in Preparation 27) in 10 ml of absolute methanol, and the resulting mixture was allowed to stand overnight at room temperature. At the end of this time, the reaction mixture was mixed with ethyl acetate and water. The organic layer was separated, washed with water and dried over anhydrous sodium sulfate, after which the solvent was removed by distillation under reduced pressure. The resulting residue was purified by column chromatography through silica gel, using a 1:4 by volume mixture of ethyl acetate and hexane as the eluent, to give the title compound.

$[\alpha]^{23}_D$ –38.30 (c=1.138, chloroform).

PREPARATION 30

N-[2-(4-Methoxycarbonylmethylphenoxy)-1(S)-methylethyl]-2(S)-t-butyldimethylsilyloxy-2-phenylethanamine Following a procedure similar to that described in Preparation 29, but using 1.5 g of (S)-α-(t-butyldimethylsilyloxy)-α-phenylacetaldehyde (prepared as described in Preparation 26), 1.1 g of methyl 4-[2(S)-amino-1-propoxy]phenylacetate (prepared as described in Preparation 28), 10 ml of absolute methanol and 950 mg of sodium cyanoborohydride, the title compound was obtained.

$[\alpha]^{23}_D$ +38.3° (c=1.116, chloroform).

PREPARATION 31

N-[2-(4-Methoxycarbonylmethylphenoxy)-1(S)-methylethyl]-2(R)-t-butyldimethylsilyloxy-2-phenylethanamine Following a procedure similar to that described in Preparation 29, but using 750 mg of (R)-α-(t-butyldimethylsilyloxy)-α-phenylacetaldehyde (prepared as described in Preparation 25), 920 mg of methyl 4-[2(S)-amino-1-propoxy]phenylacetate (prepared as described in Preparation 28), 10 ml of absolute methanol and 500 mg of sodium cyanoborohydride, the title compound was obtained.

$[\alpha]^{23}_D$ –58.60 (c=0.998, chloroform).

PREPARATION 32

N-[2-(4-Methoxycarbonylmethylphenoxy)-1(R)-methylethyl]-2(S)-t-butyldimethylsilyloxy-2-phenylethanamine Following a procedure similar to that described in Preparation 29, but using 1.5 g of (S)-α-(t-butyldimethylsilyloxy)-α-phenylacetaldehyde (prepared as described in Preparation 26), 1.1 g of methyl 4-[2(R)-amino-1-propoxy]phenylacetate (prepared as described in Preparation 27), 10 ml of absolute methanol and 950 mg of sodium cyanoborohydride, the title compound was obtained.

$[\alpha]^{23}_D$ +58.4° (c=0.998, chloroform).

PREPARATION 33

2-{2-[2,4-Bis(methoxycarbonyl)phenoxy]-1-methylethyl}amino-1-(3-chlorophenyl)ethanol Following a procedure similar to that described in Example 8, but using 1.3 g of 2-amino-1-(3-chlorophenyl)ethanol (prepared as described in Preparation 8), 2.31 g of dimethyl 4-(2-oxopropoxy)isophthalate (prepared as described in Preparation 55), 60 ml of benzene, 50 ml of absolute methanol and 0.73 g of sodium borohydride, and then purifying the reaction product by column chromatography through silica gel, using a 10:1 by volume mixture of ethyl acetate and ethanol as the eluent, the title compound was obtained as crystals, melting at 112° C.

PREPARATION 34

Methyl 3-hydroxy-4-(2-oxopropoxy)phenylacetate

Following a procedure similar to that described in Preparation 21, but using 10 g of 3,4-dihydroxyphenylacetic acid, 30 ml of absolute methanol, 20 ml of a 4 N solution of hydrogen chloride in dioxane, 200 ml of anhydrous dimethylformamide, 8.74 g of bromoacetone and 8.02 g of potassium carbonate, the title compound was obtained having an Rf=0.37 (thin layer chromatography over silica gel, using a 1:2 by volume mixture of ethyl acetate and hexane as the developing solvent).

PREPARATION 35

2-Amino-1-(3.5-di-t-butyl-4-hydroxyphenyl)ethanol

A mixture comprising 44 g of 3,5-di-t-butyl-4-hydroxybenzaldehyde, 25 ml of trimethylsilylnitrile and a catalytic amount of zinc iodide was heated at 90° C. for 1 hour, whilst stirring. The reaction mixture was then added dropwise to a mixture of 16 g of lithium aluminum hydride and 600 ml of tetrahydrofuran, whilst ice-cooling, and the resulting mixture was stirred for 2 hours, whilst ice-cooling. At the end of this time, 16 ml of water, 16 ml of a 15% w/v aqueous solution of sodium hydroxide and 50 ml of water were added to the mixture, in that order. Insoluble materials were filtered off, and the filtrate was concentrated by evaporation under reduced pressure. The resulting residue was purified by column chromatography through silica gel, using a 20:20:1 by volume mixture of ethyl acetate, ethanol and triethylamine as the eluent, and by recrystallization from ethyl acetate, to give the title compound as crystals, melting at 137–140° C.

PREPARATION 36

Methyl 4-(2-oxopropoxy)mandelate 100 ml of a 10% w/w solution of trimethylsilyldiazomethane in hexane were added dropwise, whilst ice-cooling, to a solution of 12.38 g of 4-hydroxymandelic acid in a mixture of 150 ml of tetrahydrofuran and 30 ml of methanol, and the resulting mixture was stirred at room temperature for 1 hour, after which the solvent was removed by distillation under reduced pressure, and the resulting residue was mixed with 250 ml of dimethylformamide, 25.2 g of bromoacetone and 25.4 g of potassium carbonate. The reaction mixture was then worked up in a similar manner to that described in Preparation 3, to give the title compound having an Rf=0.39 (thin layer chromatography over silica gel, using a 1:1 by volume mixture of hexane and ethyl acetate as the developing solvent).

PREPARATION 37

2-[4-(2-Oxopropoxy)phenyl]ethyl acetate 1.96 g of acetic anhydride were added, whilst ice-cooling, to a mixture of 3.1 g of 2-[4-(2-oxopropoxy)phenyl]ethanol (prepared as described in Preparation 7), 50 ml of anhydrous tetrahydrofuran and 2.53 g of pyridine, and the resulting mixture was stirred at room temperature for 3.5 hours. At the end of this time, 12.5 g of pyridine and 9.8 g of acetic anhydride were added, whilst ice-cooling, and the mixture was allowed to stand at room temperature for 1 day, after which the solvent was removed by distillation under reduced pressure, and the residue was mixed with water and then extracted with ethyl acetate. The extract was dried over anhydrous sodium sulfate, and the solvent was removed by distillation under reduced pressure, to give the title compound having an Rf=0.71 (thin layer chromatography over silica gel, using a 1:1 by volume mixture of ethyl acetate and hexane as the developing solvent).

PREPARATION 38

Dimethyl 4-(2-oxopropoxy)phenylmalonate

Following a procedure similar to that described in Preparation 3, but using 0.5 g of dimethyl 4-hydroxyphenylmalonate, 0.612 g of bromoacetone, 0.616 g of potassium carbonate and 90 ml of dimethylformamide, and then purifying the reaction product by column chromatography through silica gel, using a 2:3 by volume mixture of ethyl acetate and hexane as the eluent, the title compound was obtained having an Rf=0.37 (thin layer chromatography over silica gel, using a 2:3 by volume mixture of ethyl acetate and hexane as the developing solvent).

PREPARATION 39

2-Amino-1-(3,5-dichlorophenyl)ethanol

Following a procedure similar to that described in Preparation 8, but using 10 g of 3,5-dichlorobenzaldehyde, 6.23 g of trimethylsilylnitrile, a catalytic amount of zinc iodide, 5.4 g of lithium aluminum hydride and 200 ml of tetrahydrofuran, and then purifying the reaction product by column chromatography through silica gel, using a 2:1 by volume mixture of ethyl acetate and ethanol as the eluent, the title compound was obtained having an Rf=0.19 (thin layer chromatography over silica gel, using a 10:3:1 by volume mixture of ethyl acetate, ethanol and triethylamine as the developing solvent) and melting at 66° C.

PREPARATION 40

2-Amino-1-(3-chloro-4-fluorophenyl)ethanol

Following a procedure similar to that described in Preparation 8, but using 10 g of 3-chloro-4-fluorobenzaldehyde, 6.89 g of trimethylsilylnitrile, a catalytic amount of zinc iodide, 5.99 g of lithium aluminum hydride and 200 ml of tetrahydrofuran, and then purifying the reaction product by column chromatography through silica gel, using a 2:1 by volume mixture of ethyl acetate and ethanol as the eluent, the title compound was obtained having an Rf=0.21 (thin layer chromatography over silica gel, using a 10:3:1 by volume mixture of ethyl acetate, ethanol and triethylamine as the developing solvent).

PREPARATION 41

2-Amino-1-(3-bromophenyl)ethanol

Following a procedure similar to that described in Preparation 8, but using 25 g of 3-bromobenzaldehyde, 14.78 g of trimethylsilylnitrile, a catalytic amount of zinc iodide, 13.2 g of lithium aluminum hydride and 400 ml of tetrahydrofuran, and then purifying the reaction product by column chromatography through silica gel, using a 2:1 by volume mixture of ethyl acetate and ethanol as the eluent, the title compound was obtained having an Rf=0.22 (thin layer chromatography over silica gel, using a 10:3:1 by volume mixture of ethyl acetate, ethanol and triethylamine as the developing solvent).

PREPARATION 42

2-Amino-1-(3-trifluoromethylphenyl)ethanol

Following a procedure similar to that described in Preparation 8, but using 25 g of 3-trifluoromethylbenzaldehyde, 15.71 g of trimethylsilylnitrile, a catalytic amount of zinc iodide, 12.8 g of lithium aluminum hydride and 400 ml of tetrahydrofuran, and then purifying the reaction product by column chromatography through silica gel, using a 2:1 by volume mixture of ethyl acetate and ethanol as the eluent, the title compound was obtained as crystals, melting at 72° C. and having an Rf=0.25 (thin layer chromatography over silica gel, using a 10:3:1 by volume mixture of ethyl acetate, ethanol and triethylamine as the developing solvent).

PREPARATION 43

2-Amino-1-(3-methoxyphenyl)ethanol

Following a procedure similar to that described in Preparation 8, but using 28 g of 3-methoxybenzaldehyde, 22.92 g of trimethylsilylnitrile, a catalytic amount of zinc iodide, 19.92 g of lithium aluminum hydride and 400 ml of tetrahydrofuran, and then purifying the reaction product by column chromatography through silica gel, using a 2:1 by volume mixture of ethyl acetate and ethanol as the eluent, the title compound was obtained having an Rf=0.18 (thin layer chromatography over silica gel, using a 10:3:1 by volume mixture of ethyl acetate, ethanol and triethylamine as the developing solvent).

PREPARATION 44

2-Amino-1-(3-methylphenyl)ethanol

Following a procedure similar to that described in Preparation 8, but using 25.75 g of 3-methylbenzaldehyde, 23.35 g of trimethylsilylnitrile, a catalytic amount of zinc iodide, 20.3 g of lithium aluminum hydride and 400 ml of tetrahydrofuran, and then purifying the reaction product by column chromatography through silica gel, using a 2:1 by volume mixture of ethyl acetate and ethanol as the eluent, the title compound was obtained having an Rf=0.22 (thin layer chromatography over silica gel, using a 10:3:1 by volume mixture of ethyl acetate, ethanol and triethylamine as the developing solvent).

PREPARATION 45

3-Chloromandelic acid

A mixture of 158 g of 3-chlorobenzaldehyde, 111.6 g of trimethylsilylnitrile and a catalytic amount of zinc iodide was heated at 90° C. for 2 hours, with stirring. The reaction mixture was ice-cooled, and 350 ml of concentrated aqueous hydrochloric acid were added to it. The resulting mixture was then heated under reflux for 1 hour, after which it was mixed with water and with ethyl acetate. The ethyl acetate layer was separated and mixed with a 30% w/v aqueous solution of sodium hydroxide. The aqueous layer was separated, washed three times with ethyl acetate and then acidified with concentrated aqueous hydrochloric acid, after which it was extracted with ethyl acetate. The extract was washed with water and dried over anhydrous sodium sulfate. The solvent was then removed by distillation under reduced pressure, to give the title compound as crystals, melting at 110–114° C.

PREPARATION 46

(R)-3-Chloromandelic acid and (S)-3-chloromandelic acid

A mixture of 100 g of 3-chloromandelic acid (prepared as described in Preparation 45) and 32.7 g of (R)-(+)-1-phenethylamine was dissolved in and recrystallized from a mixture of methanol and diethyl ether. The resulting crystals were collected by filtration, recrystallized three times from a mixture of methanol and diethyl ether and mixed with aqueous hydrochloric acid. The mixture was then extracted with ethyl acetate. The extract was dried over anhydrous sodium sulfate, and the solvent was removed by distillation under reduced pressure, to give (R)-3-chloromandelic acid as crystals, melting at 102–105° C.

$[\alpha]^{23}_D$ -153.7° (c=1.026, chloroform).

Hydrochloric acid was added to the filtrate obtained as described above, and the mixture was extracted with ethyl acetate. The extract was dried over anhydrous sodium sulfate, and the solvent was removed by distillation under reduced pressure. The resulting residue was mixed with 32.7 g of (S)-(–)-1-phenethylamine and was recrystallized three times from a mixture of methanol and diethyl ether, to give (S)-3-chloromandelic acid as crystals, melting at 101–104° C.

$[\alpha]^{23}_D$ +151.9° (c=1.008, chloroform).

PREPARATION 47

Methyl (R)-3-chloromandelate 18.3 g of a 10% w/v solution of trimethylsilyldiazomethane in hexane were added dropwise to a solution of 28 g of (R)-3-chloromandelic acid (prepared as described in Preparation 46) in a mixture of 300 ml of methanol and 700 ml of benzene, and the resulting mixture was stirred for 1 hour. At the end of this time, the solvent was removed by distillation under reduced pressure, to give the title compound having $[\alpha]^{23}_D$ -119.3° (c=1.00, chloroform) and an Rf=0.36 (thin layer chromatography over silica gel, using a 1:5 by volume mixture of ethyl acetate and hexane) as a crude product.

PREPARATION 48

Methyl (R)-α-t-butyldimethylsilyloxy-3-chlorophenylacetate

A solution of 31.6 g of t-butyldimethylsilyl chloride in 200 ml of dimethylformamide was added dropwise, whilst ice-cooling, to a solution of 28 g of methyl (R)-3-chloromandelate (prepared as described in Preparation 47) and 28.5 g of imidazole in 300 ml of dimethylformamide, and the resulting mixture was stirred at the same temperature for 30 minutes, after which it was allowed to stand overnight at 40° C. At the end of this time, the reaction mixture was concentrated by evaporation under reduced pressure, and the residue was mixed with water and ethyl acetate. The ethyl acetate layer was separated and dried over anhydrous sodium sulfate, and then the solvent was removed by distillation under reduced pressure. The resulting residue was purified by column chromatography through silica gel, using a 1:15 by volume mixture of ethyl acetate and hexane as the eluent, to give the title compound as crystals, melting at 36–38° C.

$[\alpha]^{23}_D$ -39.1° (c=1.014, chloroform).

PREPARATION 49

(R)-α-t-Butyldimethylsilyloxy-α-(3-chlorophenyl)acetaldehyde

A solution of 26 g of methyl (R)-α-t-butyldimethylsilyloxy-3-chlorophenylacetate (prepared as described in Preparation 48) in a mixture of 1000 ml of anhydrous hexane and 500 ml of dry toluene was cooled to –60° C., and then 124 ml of a 1 M solution of diisobutylaluminum hydride in hexane were added dropwise to the cooled solution. The resulting mixture was stirred at the same temperature for 3 hours, after which 10 ml of water were added to it, and the temperature of the mixture was gradually allowed to rise to room temperature. The reaction mixture was then mixed with water and ethyl acetate, after which it was stirred for 30 minutes. Insoluble materials were filtered off using a Celite (trade mark) filter aid, and the ethyl acetate layer was separated from the filtrate and dried over anhydrous sodium sulfate. The ethyl acetate solvent was removed by distillation under reduced pressure, and the residue was purified by column chromatography through silica gel, using a 1:60 by volume mixture of ethyl acetate and hexane as the eluent, to give the title compound having an Rf=0.36 (thin layer chromatography over silica gel, using a 1:60 by volume mixture of ethyl acetate and hexane as the developing solvent).

PREPARATION 50

N-[2-(4-Methoxycarbonylmethylphenoxyy)-1(R)-methylethyl]-2(R)-t-butyldimethylsilyloxy-2-(3-chlorophenyl)ethanamine Following a procedure similar to that described in Preparation 29, but using 5.2 g of (R)-α-t-butyldimethylsilyloxy-α-(3-chlorophenyl)acetaldehyde (prepared as described in Preparation 49), 4.24 g of methyl 4-[2(R)-amino-1-propoxy]phenylacetate (prepared as described in Preparation 27), 50 ml of absolute methanol and 3.4 g of sodium cyanoborohydride, the title compound was obtained having an Rf=0.20 (thin layer chromatography over silica gel, using a 1:4 by volume mixture of ethyl acetate and hexane as the developing solvent).

$[\alpha]^{23}_D$ –34.7° (c=1.024, chloroform).

PREPARATION 51

5-{4-[2(R)-Amino-1-propoxy]benzyl}thiazolidine-2,4-dione trifluoroacetate

51(a) 5-(4-Acetoxybenzylidene)thiazolidine-2,4-dione

A mixture comprising 200 g of p-hydroxybenzaldehyde, 229 g of thiazolidine-2,4-dione, 280 g of sodium acetate and 660 ml of dimethylacetamide was stirred at 1500 for 1 hour. It was then cooled, and 540 ml of dimethylacetamide and 370 ml of acetic anhydride were added to the reaction mixture. The resulting mixture was then stirred at 50° C for 1.5 hours, after which it was poured into water. The solid which precipitated was collected by filtration, washed with water, and dried over anhydrous sodium sulfate, to give the title compound.

51(b) 5-(4-Acetoxybenzyl)thiazolidine-2,4-dione 2.0 g of 5-(4-acetoxybenzylidene)thiazolidine-2,4-dione [prepared as described in step (a) above] was dissolved in 80 ml of acetic acid and was hydrogenated by passing hydrogen at atmospheric pressure through the solution at 90° C. for 5 hours in the presence of 2.0 g of 10% w/w palladium-on-charcoal. At the end of this time, the catalyst was filtered off, and the filtrate was diluted with toluene. The acetic acid solvent was then removed by distillation as a toluene azeotrope. The crystals which separated out on adding toluene and hexane to the concentrate were collected by filtration and dried to give the title compound.

51(c) 5-(4-Acetoxybenzyl)-3-triphenylmethylthiazolidine-2,4-dione 3.43 g of trimethylamine were added to a solution of 9.0 g of 5-(4-acetoxybenzyl)thiazolidine-2,4-dione [prepared as described in step (b) above] in 70 ml of methylene chloride, and a solution of 9.45 g of triphenylmethyl chloride in 30 ml of methylene chloride was added dropwise to the resulting mixture. The mixture was then stirred at room temperature for 1 hour, after which it was allowed to stand overnight at the same temperature. At the end of this time, the reaction mixture was mixed with water and ethyl acetate, and the organic layer was separated, washed with a saturated aqueous solution of sodium chloride, and dried over anhydrous sodium sulfate. The crystals which separated out on distilling off the solvent under reduced pressure, were washed with a mixture of hexane and ethyl acetate and dried, to give the title compound.

51(d) 5-(4-Hydroxybenzyl)-3-triphenylmethylthiazolidine-2,4-dione

A solution of 2.99 g of a 28% w/v methanolic solution of sodium methoxide in 10 ml of methanol was added dropwise, whilst ice-cooling, to a solution of 7.86 g of 5-(4-acetoxybenzyl)-3-triphenylmethylthiazolidine-2,4-dione [prepared as described in step (c) above] in 70 ml of toluene, and the resulting mixture was stirred at room temperature for 1 hour, after which it was allowed to stand overnight at the same temperature. The pH of the reaction mixture was then adjusted to a value of 4 by the addition of 1 N aqueous hydrochloric acid, and the mixture was extracted with ethyl acetate. The extract was washed with water and dried over anhydrous sodium sulfate. The solvent was then removed by distillation under reduced pressure, and the crystals which appeared in the residue were collected, washed with hexane and dried, to give the title compound.

51(e) 5-{4-[2(R)-t-Butoxycarbonylaminopropoxy]-benzyl}-3-triphenylmethylthiazolidine-2,4-dione 13.2 g of diethyl azodicarboxylate were added dropwise to a solution of 20.7 g of triphenylphosphine in 300 ml of benzene and the mixture was stirred at room temperature for 30 minutes. At the end of this time, 35.0 g of S-(4-hydroxybenzyl)-3-triphenylmethylthiazolidine-2,4-dione [prepared as described in step (d) above] were added to the mixture, and the resulting mixture was stirred at room temperature for 1 hour. 13.2 g of (R)-2-t-butoxycarbonylamino-1-propanol were added to the mixture, which was then allowed to stand overnight. At the end of this time, 40.9 g of triphenylphosphine, 23.68 ml of diethyl azodicarboxylate and 33 g of (R)-2-t-butoxycarbonylamino-1-propanol were added to the reaction mixture, in that order, in 3 or 4 separate portions, and the mixture was then stirred for 2 days. After this time, the benzene solvent was removed from the reaction mixture by distillation under reduced pressure, and the residue was purified by column chromatography through silica gel, using a 1:3 by volume mixture of ethyl acetate and hexane as the eluent, to give 30 g of the title compound as crystals, melting at 153–157° C.

$[\alpha]^{23}_D$ +19.5° (c=1.000, chloroform).

51(f) 5-{4-[2(R)-Aminopropoxy]benzyl}thiazolidine-2,4-dione trifluoroacetate 500 ml of trifluoroacetic acid were added dropwise, whilst ice-cooling, to a solution of 85.5 g of 5-{4-[2(R)-t- butoxycarbonylaminopropoxy]benzyl}-3-triphenylmethylthiazolidine-2,4-dione [prepared as described in step (e) above] in 700 ml of methylene chloride, and the resulting mixture was stirred at room temperature for 4 hours. At the end of this time, the reaction mixture was freed from the methylene chloride solvent and the trifluoroacetic acid by distillation under reduced pressure, and a mixture of benzene and a small amount of ethyl acetate was added to the residue. The crystals which precipitated were collected by filtration and were recrystallized from a mixture of methanol and ethyl acetate, to give the title compound as crystals, melting at 162–166° C.

$[\alpha]^{23}_D$–13.0° (c=0.885, methanol).

PREPARATION 52

5-[4-{2(R)-[2(R)-(3-chlorophenyl)-2-t-butyldimethylsilyloxyethylamino]propoxy}benzyl]-thiazolidine-2,4-dione A mixture comprising 36.5 g of 5-{4-[2(R)-aminopropoxy]benzyl}thiazolidine-2,4-dione trifluoroacetate (prepared as described in Preparation 51), 98.4 g of (R)-α-(t-butyldimethylsilyloxy)-α-phenylacetaldehyde (prepared as described in Preparation 25) and 400 ml of absolute methanol was stirred at room temperature for 2.5 hours and then 29.0 g of sodium cyanoborohydride were added in portions to the mixture, whilst cooling it in an ice-sodium chloride bath. The reaction mixture was then allowed to stand overnight at room temperature, after which the methanol solvent was removed by distillation under reduced pressure. The resulting residue was mixed with water and ethyl acetate. The ethyl acetate layer was separated, washed with an aqueous solution of sodium chloride and dried over anhydrous sodium sulfate. The ethyl acetate solvent was then was removed by distillation under reduced pressure, and the resulting residue was purified by column chromatography through silica gel, using a 2:1 by volume mixture of ethyl acetate and hexane as the eluent, to give the title compound.

$[\alpha]^{23}_D$–26.30 (c=0.988 chloroform).

PREPARATION 53

2-{2-[4-(2-Methoxycarbonylethenyl)phenoxy]-1-methylethyl}amino-1-(3-chlorophenyl)ethanol A solution of 6.07 g of 2-amino-1-(3-chlorophenyl)ethanol (prepared as described in Preparation 8) and 6.5 g of methyl 4-(2-oxopropoxy)cinnamate (prepared as described in Preparation 4) in 100 ml of benzene was heated under reflux for 3.5 hours and the water formed during the reaction was removed continuously. At the end of this time, the reaction mixture was freed from the benzene used as solvent by distillation under reduced pressure, and the resulting residue was dissolved in 100 ml of absolute methanol. 3 g of sodium borohydride were added to this solution, whilst ice-cooling, and the resulting mixture was stirred at room temperature overnight and then at 60° C. for 5 hours. The reaction mixture was then concentrated by evaporation under reduced pressure, and the concentrate was extracted with ethyl acetate. The extract was washed with water and was dried over anhydrous sodium sulfate. The solvent was removed by distillation under reduced pressure, and the resulting residue was purified by column chromatography through silica gel, using a 10:1 by volume mixture of ethyl acetate and ethanol as an eluent to give two fractions. The product thus obtained was recrystallized from a mixture of ethyl acetate and hexane, to give the title compound, melting at 97–103° C.

PREPARATION 54

Dimethyl 4-(2-oxopropoxy)phthalate

Following a procedure similar to that described in Preparation 3, but using 10.5 g of dimethyl 4-hydroxyphthalate, 13.7 g of bromoacetone, 14 g of potassium carbonate and 150 ml of dimethylformamide, the title compound was obtained as an oil, having an Rf=0.48 (thin layer chromatography over silica gel, using a 1:1 by volume mixture of haexane and ethyl acetate as the developing solvent).

PREPARATION 55

Dimethyl 4-(2-oxopropoxy)isophthalate

Following a procedure similar to that described in Preparation 3, but using 10.5 g of dimethyl 4-hydroxyisophthalate, 15 g of bromoacetone, 17 g of potassium carbonate and 100 ml of dimethylformamide, and then purifying the reaction product by column chromatography through silica gel, using a 2:1 by volume mixture of hexane and ethyl acetate as the eluent, the title compound was obtained as crystals, melting at 115–116° C.

We claim:

1. A process for preparing a compound of the formula

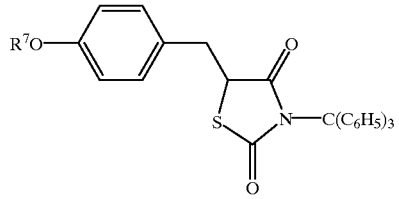

wherein $R^7$ is a hydrogen atom or an acetyl group which comprise the steps of (i) reacting p-hydroxybenzaldehyde with thiazolidine-2,4-dione and thereafter reacting the product with acetic anhydride to form 5-(4-acetoxybenzylidene)thiazolidine-2,4-dione;

(ii) hydrogenating said 5-(4-acetoxybenzylidene)thiazolidine-2,4-dione to form 5-(4-acetoxybenzyl)thiazolidine-2,4-dione;

(iii) reacting said 5-(4-acetoxybenzyl)thiazolidine-2,4-dione with triphenylmethyl chloride to form 5-(4-acetoxybenzyl)-3-triphenylmethylthiazolidine-2,4-dione; and (iv) when $R^7$ is a hydrogen atom, hydrolysing said 5-(4-acetoxybenzyl)-3-triphenylmethylthiazolidine-2,4-dione to form 5-(4-hydroxybenzyl)-3-triphenylmethylthiazolidine-2,4-dione.

* * * * *